(12) United States Patent
Osl et al.

(10) Patent No.: US 11,639,373 B2
(45) Date of Patent: May 2, 2023

(54) THERAPEUTIC AND DIAGNOSTIC AGENTS FOR CANCER

(71) Applicant: TECHNISCHE UNIVERSITÄT MÜNCHEN, Munich (DE)

(72) Inventors: Theresa Osl, Garching bei München (DE); Hans-Jürgen Wester, Ilmmünster (DE); Margret Schottelius, Munich (DE)

(73) Assignee: TECHNISCHE UNIVERSITÄT MÜNCHEN, Munich (DE)

( * ) Notice: Subject to any disclaimer, the term of this patent is extended or adjusted under 35 U.S.C. 154(b) by 0 days.

(21) Appl. No.: 17/275,855

(22) PCT Filed: Sep. 11, 2019

(86) PCT No.: PCT/EP2019/074195
§ 371 (c)(1),
(2) Date: Mar. 12, 2021

(87) PCT Pub. No.: WO2020/053255
PCT Pub. Date: Mar. 19, 2020

(65) Prior Publication Data
US 2022/0041674 A1  Feb. 10, 2022

(30) Foreign Application Priority Data
Sep. 12, 2018 (EP) .................... 18194121

(51) Int. Cl.
*A61K 38/12* (2006.01)
*A61K 47/65* (2017.01)
*A61K 51/02* (2006.01)
*C07K 7/64* (2006.01)
*C07K 14/52* (2006.01)
*A61K 49/00* (2006.01)
*A61K 51/08* (2006.01)
*A61K 38/00* (2006.01)

(52) U.S. Cl.
CPC .............. *C07K 14/52* (2013.01); *A61K 38/12* (2013.01); *A61K 47/65* (2017.08); *A61K 49/0056* (2013.01); *A61K 51/02* (2013.01); *A61K 51/088* (2013.01); *C07K 7/64* (2013.01); *A61K 38/00* (2013.01)

(58) Field of Classification Search
CPC ........ A61K 38/12; A61K 47/64; A61K 47/65; A61K 51/02; C07K 7/64
See application file for complete search history.

(56) References Cited

FOREIGN PATENT DOCUMENTS

| WO | WO 2008/083312 | 7/2008 |
|----|----------------|--------|
| WO | WO 2008/150689 | 12/2008 |
| WO | WO 2011/131731 | 10/2011 |
| WO | WO 2015/185162 | 12/2015 |

OTHER PUBLICATIONS

Behnam et al., "C-terminal residue optimization and fragment merging: discovery of a potent peptide-hybrid inhibitor of Dengue protease," *ACS Medicinal Chemistry Letters*, 5(9):1037-1042, 2014.
Demmer et al.; "A conformationally frozen peptoid boosts CXCR4 affinity and anti-HIV activity," *Angewandte Chemie International Edition*, 51(32):8110-8113, 2012.
Osl, "Development of cyclic pentapeptide ligands for chemokind receptor targeting," retrieved from http://mediatum.ub.tum.de/doc/1342124/1342124.pdf, 2018.
PCT International Search Report and Written Opinion issued in International Application No. PCT/EP2019/074195, dated Oct. 9, 2019.
PCT International Search Report and Written Opinion issued in International Application No. PCT/EP2019/074196, dated Dec. 17, 2019.
Schottelius et al., "[$^{77}$Lu]pentixather: Comprehensive Preclinical Characterization of a First CXCR4-directed Endoradiotherapeutic Agent," *Theranostics*, 7(9):2350-2362, 2017.

*Primary Examiner* — Jeffrey E. Russel
(74) *Attorney, Agent, or Firm* — Parker Highlander PLLC

(57) ABSTRACT

The present disclosure relates to imaging and endoradiotherapy of diseases involving chemokine receptor 4 (CXCR4). Provided are compounds which bind or inhibit CXCR4 and furthermore carry at least one moiety which is amenable to labeling. Provided are also medical uses of such compounds.

28 Claims, 7 Drawing Sheets

THERAPEUTIC AND DIAGNOSTIC AGENTS FOR CANCER

Figure 1:
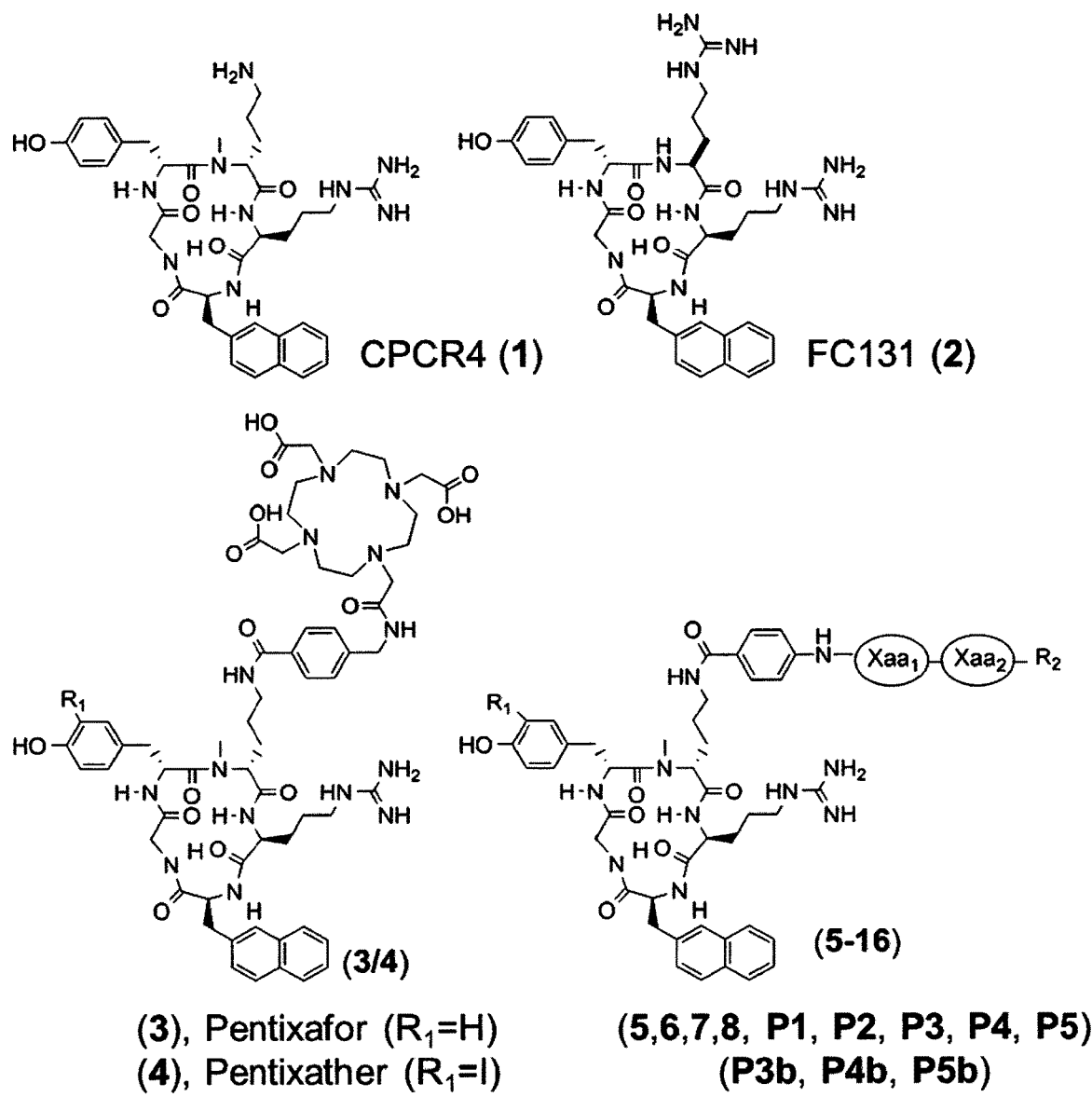

This application is a national phase application under 35 U.S.C. § 371 of International Application No. PCT/EP2019/074195, filed Sep. 11, 2019, the entire contents of which are hereby incorporated by reference, and which claims the benefit of EP 18194121.2, filed Sep. 12, 2018.

The present disclosure relates to imaging and endoradiotherapy of diseases involving chemokine receptor 4 (CXCR4). Provided are compounds which bind or inhibit CXCR4 and furthermore carry at least one moiety which is amenable to labeling. Provided are also medical uses of such compounds.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Binding of the only endogenous ligand CXCL12 (formerly termed SDF-1a) to its cognate receptor, the chemokine receptor 4 (CXCR4) [1], activates the downstream protein kinase B (AKT)/mitogen-activated protein kinases (MAPK) signaling pathway, which leads to the alteration of gene expression, actin polymerization, cell skeleton rearrangement and cell migration. The physiological functions of the CXCL12/CXCR4 axis include embryogenesis (regulation of embryonic stem cell migration and positioning), immune response (leucocyte trafficking to sites of inflammation), embryo implantation (positioning of blastocysts in maternal endometrium), hematopoiesis (homing and differentiation of hematopoietic stem/progenitor cells in the bone marrow), brain development and neo-angiogenesis [2-6]. Consequently, genetic defects displayed in Cxcl12 and Cxcr4 gene-deleted mice exhibit identical, lethal phenotypes with severely impaired hematopoiesis and CNS development [7].

The CXCR4 receptor has been found to be involved in a variety of diseases. For example, it mediates HIV-1 entry into T-cells as a co-receptor where it was first identified [3]. Furthermore, in rheumatoid arthritis (RA) CXCR4 expressing CD4+ memory T cells accumulate in the inflamed synovium because of the high local CXCL12 concentration [8]. In the pathogenesis of atherosclerosis, chronic inflammation of the arterial wall characterized by chemokine-mediated influx of leukocytes plays a central role [9]. The cytokine macrophage migration inhibitory factor (MIF) is a unique pro-inflammatory regulator of many acute and chronic inflammatory diseases that contribute to lesion progression and plaque inflammation. These chemokine-like functions are mediated through interaction of MIF with the chemokine receptors CXCR2 and CXCR4, thus suggesting a central role of CXCR4 in atherosclerotic plaque development, vascular remodeling after injury, in atherosclerosis plaque destabilization and aneurysm formation [10].

In addition, CXCR4 is involved in B-cell trafficking and tissue localization in chronic leukemia patients [11] as well as the regulation of organ specific metastasis in different breast cancer models [12]. Furthermore, pronounced CXCR4 overexpression has been detected in more than 20 human tumor types, including hematopoietic malignancies, brain neoplasm, gastrointestinal cancer and other cancer types [2, 13-14]. A method for the early assessment of the metastatic potential and metastatic spread of tumors therefore represents a valuable tool for therapy planning, monitoring and control, since cancer metastasis is one of the critical factors affecting the life expectancy of patients.

Given the undisputed relevance of CXCR4 as a diagnostic and therapeutic molecular target, a multitude of CXCR4 targeted peptidic and non-peptidic antagonists have been developed during the last decade. Amongst them, the bicyclam AMD3100 (plerixafor/Mozobil) is the only compound that has been approved by the FDA (in 2008) for the mobilization of stem cells and for the treatment of hematological and other cancers [7, 15-17]. In preclinical studies using mouse models of a variety of human hematological as well as solid cancers, antitumor therapies using either alternative small molecule CXCR4 antagonists such as AMD3465 [18-19] or MSX-122 [20], peptidic CXCL12 derivatives (CTCE-9908 [21], BKT-140 [22-24], POL-5551 [25-27]) or anti-CXCR4-antibodies [28-29] were shown to consistently lead to prolonged overall survival, primarily by effectively preventing distant organ metastasis [30]. Another potent CXCR4 antagonist, LY2510924 (cyclo[Phe-Tyr-Lys (iPr)-D-Arg-2-Nal-Gly-D-Glu]-Lys(iPr)-NH2) [31-32], exhibited high antitumor activities in solid tumor and breast cancer metastatic models and is currently evaluated in phase i1 clinical studies (NCT01391130 and NCT1439568). Lactam-cyclized heptapeptides were reported to be potent CXCR4 antagonists with high efficiency in the treatment of cancers, rheumatoid arthritis, pulmonary fibrosis, and HIV infection (WO 2008150689 A1). Recently, disulfide-bridged cyclic heptapeptide antagonists (WO/2011/092575A1) were shown to exhibit high in vivo stability [33-34], to efficiently inhibit lung metastasis in a melanoma model [35] and to reduce the metastatic potential of HCC and osteosarcoma in a mouse model [36]. A modified analog (R29, Ac-Arg-Ala-[D-Cys-Arg-Phe-His-Pen]-COOH) efficiently reverts the suppressive activity of T-regulatory cells in renal cancer [37].

Amongst these CXCR4 targeted antagonists, T-140 based peptides were the first compounds to be employed for molecular imaging of CXCR4-expression in vivo; different analogs, either radiolabeled with $^{18}$F or $^{68}$Ga or conjugated with fluorescent dyes as well as corresponding bimodal probes have been employed for the non-invasive detection and visualization of CXCR4-expressing tissues using positron emission tomography (PET), optical or SPECT imaging [38-45].

Furthermore, cyclic pentapeptides based on the N-terminal sequence of CXCL12 [46] or, more importantly, the downsized T-140 binding sequence cyclo(Gly-Nal-Arg-Arg-D-Tyr) (FC-131) [47] have been extensively evaluated. Detailed structure activity relationship (SAR) studies have highlighted the relevance of single amino acid residues and their stereochemistry as well as of amide bond methylation [48-53] for optimal CXCR4 affinity and antagonistic activity. Based on these findings and own SAR studies, our group has developed a first pentapeptide-based CXCR4-targeted molecular imaging agent, [$^{68}$Ga]pentixafor. Substitution of Arg2 (in FC131) by D-Ornithine and N-methylation of D-Orn led to the CPCR4-scaffold (cyclo(D-Tyr$^1$-D-[NMe]Orn$^2$-Arg$^3$-Nal$^4$-Gly$^5$)), which showed excellent binding affinity towards CXCR4 [54]. Further functionalization of the Orn2 sidechain with a suitable linker (4-aminomethyl-benzoic acid, AMBS) and a DOTA (1,4,7,10-tetraazacyclododecane-1,4,7,10-tetraacetic acid) chelator led to pentixafor (cyclo(D-Tyr$^1$-D-[NMe]Orn$^2$(AMBS-DOTA)-Arg$^3$-Nal$^4$-Gly$^5$), also termed CPCR4.2) [54-56]; WO2007/096662, WO 2009/027706, WO 2011/131735). Its $^{68}$Ga-labeled analog, [$^{68}$Ga]pentixafor [57] shows high affinity and selectivity for human CXCR4, rapid renal excretion and very low non-specific background accumulation and thus allows sensitive and high-contrast imaging of CXCR4 expressing tissues in vivo using PET. Besides its successful application in patients with lymphoma [58], multiple myeloma [59-61], AML [62], SCLC [63], glioblastoma [64] or other solid tumors [65], [$^{68}$Ga]pentixafor-PET has recently been shown to be a valuable tool for the in vivo detection of inflammatory processes e.g. after myocardial infarction [66-68] or stroke [69], in atherosclerosis [70-72] or other inflammatory diseases [73-74].

An alternative peptide backbone (cyclo(D-3-iodo-Tyr[1]-D-[NMe]Orn[2]-Arg[3]-Nal[4]-Gly[5])) was employed for the synthesis of a first CXCR4 targeted endoradiotherapeutic agent, namely pentixather (cyclo(D-3-iodo-Tyr[1]-D-[NMe]Orn[2] (AMBS-DOTA)-Arg[3]-Nal[4]-Gly[5]) [75-76] (WO 2015/185162). First very promising results have been obtained using [$^{177}$Lu]- and [$^{90}$Y]pentixather for PRRT (peptide receptor targeted radionuclide therapy) in patients with multiple myeloma [77-78], and consequently a clinical trial further evaluating the [$^{68}$Ga]pentixafor/[$^{177}$Lu/$^{90}$Y]pentixather based CXCR4 targeted theranostic concept has recently been initiated.

Furthermore, ongoing preclinical studies are directed towards establishing the potential of alpha-therapy in disseminated micrometastatic hematological cancers using [$^{213}$Bi/$^{225}$Ac]pentixather. Unfortunately, however, the applicability of the pentixafor/pentixather peptide construct is limited to these specific (pre)clinical scenarios; the peptide-linker-chelate construct as such is highly optimized and only allows minor structural modifications in the chelator region [79-82], while the implementation of alternative labeling strategies (e.g. using $^{99m}$Tc or $^{18}$F or fluorescent dyes) is not tolerated.

Accordingly, the present invention in a first aspect relates to a compound of the following formula (I)

(I)

or a pharmaceutically acceptable salt thereof, wherein:

$R^1$ is an alkanediyl chain, preferably a C1-C6 alkanediyl chain, more preferably a C2-C3 alkanediyl chain, and most preferably a linear $C_3H_6$-moiety;

$R^2$ is a group of formula (II):

(II)

of formula (III):

(III)

or of formula (IV):

(IV)

which is linked to the remainder of the compound with the bond marked by the dashed line, and wherein $R^A$ is H or alkyl, preferably H or C1-C6 alkyl, more preferably H or C1-3 alkyl, most preferably H or methyl;

$R^B$ is substituted alkyl, preferably substituted C1-C6 alkyl, which substituted alkyl is substituted with at least one group selected from —NH$_2$ and the guanidino group —NH—C(=NH)—NH$_2$;

$R^C$ is H or optionally substituted alkyl, alkyl preferably being C1-C6 alkyl, more preferably C1-3 alkyl, most preferably C1 or C3 alkyl, with one or more optional substituents being selected from —NH$_2$, —NH—C(=NH)—NH$_2$, —COOH, —CONH$_2$, —OH, —SH, —S—CH$_3$, and 5- to 10-membered carbocycle or 5- to 10-membered heterocycle containing oxygen, nitrogen and/or sulfur as heteroatom(s), said carbocycle or heterocycle preferably being aryl or heteroaryl, wherein $R^C$ may be further substituted with or may comprise a cytotoxic agent, such as an auristatin analogue;

p is 0, 1 or 2;
q is 0, 1 or 2;
p+q is 0, 1 or 2;
m is 0 or 1, preferably 0;

$R^D$ is H or forms a 5 or 6-membered heterocycle together with the adjacent nitrogen which heterocycle also includes a part of $R^E$;

$R^E$ is a group which comprises at least one of the following:
(i) a chelating moiety,
(ii) a chelate formed by the chelating moiety (i) with a chelated radioactive or non-radioactive cation or anion,
(iii) a moiety carrying a covalently bound radioisotope, preferably $^{18}$F-fluoride, or a precursor suitable to be labeled with such a radioisotope;
(iv) a cytotoxic moiety, such as an auristatin analogue, (v) a fluorescent moiety (a dye), such as e.g. Cy5 or Cy7; and R³ is H or I.

In the fields of targeted endoradiotherapy as well as of molecular imaging, a commonly adopted approach in the design of suitable agents is the derivatization of a first moiety which binds to the molecular target of interest with a second moiety comprising a label, a therapeutic radionuclide or a diagnostic radionuclide. For the purpose of connecting the two moieties, i.e. the binding moiety and the radionuclide-carrying moiety, linkers are employed.

Generally speaking, the design of linkers does not receive particularly much attention, because there is a common understanding in the art that the linker primarily serves to establish a certain distance between the binding moiety and the radionuclide-carrying moiety. A primary goal is to avoid interference of the radionuclide-carrying moiety with the binding properties of the binding moiety. The general understanding is that the linker itself does not significantly contribute to target binding.

The present inventors surprisingly discovered that the insertion of a peptide linker between the cyclic pentapeptide binding moiety and the label of known CXCR4 binders provide for distinct and unexpected advantages.

Advantages include increased CXCR4 binding and better internalization. As explained above, this is unexpected.

A further advantage is the provision of a theranostic agent, i.e. an agent which combines in a single molecule diagnostic and therapeutic properties. As explained in the background section herein above, the provision of such molecule is not a trivial exercise. While in an ideal scenario, therapeutic and diagnostic agents differ only with regard to the radionuclide (e.g. a radiometal), experience with previously existing CXCR4 binders demonstrated that even a change of only the radionuclide altered binding properties.

In particular, compounds of the invention provide flexibility in the part of the compound which is amenable to detection, thereby allowing the design of novel CXCR4-targeted probes labelled with a broad palette of radionuclides and/or fluorescent dyes for molecular imaging and therapeutic applications.

A yet further advantage is significant affinity not only for human CXCR4, but also for murine CXCR4. The latter two properties are illustrated in an exemplary manner in Table 1; see examples.

Yet further advantages are apparent from the examples enclosed herewith.

It is understood that throughout the present specification the term "compound" encompasses pharmaceutically acceptable salts, solvates, polymorphs, prodrugs, codrugs, cocrystals, tautomers, racemates, enantiomers, or diastereomers or mixtures thereof unless mentioned otherwise.

In the compounds of formula (I), R¹ is an alkanediyl chain, preferably a C1-C6 alkanediyl chain, more preferably a C2-C3 alkanediyl chain, and most preferably a linear $C_3H_6$-moiety.

In line with the above, it is preferred that the compound of formula (I) is represented by formula (Ia):

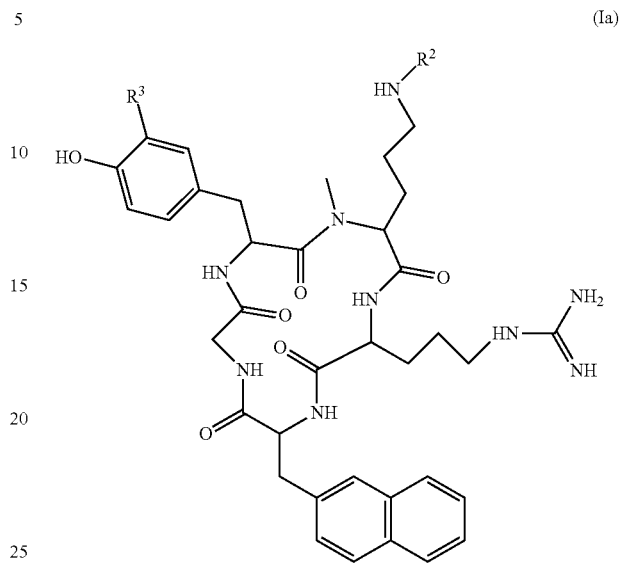

(Ia)

wherein R² and R³ are as defined herein, including their preferred embodiments.

It is further preferred that the compound of formula (I) is represented by formula (Ib):

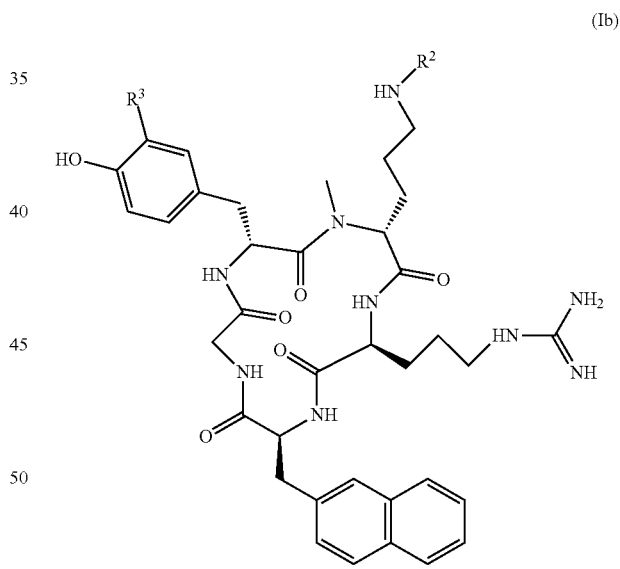

(Ib)

wherein R² and R³ are as defined herein, including their preferred embodiments.

R² in formula (I) or its preferred embodiments (Ia) and (Ib) is a group of formula (II):

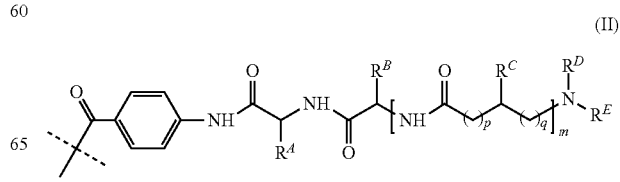

(II)

a group of formula (III):

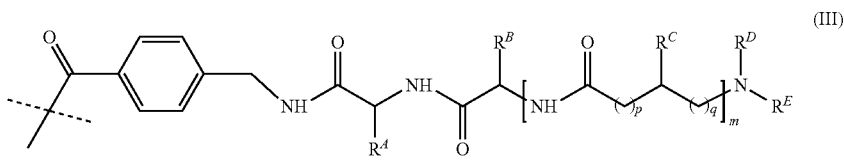

or a group of formula (IV):

(IV)

Among groups (II), (III) and (IV), preference is given to (II) in the context of the invention.

The group of formula (II), (III) or (IV) is linked to the remainder of the compound with the bond marked by the dashed line.

$R^A$ in formulae (II), (III) and (IV) is H or alkyl, preferably H or C1-C6 alkyl, more preferably H or C1-3 alkyl, most preferably H or methyl.

$R^B$ in formulae (II), (III) and (IV) is substituted alkyl, preferably substituted C1-C6 alkyl, and more preferably C1-C4 alkyl. The alkyl group is preferably a linear alkyl group. The alkyl is substituted with at least one group, such as one, two or three, selected from —$NH_2$ and the guanidino group —NH—C(=NH)—$NH_2$. It is preferred that the alkyl group $R^B$ carries one substituent selected from —$NH_2$ and the guanidino group —NH—C(=NH)—$NH_2$. More preferably, the alkyl group is a linear alkyl group having one substituent attached to the terminal carbon atom, i.e. the carbon atom most remote from the point of attachment of $R^B$ to the remainder of the groups (II), (III) or (IV). Thus, it is particularly preferred that $R^B$ is selected from a group-(linear C1-C6 alkyl)-$NH_2$ and -(linear C1-C6 alkyl)-NH—C(=NH)—$NH_2$.

$R^C$ is H or optionally substituted alkyl. The alkyl group is preferably a C1-C6 alkyl, more preferably a C1-3 alkyl, most preferably a C1 or C3 alkyl. The alkyl group is optionally substituted with one or more, such as one, two or three substituents. Preferably, the alkyl group is unsubstituted or carries one substituent. The optional substituent(s) are selected from —$NH_2$, —NH—C(=NH)—$NH_2$, —COOH, —$CONH_2$, —OH, —SH, —S—$CH_3$, and a 5- to 10-membered carbocycle or 5- to 10-membered heterocycle. The heterocycle contains oxygen, nitrogen and/or sulfur as heteroatom(s). Preferably, said carbocycle is an aryl group and said heterocycle is a heteroaryl group. $R^C$ may be further substituted with or may comprise a cytotoxic agent, such as an auristatin analogue.

p is 0, 1 or 2; q is 0, 1 or 2 and p+q is 0, 1 or 2.

m is 0 or 1, and is preferably 0. Thus, it is preferred that $R^2$ represents the following formula (IIa) or (IIIa):

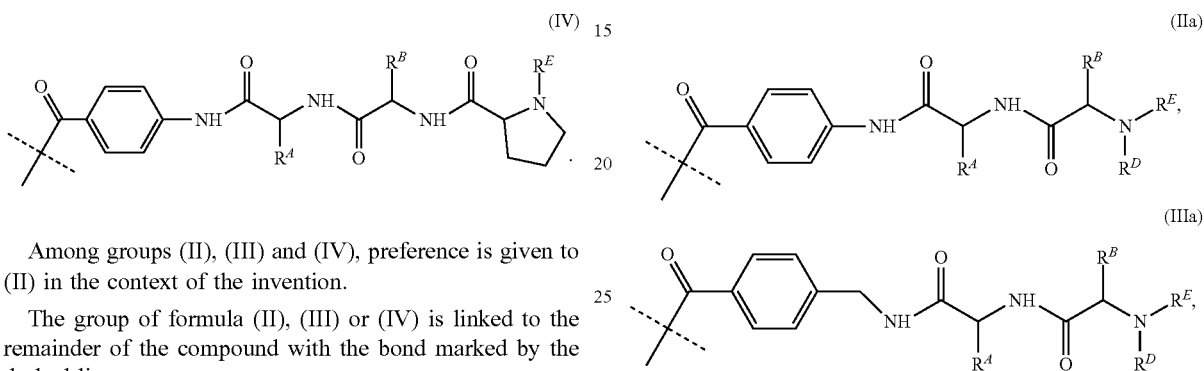

wherein $R^A$, $R^B$, $R^D$ and $R^E$ are as defined herein, including their preferred embodiments.

$R^D$ is H or forms a 5 or 6-membered heterocycle together with the adjacent nitrogen, which heterocycle also includes a part of $R^E$. The heterocycle formed by $R^D$ and a part of $R^E$ typically comprises 1, 2, or 3 heteroatoms selected from oxygen, nitrogen or sulfur, and preferably comprises 2 or 3 heteroatoms which are nitrogen atoms. Preferably, $R^D$ is H.

$R^E$ is a group which comprises at least one of the following:
(i) a chelating moiety,
(ii) a chelate formed by the chelating moiety (i) with a chelated radioactive or non-radioactive cation or anion, preferably a chelated radioactive or non-radioactive cation,
(iii) a moiety carrying a covalently bound radioisotope, or a precursor suitable to be labeled with such a radioisotope,
(iv) a cytotoxic moiety,
(v) a fluorescent moiety.

Typically, $R^E$ comprises one of the moieties (i) to (v), i.e. it is not necessary that two or more of (i) to (v) are present in one compound in accordance with the invention. Among the moieties (i) to (v), preference is given to (i), (ii) and (iii). Thus, it is particularly preferred that $R^E$ comprises one of (i), (ii) and (iii). It is still further preferred that $R^E$ comprises one of (i) and (ii).

As will be understood by the skilled reader, the above definition, according to which $R^E$ comprises at least one of the above moieties encompasses the case that $R^E$ comprises a further moiety or further moieties together with the at least one moiety of (i) to (v). In accordance with a preferred example, $R^E$ may comprise, in addition to the at least one moiety of the above (i) to (v), a linking group which attaches the at least one moiety of (i) to (v) to the remainder of the compound. The linking group may be a divalent linking group which attaches one of (i) to (v) to the remainder of the compound, or a branched linking group which allows two or more of (i) to (v) to be attached to the remainder of the compound. Preferably, if such a linking group is present, it is a divalent linking group.

Thus, in a further preferred embodiment, R² has a formula selected from formulae (IIb) and (IId), more preferably from formulae (IIc) and (IIe)

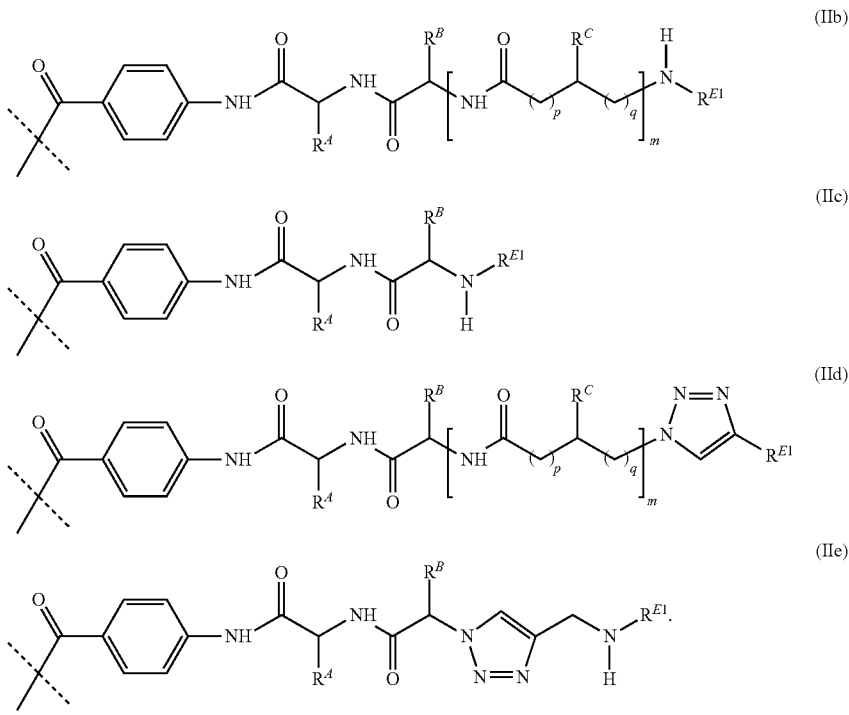

It is particularly preferred that R² represents a group of formula (IIc).

In these formulae, $R^A$, $R^B$, $R^C$, p, q and m are as defined herein, including their preferred embodiments, and $R^{E1}$ is a group which comprises one of the following or is one of the following:
(i) a chelating moiety,
(ii) a chelate formed by the chelating moiety (i) with a chelated radioactive or non-radioactive cation or anion, preferably a chelated radioactive or non-radioactive cation,
(iii) a moiety carrying a covalently bound radioisotope, preferably $^{18}$F-fluoride, or a precursor suitable to be labeled with such a radioisotope,
(iv) a cytotoxic moiety,
(v) a fluorescent moiety.

Also for $R^{E1}$, preference is given to (i), (ii) and (iii) among (i) to (v). Thus, it is particularly preferred that $R^{E1}$ comprises one of (i), (ii) and (iii) or is one of (i), (ii) and (iii). It is still further preferred that $R^{E1}$ comprises one of (i) and (ii). Also for $R^{E1}$, the above definition according to which $R^{E1}$ comprises one of the above moieties encompasses the case that $R^{E1}$ comprises a further moiety or further moieties together with the one moiety of (i) to (v), such as an additional linking group which binds the one moiety of (i) to (v) to the remainder of the compound.

The chelating moiety of (i) and (ii), both in the context of the definition of $R^E$ and $R^{E1}$, is suitable to form a chelate with a radioactive or non-radioactive cation or anion, preferably a radioactive or non-radioactive cation. Suitable chelating moieties for diverse cations and anions are well known in the art, and can be used in the context of the present invention.

Preferably, the chelating moiety comprises at least one of
a macrocyclic ring structure with 8 to 20 ring atoms of which 2 or more, preferably 3 or more, are selected from oxygen atoms, sulfur atoms and nitrogen atoms; and
an acyclic, open chain chelating structure with 8 to 20 main chain atoms of which 2 or more, preferably 3 or more are heteroatoms selected from oxygen atoms, sulfur atoms and nitrogen atoms.

A preferred example for the chelating moiety is a residue of a chelating agent such as bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecane (DO2A), 1,4,7,10-tetraazacyclododecane-N,N',N'',N'''-tetraacetic acid (DOTA), α-(2-carboxyethyl)-1,4,7,10-tetraazacyclododecane-1,4,7,10-tetraacetic acid or 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphate) (DPDP), diethylenetriaminepentaacetic acid (DTPA), ethylenediamine-N,N'-tetraacetic acid (EDTA), ethyleneglycol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecane-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneaminetetraacetic acid (TMT), 1,4,7,10-tetraazacyclotridecan-N,N',N",N'''-tetraacetic acid (TRITA), triethylenetetraaminehexaacetic acid (TTHA), N,N'-bis[(6-carboxy-2-pyridyl)methyl]-4,13-diaza-18-crown-6 (H$_2$macropa), and 4-amino-4-{2-[(3-hydroxy-1,6-dimethyl-4-oxo-1,4-dihydro-pyridin-2-ylmethyl)-carbamoyl]-ethyl} heptanedioic acid bis-[(3-hydroxy-1,6-dimethyl-4-oxo-1,4-dihydro-pyridin-2-ylmethyl)-amide] (THP), which residue is obtainable by covalently binding a carboxyl group contained in the chelating agent to the remainder of the compound via an ester or an amide bond, preferably an amide bond. For example, in formulae (II), (III), (IV), (IIa), (IIIa), (IIb), (IIc) and (IIe), an amide bond can be conveniently formed directly from a carboxyl group contained in the above exemplary chelating agents and the nitrogen atom to which $R^E$ or $R^{E1}$, respectively, is attached in these formulae.

In a more preferred example, the chelating moiety is a residue of a chelating agent is selected from DOTA and DOTAGA, still more preferably a residue obtainable by forming an amide bond from a carboxyl group contained in DOTA and DOTAGA, and the nitrogen atom to which $R^E$ or $R^{E1}$, respectively, is attached in formulae (II), (III), (IV), (IIa), (IIIa), (IIb), (IIc) or (IIe).

Exemplary radioactive cations that are optionally chelated by the chelating moiety in accordance with (ii) are selected from the cations of $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{21}$At, $^{212}$Bi, $^{213}$Bi, $^{223}$Ra, $^{225}$Ac, and $^{227}$Th, or a cationic molecule comprising $^{18}$F, such as $^{18}$F-[AlF]$^{2+}$.

Preferred chelated cations are selected from the cations of $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th, or a cationic molecule comprising $^{18}$F. Even further preferred are cations of $^{68}$Ga, $^{90}$Y, $^{177}$Lu, $^{212}$Bi, and $^{213}$Bi.

Moieties (iii) carrying a covalently bound radioisotope, preferably $^{18}$F-fluoride, or precursors suitable to be labeled with such radioisotope as referred to in the definition of $R^E$ and $R^{E1}$ are also known in the art. As examples of such a precursor, reference can be made to a group of formula —N$^+$(CH$_3$)$_2$—CH$_2$—BF$_3^-$ and to a group of the formula —Ar—SiF(C(CH$_3$)$_3$)$_2$, wherein Ar is a divalent aromatic group, preferably a phenylene group. As will be appreciated by the skilled reader, such a group of the formula —Ar—SiF(C(CH$_3$)$_3$)$_2$ can be conveniently bound to the remainder of the compounds in accordance with the invention by a functional group which may be attached to Ar at the open valence as indicated in the formula, and which is suitable for covalent coupling of the group —Ar—SiF(C(CH$_3$)$_3$)$_2$. For example, reference can be made to an amide bond or an ester bond which can be formed e.g. if the group —Ar—SiF(C(CH$_3$)$_3$)$_2$ is provided as a part of a benzoic acid derivative of the formula —C(O)—C6H4-SiF(C(CH$_3$)$_3$)$_2$.

The cytotoxic moiety as moiety (iv) may be provided, for example, by an auristatin analogue, such as monomethyl auristatin E (MMAE), monomethyl auristatin F (MMAF), PF-06380101 with or without a metabolically cleavable linker.

Fluorescent moieties (v) are also known in the art as fluorescent dyes which may be covalently bound as marker moieties to a compound. Examples of such dyes which may be covalently bound as or within $R^E$ or $R^{E1}$ to the remainder of the compound are Cy5- and Cy7-based cyanine dyes.

In line with the above, it is particularly preferred that $R^2$ has a formula selected from formulae (IIf) to (IIh):

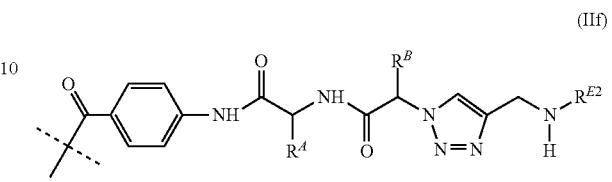
(IIf)

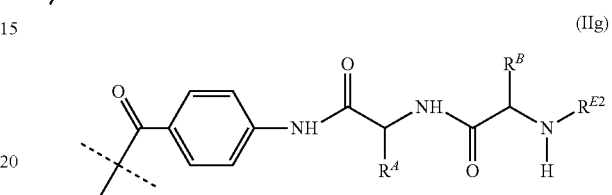
(IIg)

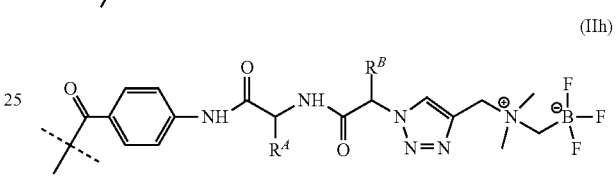
(IIh)

wherein $R^A$, $R^B$, are as defined herein, including their preferred embodiments, and $R^{E2}$ is a chelating moiety (i) represented by a residue of a chelating agent comprising a carboxyl group, said residue being provided by forming an amide bond from the carboxyl group of the chelating agent and the nitrogen atom to which $R^{E2}$ is attached. Preferred chelating agents comprising a carboxyl group are as listed above, and particularly preferred are DOTA and DOTAGA.

In a further preferred embodiment, $R^{E2}$ is (ii) a chelate formed by a residue of a chelating agent comprising a carboxyl group with a chelated radioactive cation, said residue being obtainable by forming an amide bond from the carboxyl group of the chelating agent and the nitrogen atom to which $R^{E2}$ is attached. Preferred chelating agents comprising a carboxyl group are as listed above, and particularly preferred are DOTA and DOTAGA. A preferred cation is selected from a cation of $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu $^{66}$Ga, $^{68}$Ga, $^{67}$Ga, $^{89}$Zr, $^{90}$Y $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm $^{151}$Pm $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{13}$Bi $^{223}$Ra, $^{225}$Ac, and $^{227}$Th, or a cationic molecule comprising $^{18}$F, such as $^{18}$F-[AlF]$^{2+}$.

It is still more preferred that the radioactive cation is selected from a cation of $^{99m}$Tc, $^{186}$Re, $^{188}$Re, $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu $^{188}$Re, $^{212}$Pb, $^{212}$Bi, $^{213}$Bi, $^{225}$Ac, and $^{227}$Th or a cationic molecule comprising $^{18}$F. Even further preferred are cations of $^{68}$Ga, $^{90}$Y $^{177}$Lu, $^{212}$Bi, and $^{213}$Bi.

In a further preferred embodiment, said compound or salt binds human CXCR4 with an IC$_{50}$ of less or equal 100 nM, preferably less or equal 20 nM, most preferably less or equal 5 nM.

In a second aspect, the invention provides a pharmaceutical composition comprising or consisting of a compound or salt in accordance with the first aspect.

In a third aspect, the invention provides a diagnostic or therapeutic composition comprising or consisting of a compound or salt in accordance with the first aspect.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in the pancreas or into a brain artery or directly into brain tissue. The compositions may also be administered directly to the target site, e.g., by biolistic delivery to an external or internal target site, like the pancreas or brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Pharmaceutically active matter may be present in amounts between 0,1 ng and 10 mg/kg body weight per dose; however, doses below or above this exemplary range are envisioned, especially considering the aforementioned factors.

The above applies mutatis mutandis also to diagnostic compositions.

To the extent the above disclosed pharmaceutical composition, diagnostic composition and therapeutic composition comprises one or more compounds of the invention, it is preferred that no further pharmaceutically active compounds, diagnostically active compounds or therapeutically active compounds are present. In the alternative, further therapeutically active, diagnostically active or pharmaceutically active compounds may be present, for example, anticancer agents.

In a fourth aspect, the invention provides a compound or salt in accordance with the first aspect for use in medicine, preferably in nuclear medicine, for nuclear molecular imaging, or optical imaging, or targeted endoradiotherapy.

In a fifth aspect, the invention provides a compound or salt in accordance with the first aspect for use in a method of treating or preventing diseases that are associated with increased expression of chemokine receptors subtype 4 (CXCR4), such as cancer and lymphoproliferative diseases, as well as cardiovascular diseases, AIDS and inflammatory disorders.

In a sixth aspect, the invention provides a compound or salt in accordance with the first aspect for use in a method of diagnosing and/or staging cancer.

In a seventh aspect, the invention provides the use of a linker having a structure of formula (Va) or (Vb), (VIa) or (VIb):

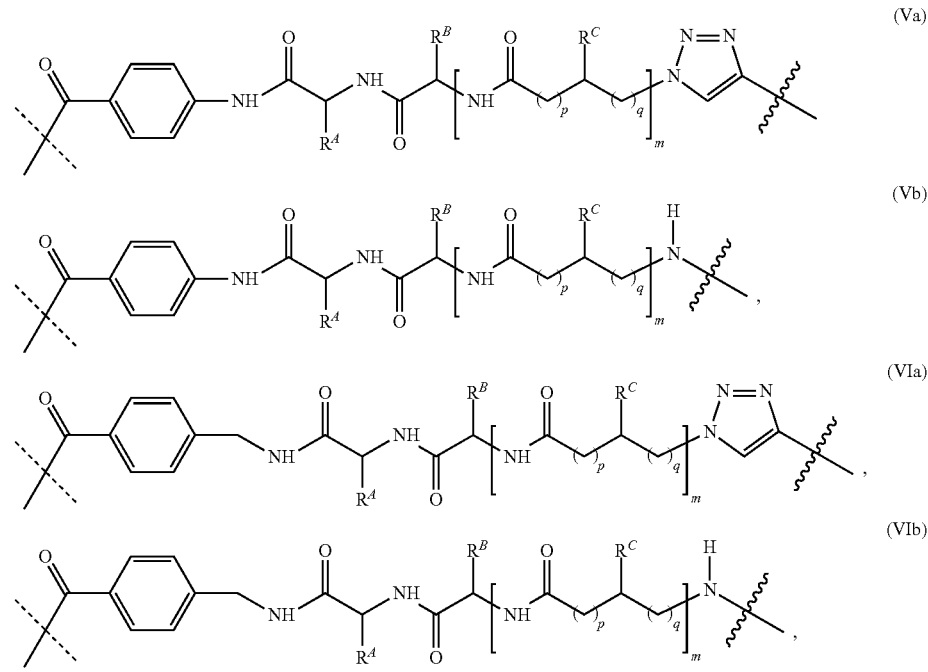

to connect a CXCR4 binding agent to a group comprising at least one of the following:

(i) a chelating moiety, (ii) a chelate formed by a chelating moiety with a chelated radioactive or non-radioactive cation or anion, preferably a chelated radioactive or non-radioactive cation, (iii) a moiety carrying a covalently bound radioisotope, preferably $^{18}$F-fluoride, or a precursor suitable to be labeled with such a radioisotope, (iv) a cytotoxic moiety, such as an auristatin analogue,
(v) a fluorescent moiety (a dye), such as e.g. Cy5 or Cy7,
wherein $R^A$, $R^B$, $R^C$, p, q and m are as defined above, including their preferred embodiments.

It will be understood that also the definitions and preferred definitions for the moieties (i) to (v) provided above for the compounds in accordance with the invention apply in this context.

The term "CXCR4 binding agent" refers to any agent which is capable of binding to the chemokine receptor 4 (CXCR4), preferably with an affinity of $IC_{50}$ of 1 μM or stronger, 500 nM or stronger, 100 nM or stronger, 50 nM or stronger, or 20 nM or stronger. Means and methods for determining receptor—binding agent affinities are known in the art and incude e.g. surface plasmon resonance. In structural terms, the CXCR4 binding agent is not particularly limited. Preferred embodiments include (i) the natural ligand (CXCL12) and (ii) compounds which differ from compounds of formula (I) of this invention in that $R^2$ is replaced with H.

Uses in accordance with the seventh aspect include (a) reacting a CXCR4 binding agent or a chemically activated form thereof with a linker having a structure of formula (Va), (Vb), (VIa) or (VIb), such that a first covalent bond is formed between said CXCR4 binding agent and said linker, wherein the dashed line in formulae (Va), (Vb), (VIa) and (VIb) indicates the free valence which is converted into said first covalent bond, and (b) reacting a group comprising at least one of items (i) to (v) in accordance with the seventh aspect or a chemically activated form thereof with said linker such that a second covalent bond is formed between said group and said linker, wherein the wavy line in formulae (Va), (Vb), (VIa) and (VIb) indicates the free valence which is converted into said second covalent bond.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, l; A, F, G; A, F, H; A, F, I; B, D, G; B, D, H; B, D, l; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed. This applies likewise for the following items.

In particular, the invention includes the following items:
1. A compound of the following formula (I)

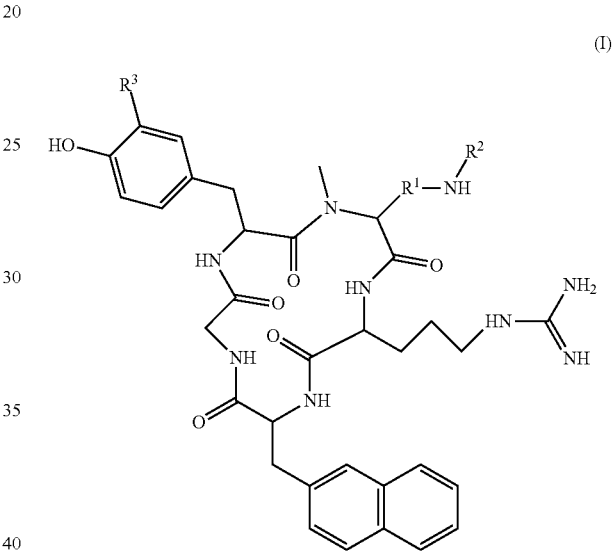

or a pharmaceutically acceptable salt thereof, wherein:
$R^1$ is an alkanediyl chain, preferably a C1-C6 alkanediyl chain, more preferably a C2-C3 alkanediyl chain, and most preferably a linear $C_3H_6$-moiety;
$R^2$ is a group of formula (II):

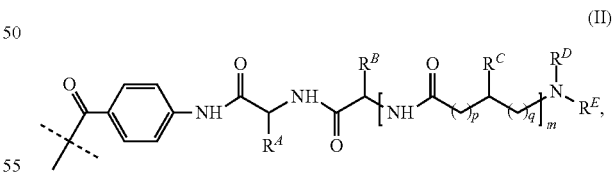

of formula (III):

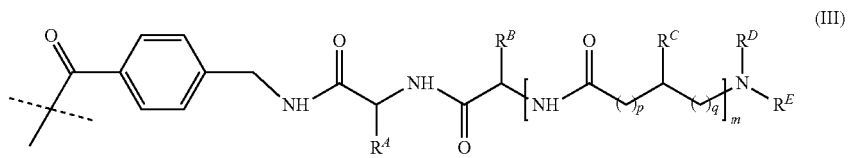

or of formula (IV):

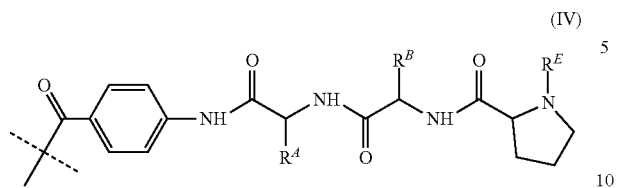

which is linked to the remainder of the compound with the bond marked by the dashed line, and wherein $R^A$ is H or alkyl, preferably H or C1-C6 alkyl, more preferably H or C1-3 alkyl, most preferably H or methyl;

$R^B$ is substituted alkyl, preferably substituted C1-C6 alkyl, which substituted alkyl is substituted with at least one group selected from —$NH_2$ and the guanidino group —NH—C(=NH)—$NH_2$;

$R^C$ is H or optionally substituted alkyl, alkyl preferably being C1-C6 alkyl, more preferably C1-3 alkyl, most preferably C1 or C3 alkyl, with one or more optional substituents being selected from —$NH_2$, —NH—C(=NH)—$NH_2$, —COOH, —$CONH_2$, —OH, —SH, —S—$CH_3$, and 5- to 10-membered carbocycle or 5- to 10-membered heterocycle containing oxygen, nitrogen and/or sulfur as heteroatom(s), said carbocycle or heterocycle preferably being aryl or heteroaryl, wherein $R^C$ may be further substituted with or may comprise a cytotoxic agent, such as an auristatin analogue;

p is 0, 1 or 2;

q is 0, 1 or 2;

p+q is 0, 1 or 2;

m is 0 or 1, preferably 0;

$R^D$ is H or forms a 5 or 6-membered heterocycle together with the adjacent nitrogen which heterocycle also includes a part of $R^E$;

$R^E$ is a group which comprises at least one of the following:

(i) a chelating moiety, (ii) a chelate formed by a chelating moiety (i) with a chelated radioactive or non-radioactive cation or anion, preferably a chelated radioactive or non-radioactive cation, (iii) a moiety carrying a covalently bound radioisotope, preferably $^{18}$F-fluoride, or a precursor suitable to be labeled with such radioisotopes;

(iv) a cytotoxic moiety, such as an auristatin analogue, (v) a fluorescent group (a dye), such as e.g. Cy5 or Cy7; and $R^3$ is H or 1.

2. The compound or salt of item 1, wherein the compound has the formula (Ia):

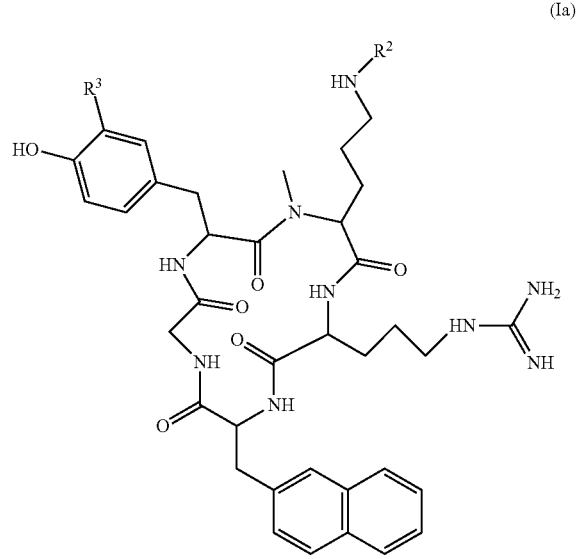

and wherein $R^2$ and $R^3$ are defined as in item 1.

3. The compound or salt of item 2, wherein the compound has the formula (Ib):

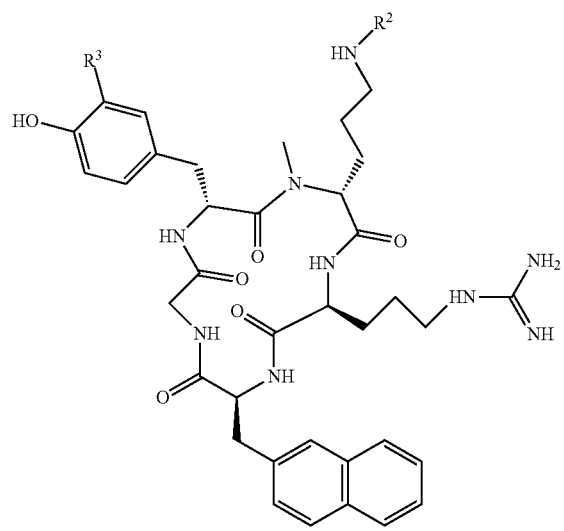

and wherein $R^2$ and $R^3$ are defined as in item 1.

4. The compound or salt of any of items 1 to 4, wherein $R^B$ is substituted linear C1-C6 alkyl, more preferably substituted linear C1-C4 alkyl which is substituted at its terminal carbon with one group selected from —$NH_2$ and —NH—C(=NH)—$NH_2$.

5. The compound or salt of any of items 1 to 4, wherein $R^2$ has the formula (IIa) or (IIIa)

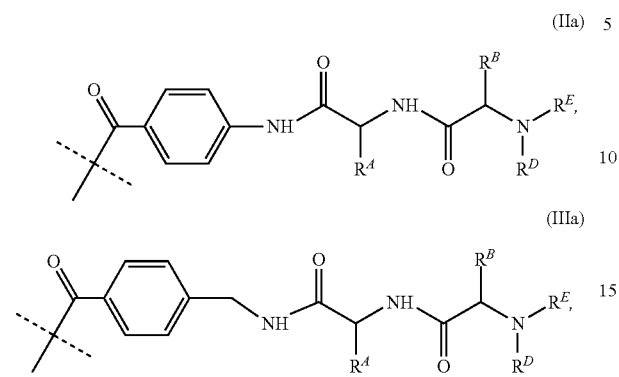

(IIa)

(IIIa)

wherein $R^A$, $R^B$, $R^D$ and $R^E$ are defined as in item 1 or 4.

6. The compound or salt of any of items 1 to 4, wherein $R^2$ has a formula selected from formulae (IIb) and (IId):

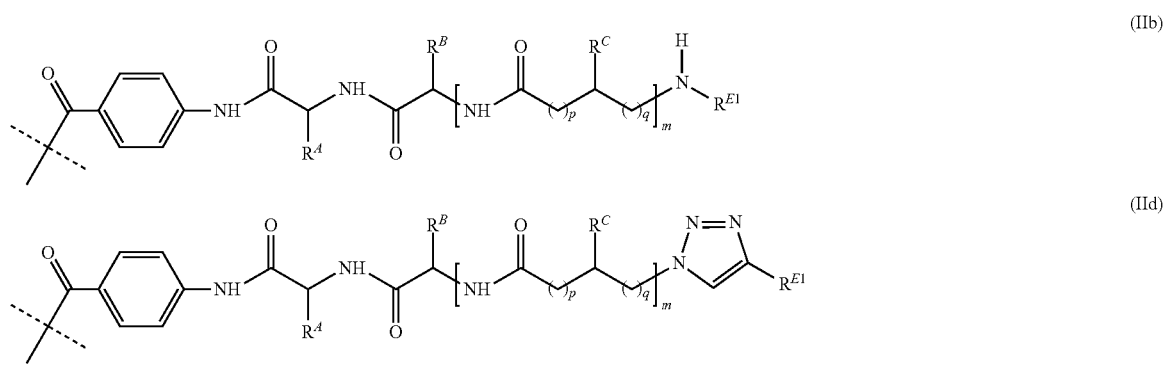

(IIb)

(IId)

wherein
$R^A$, $R^B$, $R^C$, p, q and m are defined as in item 1 or 4, and $R^{E1}$ is a group which comprises at least one of the following:
(i) a chelating moiety,
(ii) a chelate formed by a chelating moiety (i) with a chelated radioactive or non-radioactive cation or anion, preferably a chelated radioactive or non-radioactive cation,
(iii) a moiety carrying a covalently bound radioisotope, preferably $^{18}$F-fluoride, or a precursor suitable to be labeled with such a radioisotope,
(iv) a cytotoxic moiety, such as e.g. auristatin analogues,
(v) a fluorescent group (a dye), such as Cy5 or Cy7.

7. The compound or salt of item 6, wherein $R^2$ has a formula selected from formulae (IIc) and (IIe):

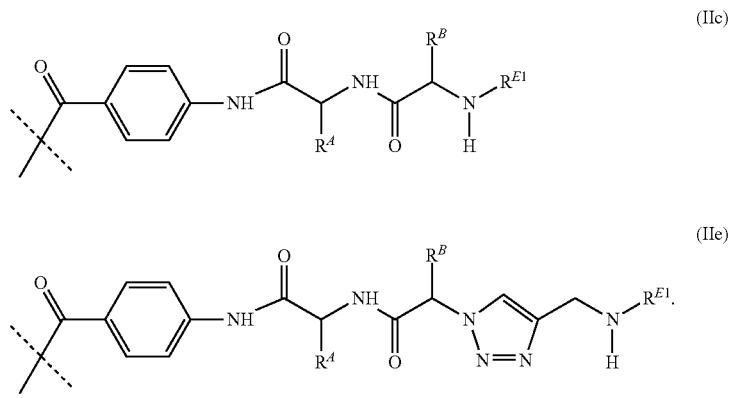

(IIc)

(IIe)

wherein
$R^A$, $R^B$ and $R^{E1}$ are defined as in item 6.
8. The compound or salt of any of items 1 to 7, wherein $R^E$ or $R^{E1}$, respectively, is selected from (i) a group which comprises a chelating moiety, and (ii) a chelate formed by a chelating moiety (i) with a chelated radioactive or non-radioactive cation, and wherein the chelating moiety comprises at least one of
a macrocyclic ring structure with 8 to 20 ring atoms of which 2 or more, preferably 3 or more, are selected from oxygen atoms, sulfur atoms and nitrogen atoms; and
an acyclic, open chain chelating structure with 8 to 20 main chain atoms of which 2 or more, preferably 3 or more are heteroatoms selected from oxygen atoms, sulfur atoms and nitrogen atoms.
9. The compound or salt of any of items 1 to 7, wherein the chelating moiety is a residue derived from a chelating agent selected from bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecane (DO2A), 1,4,7,10-tetraazacyclododecane-N,N',N'',N'''-tetraacetic acid (DOTA), α-(2-carboxyethyl)-1,4,7,10-tetraazacyclododecane-1,4,7,10-tetraacetic acid or 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphat) (DPDP), diethylenetriaminepentaacetic acid (DTPA), ethylenediamine-N,N'-tetraacetic acid (EDTA), ethyleneglycol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclododecane-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneamintetraacetic acid (TMT), 1,4,7,10-tetraazacyclotridecan-N,N',N'',N'''-tetraacetic acid (TRITA), triethylenetetraaminehexaacetic acid (TTHA), N,N'-bis[(6-carboxy-2-pyridyl)methyl]-4,13-diaza-18-crown-6 ($H_2$macropa), and 4-amino-4-{2-[(3-hydroxy-1,6-dimethyl-4-oxo-1,4-dihydro-pyridin-2-ylmethyl)-carbamoyl]-ethyl} heptanedioic acid bis-[(3-hydroxy-1,6-dimethyl-4-oxo-1,4-dihydro-pyridin-2-ylmethyl)-amide] (THP), which residue is obtainable by covalently binding a carboxyl group contained in the chelating agent to the remainder of the compound via an ester or an amide bond, preferably an amide bond.
10. The compound or salt of item 9, wherein the chelating agent is selected from DOTA and DOTAGA.
11. The compound or salt of any of items 1 to 10, wherein $R^E$ or $R^{E1}$, respectively, is a group which comprises a chelate formed by a chelating moiety with a chelated radioactive cation selected from a cation of 44Sc, $^{47}$Sc, $^{51}$Cr, $^{52m}$Mn, $^{58}$Co, $^{52}$Fe, $^{56}$Ni, $^{57}$Ni, $^{62}$Cu, 64Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$Ac, and $^{227}$Th, or a cationic molecule comprising $^{18}$F, such as $^{18}$F-[AlF]$^{2+}$.
12. The compound or salt of item 11, wherein the radioactive cation is selected from a cation of $^{99m}$Tc, $^{186}$Re, $^{188}$Re, $^{44}$Sc, $^{47}$Sc, $^{64}$Cu, $^{67}$Cu, $^{68}$Ga, $^{90}$Y, $^{111}$In $^{161}$Tb, $^{166}$Ho, $^{177}$Lu, $^{188}$Re, $^{212}$Pb, $^{212}$Bi, $^{213}$Bi, $^{225}$Ac, and $^{227}$Th or a cationic molecule comprising $^{18}$F.
13. The compound or salt of any of items 1 to 4, wherein $R^2$ has a formula selected from formulae (IIf) to (IIh):

(IIf)
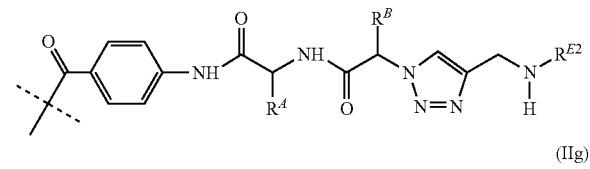

(IIg)
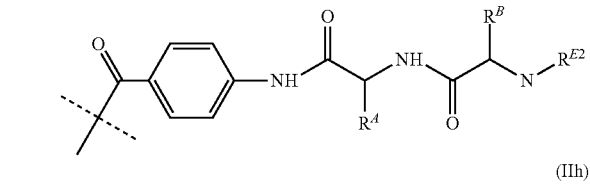

(IIh)
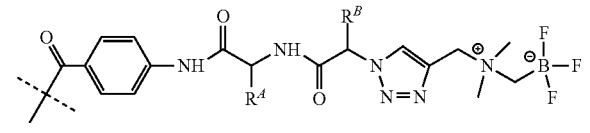

wherein
$R^A$, $R^B$, are defined as in item 1 or 4, and
$R^{E2}$ is selected from (i) a residue of a chelating agent comprising a carboxyl group and (ii) a chelate formed by a residue of a chelating agent comprising a carboxyl group with a chelated radioactive or non-radioactive cation or anion, preferably a chelated radioactive or non-radioactive cation,
said residue being obtainable by forming an amide bond from the carboxyl group of the chelating agent and the nitrogen atom to which $R^{E2}$ is attached.
14. The compound or salt of any of item 13, wherein the chelating agent comprising a carboxyl group is selected from bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2]hexadecane (DO2A), 1,4,7,10-tetraazacyclododecane-N,N',N'',N'''-tetraacetic acid (DOTA), α-(2-carboxyethyl)-1,4,7,10-tetraazacyclododecane-1,4,7,10-tetraacetic acid or 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphat) (DPDP), diethylenetriaminepentaacetic acid (DTPA), ethylenediamine-N,N'-tetraacetic acid (EDTA), ethyleneglycol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis (methyleneamintetraacetic acid (TMT), 1,4,7,10-tetraazacyclotridecan-N,N',N",N"-tetraacetic acid (TRITA), triethylenetetraaminehexaacetic acid (TTHA), N,N'-bis[(6-carboxy-2-pyridyl)methyl]-4,13-diaza-18-crown-6 ($H_2$macropa), and 4-amino-4-{2-[(3-hydroxy-1,6-dimethyl-4-oxo-1,4-dihydro-pyridin-2-ylmethyl)-carbamoyl]-ethyl} heptanedioic acid bis-[(3-hydroxy-1,6-dimethyl-4-oxo-1,4-dihydro-pyridin-2-ylmethyl)-amide] (THP).

15. The compound or salt of item 14, wherein the chelating agent is selected from DOTA and DOTAGA.
16. The compound or salt of any of items 13 to 15, wherein $R^{E2}$ is a chelate formed by a residue of a chelating agent comprising a carboxyl group with a chelated radioactive cation selected from a cation of $^{44}$Sc, $^{47}$Sc, $^{51}$Cr, $^{52m}$Mn, $^{58}$Co, $^{52}$Fe, $^{5M}$Ni, $^{57}$Ni, $^{62}$Cu, $^{64}$Cu $^{67}$Cu $^{66}$Ga, $^{68}$Ga, $^{67}$Ga, $^{89}$Zr, $^{90}$Y, $^{89}$Y, $^{94m}$Tc, $^{99m}$Tc $^{97}$Ru, $^{105}$Rh, $^{109}$Pd, $^{111}$Ag, $^{110m}$In, $^{111}$In, $^{113m}$In, $^{114m}$In, $^{117m}$Sn $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$Ac, and $^{227}$Th, or a cationic molecule comprising $^{18}$F, such as $^{18}$F-[AlF]$^{2+}$.
17. The compound or salt of item 16, wherein the radioactive cation is selected from a cation of $^{99m}$Tc, $^{186}$Re $^{188}$Re, $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th or a cationic molecule comprising $^{18}$F.
18. A compound or salt of any one of items 1 to 17, wherein said compound or salt binds human CXCR4 with an $IC_{50}$ of less or equal 100 nM, preferably less or equal 20 nM, most preferably less or equal 5 nM.
19. A pharmaceutical composition comprising or consisting of a compound or salt of any one of items 1 to 18.
20. A diagnostic composition comprising or consisting of a compound or salt of any one of items 1 to 18.
21. A compound or salt of any one of items 1 to 18 for use in medicine, preferably in nuclear medicine, for nuclear molecular imaging, or optical imaging, or targeted endoradiotherapy.
22. A compound or salt of any one of items 1 to 18 for use in a method of treating or preventing cancer, cardiovascular diseases, AIDS or inflammatory disorders.
23. A compound or salt of any one of items 1 to 18 for use in a method of diagnosing and/or staging cancer.
24. Use of a linker having a structure of formula (Va), (Vb), (VIa) or (VIb):

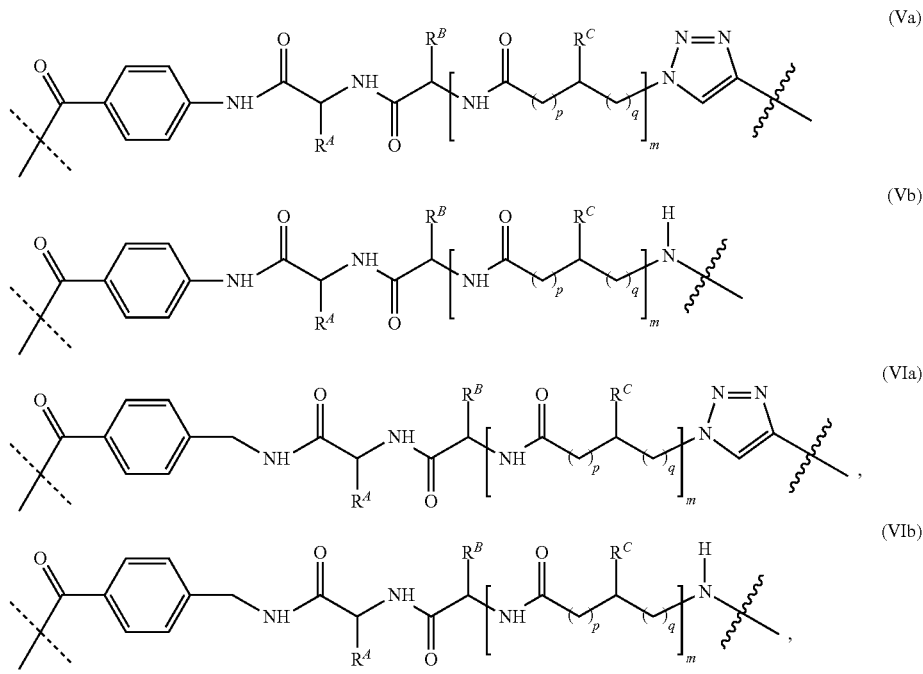

to connect a CXCR4 binding agent to a group comprising at least one of the following:
(i) a chelating moiety,
(ii) a chelate formed by a chelating moiety with a chelated radioactive or non-radioactive cation or anion, preferably a chelated radioactive or non-radioactive cation,
(iii) a moiety carrying a covalently bound radioisotope, preferably $^{18}$F-fluoride, or a precursor suitable to be labeled with such a radioisotope,
(iv) a cytotoxic agent, such as an auristatin analogue,
(v) a fluorescent moiety (a dye), such as e.g. Cy5 or Cy7, wherein $R^A$, $R^B$, $R^C$, p, q and m are defined as in item 1 or 4.

The figures show.
FIG. 1: Structures of selected CXCR4 ligands. The synthetic basis and cyclic binding scaffold CPCR4 (1). FC131

(2) was employed as the radioligand in in vitro assays. 3 and 4 are previously reported CXCR4 ligands for $^{68}$Ga labeling (pentixafor (3) and $^{177}$Lu/$^{90}$Y ERT (pentixather (4)) and were included in this study as references (Wester et al. Disclosing the CXCR4 expression in lymphoproliferative diseases by targeted molecular imaging. *Theranostics*. 2015; 5:618; Schottelius et al. [177] Lu-pentixather: preclinical and first patient results with a highly promising CXCR4-directed endoradiotherapeutic agent. *Journal of Nuclear Medicine*. 2015; 56:339-339; Herrmann et al. First-in-man experience of CXCR4-directed endoradiotherapy with 177Lu- and 90Y-labelled pentixather in advanced stage multiple myeloma with extensive intra- and extramedullary disease. *Journal of Nuclear Medicine*. 2015:jnumed. 115.167361). Structural modifications on the scaffold for 5-16 are listed in Table 1.

Figure 2:
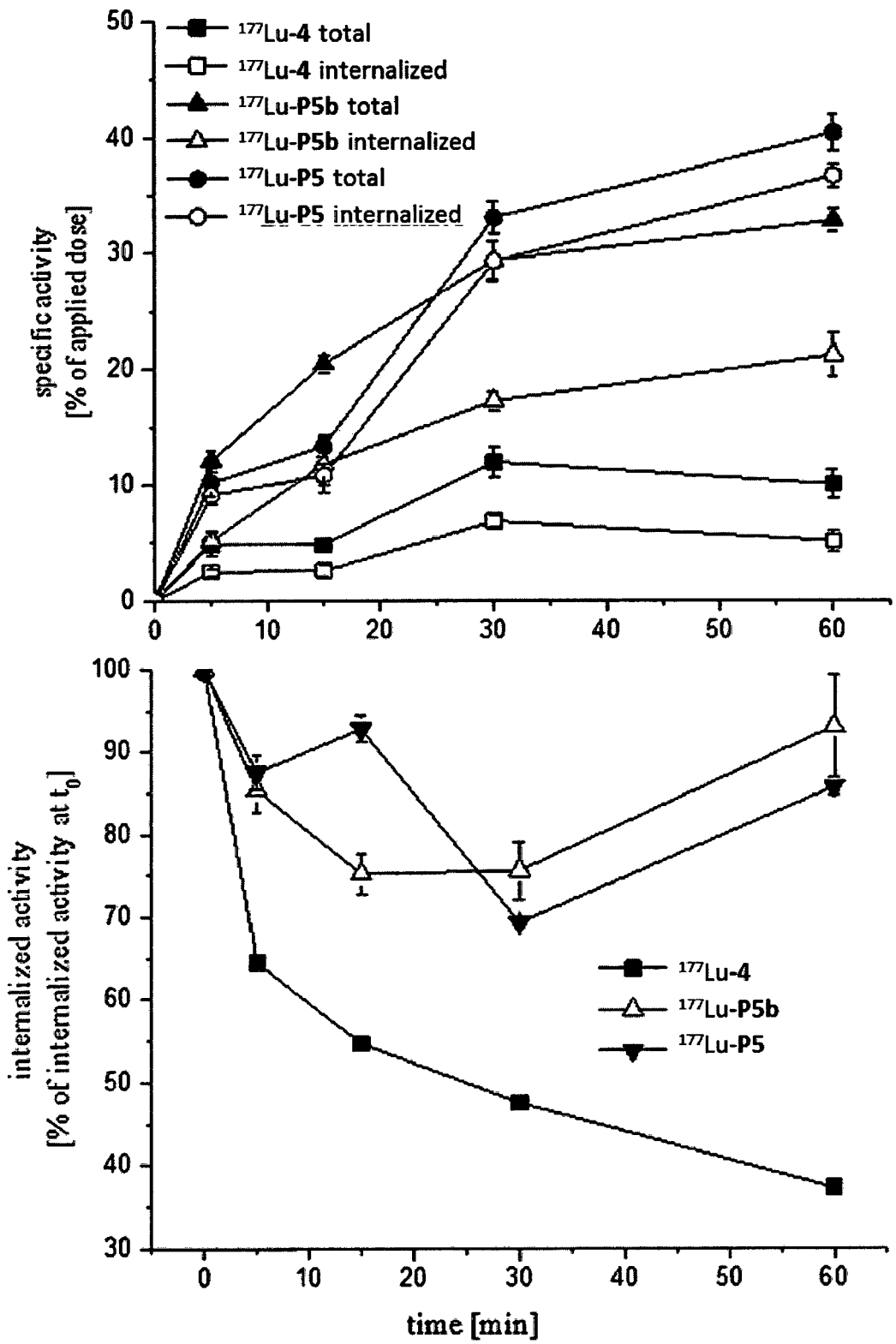

FIG. 2: Internalization kinetics of $^{177}$Lu-15 and $^{177}$Lu-16 in CXCR4$^+$ Chem_1 cells in comparison to $^{177}$Lu-4 (upper) and externalization kinetics of $^{177}$Lu-15 and $^{177}$Lu-16 in CXCR4$^+$ Chem_1 cells in comparison to $^{177}$Lu-4 (lower). All data are expressed as mean±SD (n=3).

Figure 3:
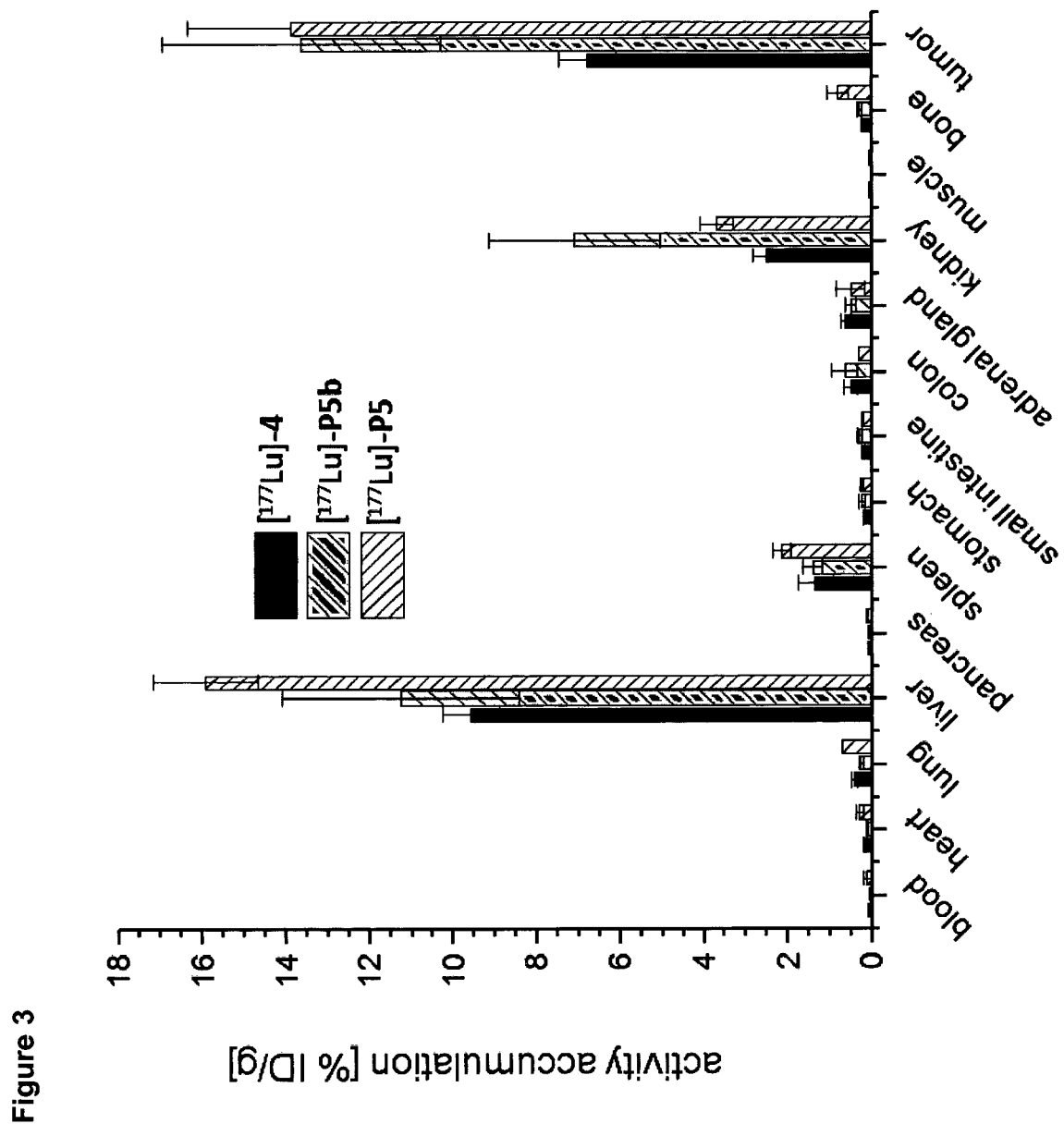

FIG. 3: Biodistribution data (in % ID/g) at 6 h p.i. The biodistribution of $^{177}$Lu-15 and $^{177}$Lu-16 in Daudi tumor xenograft bearing SCID mice (n=4) in comparison to $^{177}$Lu-4 (n=4).

Figure 4:
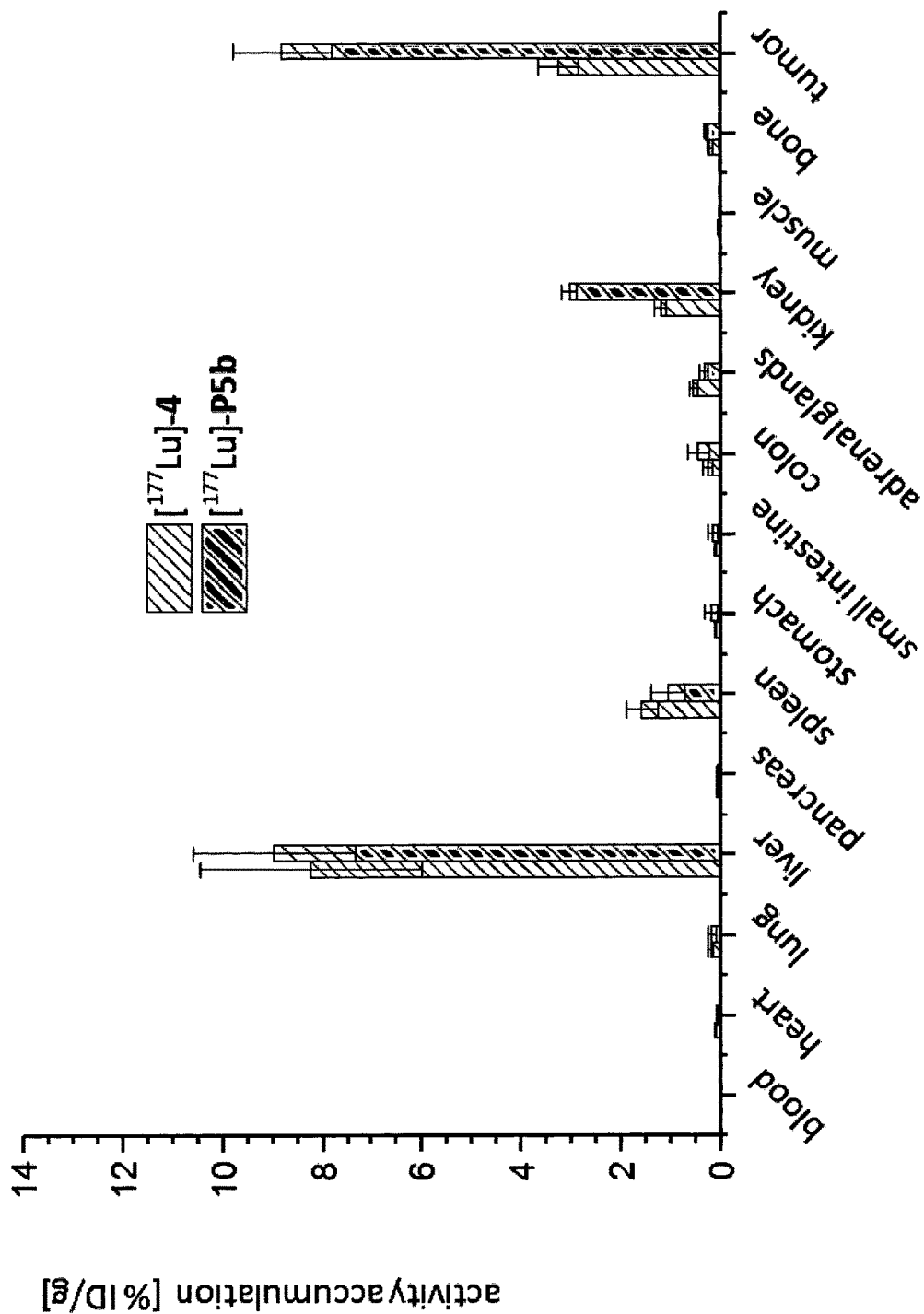

FIG. 4: Biodistribution data (in % ID/g) at 48 h p.i. The biodistribution of $^{177}$Lu-15 and $^{177}$Lu-16 in Daudi tumor xenograft bearing SCID mice (n=4) in comparison to $^{177}$Lu-4 (n=4).

Figure 5:
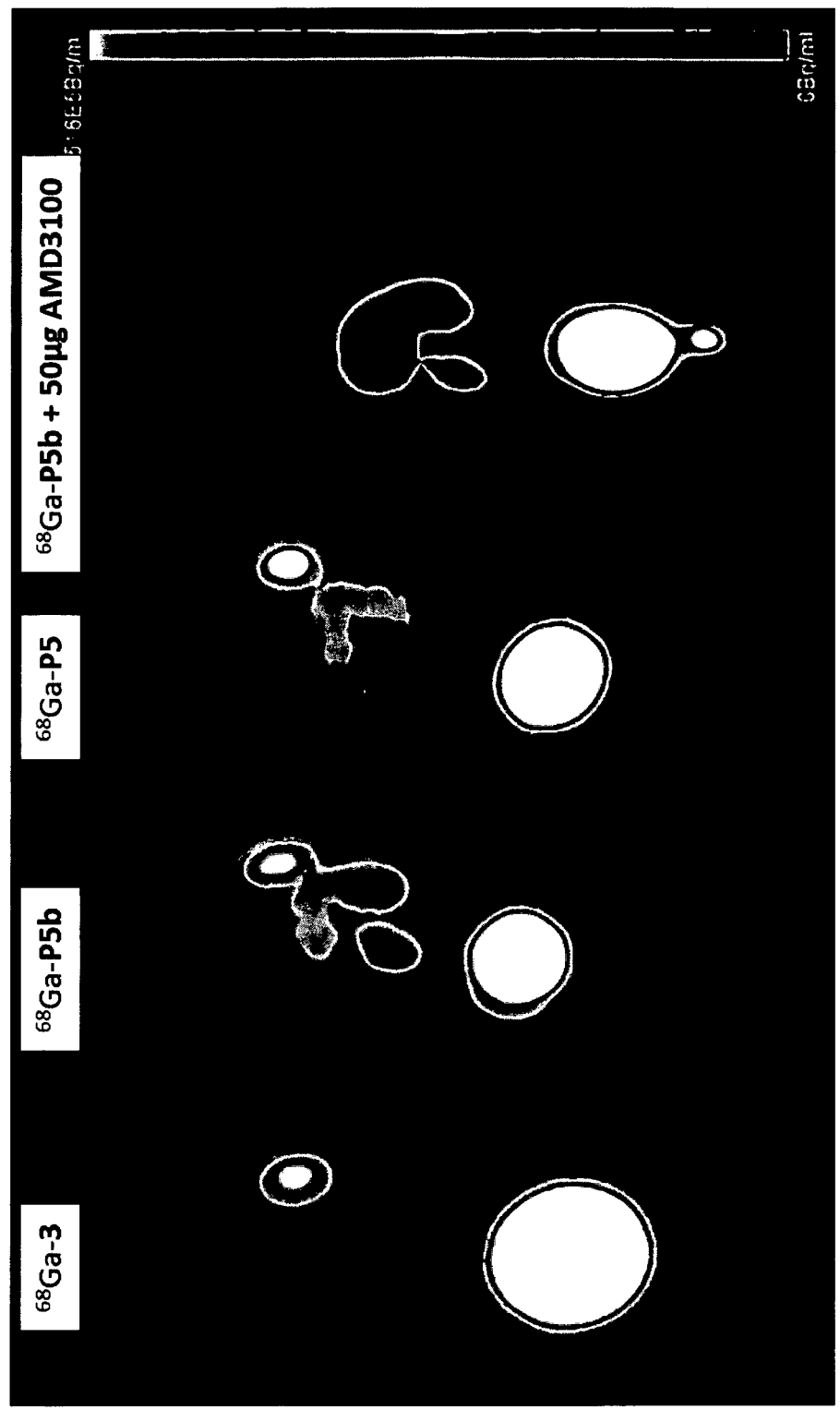

FIG. 5: Maximum intensity projections (MIP, 0 to 12% ID/mL) of static PET scans of Daudi lymphoma-bearing SCID mice, 1 h after injection using $^{68}$Ga-3, $^{68}$Ga-15, $^{68}$Ga-16 and $^{68}$Ga-15 coinjected with AMD3100 (2 mg/kg).

Figure 6:
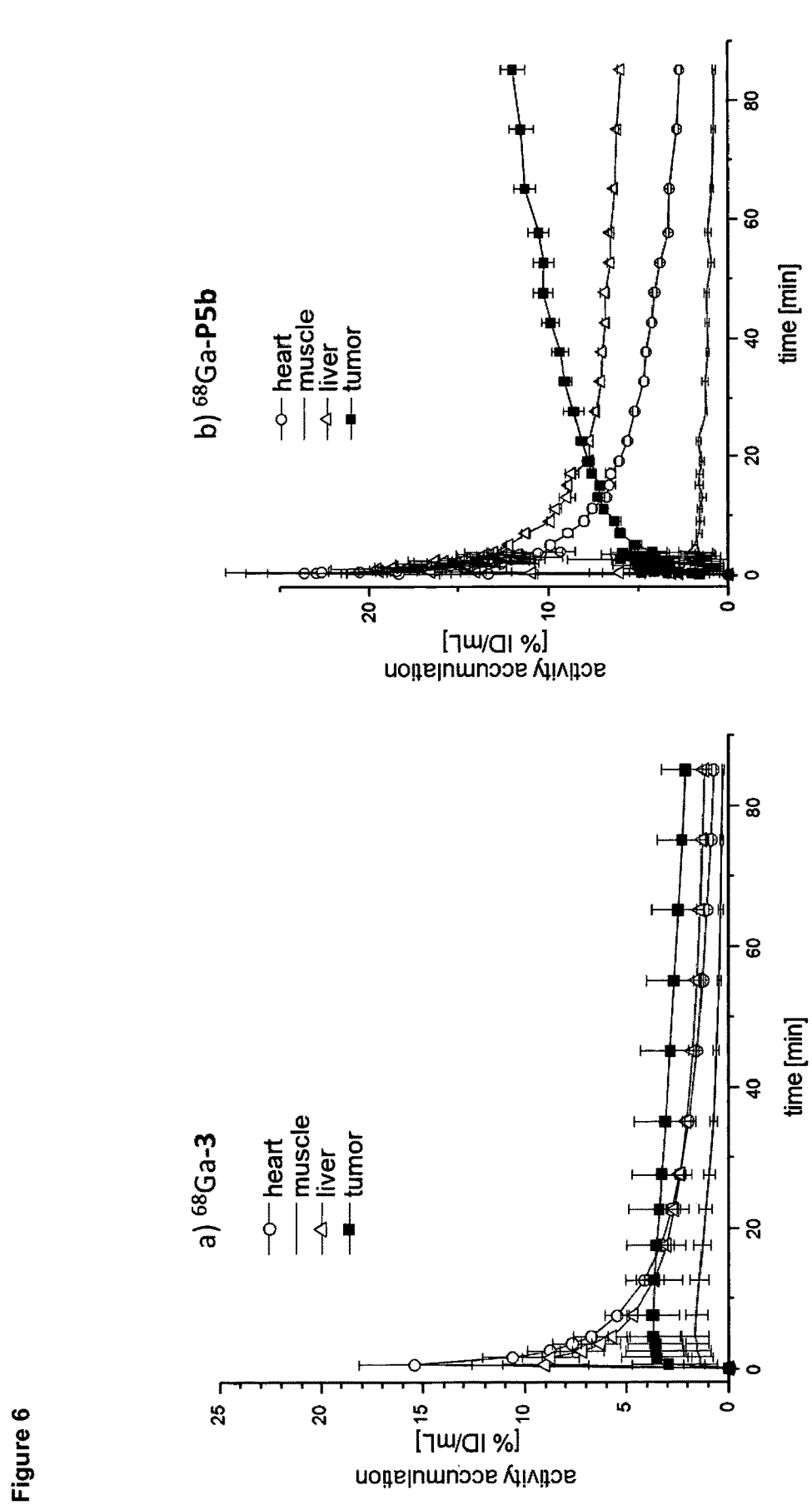
Figure 6:
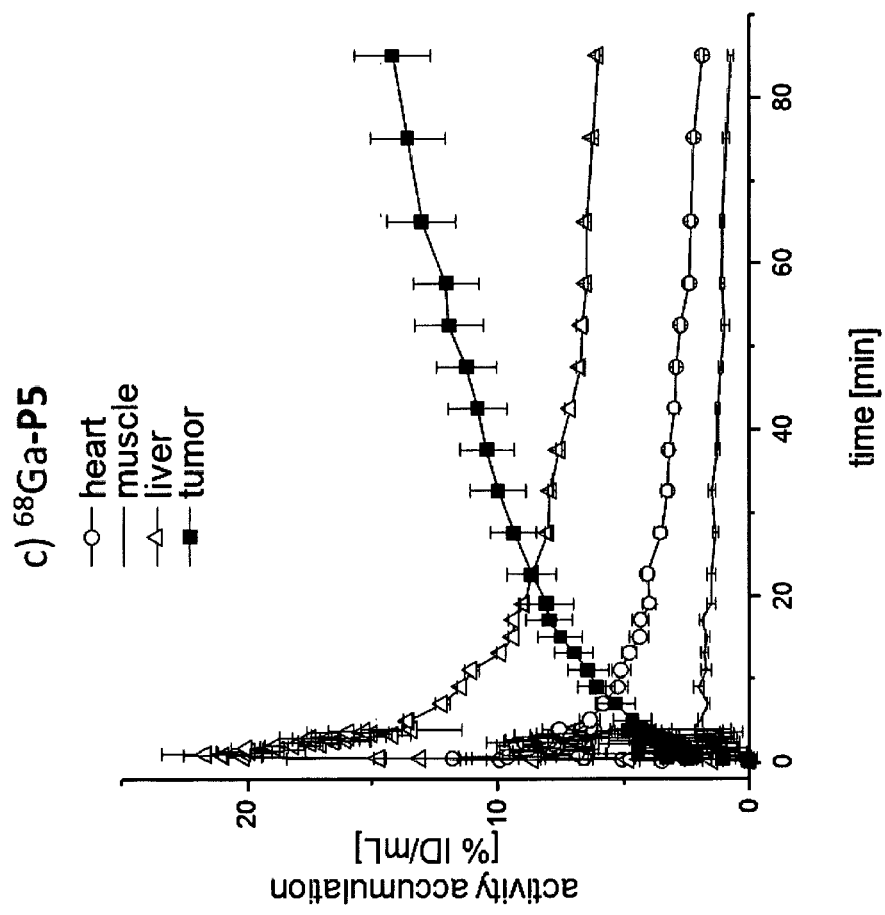

FIG. 6: Time-activity-curves (linear plot) in % ID/mL for blood pool (heart), muscle, liver and tumor. Graphs for (a)$^{68}$Ga-3, (b)$^{68}$Ga-15 and (c)$^{68}$Ga-16 are derived from dynamic small animal PET data.

The examples illustrate the invention.

EXAMPLE 1

Materials and Methods

1. Chemicals and Instrumentation

Solvents were purchased from Aldrich, Fluka, Merck and Prolabo, reagents from Aldrich, Fluka, Sigma, Merck, Acros and Lancaster in the quality "for synthesis", "per analysis" or "HPLC grade" and used without purification. Amino acids, derivatives for protecting groups as well as coupling reagents were purchased from Iris Biotech (Marktredwitz, Germany), Bachem (Bubendorf, Switzerland) or Carbolution (Saarbrücken, Germany). All reaction sensitive to oxygen or water were carried out in an argon atmosphere.

Solid phase peptide synthesis was carried out in plastic syringes (VWR) which were equipped with a filter. Reaction and wash solutions were sucked in the syringe, for mixing, the syringes were shaken manually or using an Intelli-Mixer syringe shaker (Neolab, Heidelberg, Germany). For loading of the first amino acid, the required equivalents (eq.) were calculated based on the theoretical loading capacity provided by the supplier.

Thin layer chromatography (TLC) for reaction control and the determination of $R_f$-values was done on aluminium foils coated with Silica 60, F254 (Merck). Peak detection was done under UV-light (254 nm) or after staining with Mostain-solution, respectively.

Preparative flash chromatogaphy was performed with 50- to 100-fold mass excess Silica 60 (particle size 0.040-0.063 mm, Merck) applying 1-1.5 bar overpressure.

Analytical and semipreparative reversed phase high performance liquid chromatography (HPLC) was performed using the following devices:

a) Sykam: gradient HPLC System (Sykam GmbH, Eresing, Germany), 206 PHD UV-Vis detector (Linear™ Instruments Corporation, Reno, USA), Winnie 32 software. Columns: a) Nucleosil 100 C18 (5 µm, 125×4.0 mm) (CS Chromatographie Services GmbH, Langerwehe, Germany), analytical, and b) Multospher 100 RP 18-5 (250×20 mm) (CS), semipreparative. For radioactivity detection, the outlet of the UV-photometer was connected to a NaI(TI) well-type scintillation counter from EG&G Ortec (MOnchen, Germany). b) Shimadzu: Prominence Gradient HPLC System (Shimadzu, Duisburg, Germany).

As eluents, mixtures of H$_2$O (solvent A) and acetonitrile (solvent B) containing 0.1 vol-% TFA were used. Different, linear gradient profiles in 15-30 min (analytical) and 15-30 min (semipreparative) were applied. Flow rates were 1 mL/min (analytical) and 8-9 mL/min (semipreparative), respectively. UV-detection was carried out at 220 and 254 nm.

Electrospray ionization mass spectrometry, ESI-MS was performed using a) a device from Finnigan (Typ LCQ in combination with the HPLC-system Hewlett Packard HP 1100). Columns: a) YMC Hydrosphere C18 (120 Å, 3 µm, 125 mm×2.1 mm), flow rate: 0.55 mL/min; b) YMC-UltraHT-Hydrosphere C18 (120 Å, 2 µm, 50 mm×2.0 mm), flow rate: 0.75 mL/min; c) YMC Octyl C8 (120 Å, 5 µm, 250 mm×2.1 mm), flow rate: 0.35 mL/min. As eluents, mixtures of H$_2$O and acetonitrile containing 0.1 vol-% formic acid were used for different linear gradients (7 min, 15 min, 40 min). or b) a Varian 500-MS IT mass spectrometer (Agilent Technologies, Santa Clara, USA).

Fluorescence Microscopy experiments were carried out using a BioRevo BZ9000 Fluorescence Microscope (Keyence, Osaka, Japan).

2. Synthesis 2.1. General Procedures

GP1. Loading of Tritylchloridpolystyrene (TCP) Resin

Peptide synthesis was carried out using TCP-resin (0.9 mmol/g) following standard Fmoc-strategy. Fmoc-Xaa-OH (1.2 eq.) were attached to the TCP resin with DIEA (2.5 eq.) in anhydrous DCM (0.8 mL/g resin) at room temperature for I h. The remaining trityl chloride groups were capped by addition of 1 mL/g(resin) of a solution of MeOH, DIEA (5:1; vzv) for 15 min. The resin was filtered and washed 5 times with DCM and 3 times with MeOH. The loading capacity was determined by weight after drying the resin under vacuum and ranged from 0.4-0.9 mmol/g.

GP2. Fmoc Deprotection

The resin-bound Fmoc peptide was treated with 20% piperidine in NMP (v/v) for 10 minutes and a second time for 5 minutes. The resin was washed 5 times with NMP.

GP3. N-Methylation Under Mitsunobu Conditions A solution of triphenylphosphine (5 eq.), DIAD (5 eq.) and MeOH (10 eq.) in dry THF (I mL/g resin) was added to the resin bound Ns protected peptides and shaken at room temperature for 10 minutes. The resin was filtered off, and washed 3 times with dry THF and 3 times with NMP.

GP4. HATU/HOAt Coupling

A solution of Fmoc-Xaa-OH, HATU (2 eq.), HOAt (2 eq.), DIPEA (4 eq.) in NMP (1 mL/g resin) was added to the resin bound peptides and shaken for 3 hours at room temperature and washed 5 times with NMP.

GP5. On-Resin Ns Deprotection

For Ns deprotection, the resin-bound Ns-peptides were stirred in a solution of inercaptoethanol (10 eq.) and DBU (5 eq.) in NMP (I mL/g resin) for 5 minutes. The deprotection procedure was repeated one more time and the resin was washed 5 times with NMP.

GP6. Peptide Cleavage from Resin

For complete cleavage from the resin the peptides were treated three times with a mixture of acetic acid/2,2,2-trifluoroethanol/DCM (3/1/6, v/v/v) at room temperature for half an hour and the solvents were evaporated under reduced pressure.

GP7. Peptide Backbone Cyclization

To a solution of peptide in DMF (I mM peptide concentration) and $NaHCO_3$ (5 eq.), DPPA (3 eq.) was added at RT and stirred over night or until no linear peptide could be observed by ESI-MS. The solvent was evaporated to a small volume under reduced pressure and the peptides precipitated in saturated NaCl solution and washed two times in HPLC grade water.

GP8. Removal of Dde Protecting Group

Dde-protection was carried out using 2% hydrazine in DMF at room temperature. After 30 min, deprotected peptides were precipitated using water (Pbf/tBu/Boc-protected peptides) or diethyl ether (deprotected peptides) and dried in a desiccator before further functionalization.

GP9. Removal of Acid Labile Side Chain Protectinq Groups

Cyclized peptides were stirred in a solution of TFA, water and TIPS (95:2.5:2.5; v:v:v) at room temperature for one hour or until no more protected peptide could be observed by ESI-MS and subsequently precipitated in diethyl ether, washed twice with diethyl ether and dried.

GP10. N-Methylation Under Mitsonobu Conditions

A solution of triphenylphosphine (5 eq.), DIAD (5 eq.) and MeOH (10 eq.) in dry THF (1 ml/g resin) was added to the resin-bound o-Ns protected peptides and shaken for 10 min at room temperature. The resin was filtered off, and washed 3 times with dry THE and 3 times with NMP.

GP11. Conjugation of Free Amino Function with Unprotected DOTA

DOTA (4 eq.), NHS (5 eq.) and EDCI (5 eq.) are dissolved in water, and DIPEA (8 eq.) are added. After 15 min, the respective peptide (1 eq.) is added in an equal volume of water. Progress of the coupling reaction is monitored using RP-HPLC. Upon completion of the reaction, the solvents are evaporated in vacuo. The residue is resuspended in methanol, the suspension is centrifuged, and the product dissolved in the methanolic supernatant is precipitated using diethyl ether, dried and purified using preparative RP-HPLC.

GP12. Preparation of $^{nat}$Ga-, $^{nat}$Lu-, $^{nat}$Bi- and $^{nat}$Y-DOTA Reference Compounds For the preparation of the $^{nat}$Ga- and $^{nat}$Bi-complexes, equal volumes of a 2 mM solution of $Ga(NO_3)_3$ or $Bi(OAc)_3$ in 1 M NaOAc buffer and a 2 mM aqueous solution of the respective peptide are mixed and heated to 95° C. for 30 min for $^{nat}$Ga- and 15 min RT for $^{nat}$Bi-complexation. The corresponding $^{nat}$Lu and $^{nat}$Y complexes are prepared by adding a 2.5-molar excess of the respective metal chloride dissolved in water to the peptide. Upon heating to 95° C. for 30 min, formation of the respective metal complexes is confirmed using RP-HPLC and ESI-MS.

GP13. Solution Phase Coniuaation of Peptide Linker and the Cyclicpentapeptide Scaffold A solution of Fmoc-Linker (1.5 eq.), TBTU (1.5 eq), HOBt (1.5 eq.) and DIPEA (3 eq.) in DMF was added to a solution of D-Orn-Dde-deprotected peptide in DMF (1 eq) and stirred for 90 min at RT. The product was then precipitated in saturated NaCl solution and washed two times in HPLC grade water.

GP14. Removal of Acid Labile Side Chain Protecting Groups

The side chain protected peptide was stirred in a solution of TFA, water and TIPS (95:2.5:2.5; v:v:v) at RT for one hour or until no more protected peptide could be observed by ESI-MS and precipitated in diethyl ether and washed two more times.

2.2. Synthesis of Cyclic Pentapeptide Analogs R and R1

CPCR4 (R)

CPCR4 (c[yorn'RNaIG] (R) was prepared as described previously[1]. Briefly, TCP-resin is loaded with Fmoc-Gly-OH according to GP1 and the linear peptide H-d-Orn-R (Pbf)-Nal-G is synthesized according to standard Fmoc-procedure (GP2 and GP4, respectively). The peptide is subsequently methylated according to GP10 and Fmoc-d-Tyr(OtBu)-OH (GP4) is coupled to the Ns-deprotected peptide. After deprotection (GP2), cleavage from the resin (GP6) and backbone cyclization (GP7) are carried out. Removal of the Dde-protecting group (GP8) is followed by precipitation of the crude peptide in sat. aq. NaCl-solution and lyophilization from a $^tBuOH/H_2O$-solution. R (450 mg, 0.64 mmol, 64%) is obtained as yellowish powder (purity>90%).

c[yorn'RNaIG) (R)

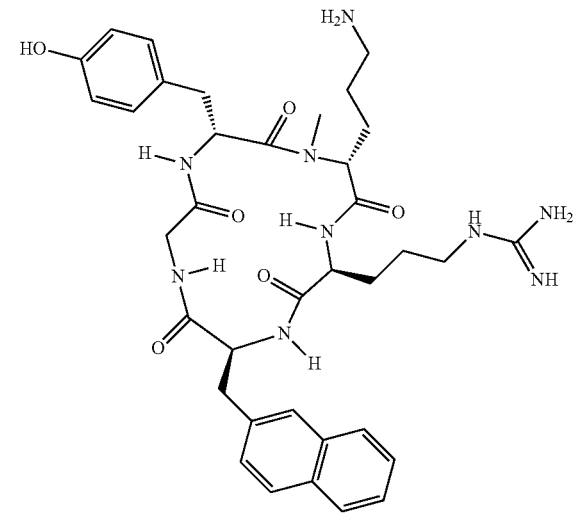

Chemical Formula: $C_{36}H_{47}N_9O_6$
Exact Mass: 701.36

HPLC (10-50% 15 min): $t_R$=9.7 min. MS (ESI): m/z=702.4 $[M+H]^+$.

Iodo-CPCR4 (R1)

Synthesis of the unlabeled reference compound iodo-CPCR4.3 was carried out using N-iodosuccinimide (NIS) in acetonitrile/water[2] Briefly, CPCR4 was dissolved in a 1:1 (v/v) mixture of acetonitrile and water to yield a 9 mM solution, and 0.45 eq NIS were added. Upon completion of the reaction (5-10 min at RT), iodo-CPCR4 (R1) was isolated using semipreparative RP-HPLC.

c[iyorn'RNaIG) (R1)

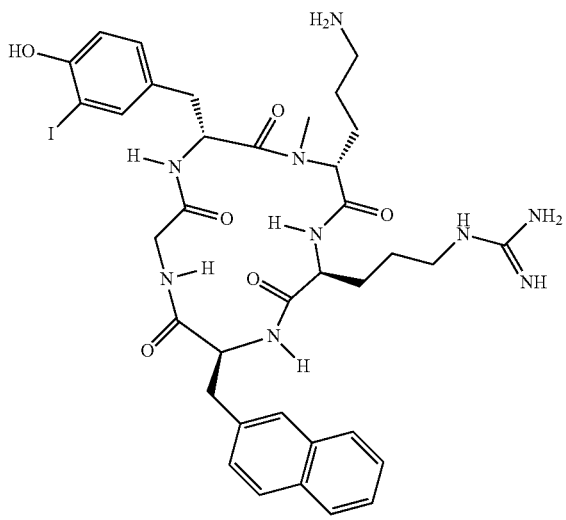

Chemical Formula: $C_{36}H_{46}IN_9O_6$
Exact Mass: 827.26

HPLC (15-55% B in 15 min): $t_R$=8 min; MS (ESI): m/z=829.4 $[M+H]^+$.

FC131 (R2)

The synthesis of FC131 (R2) was performed according to the protocol described for peptide R.

c[yRRNaIG] (R2)

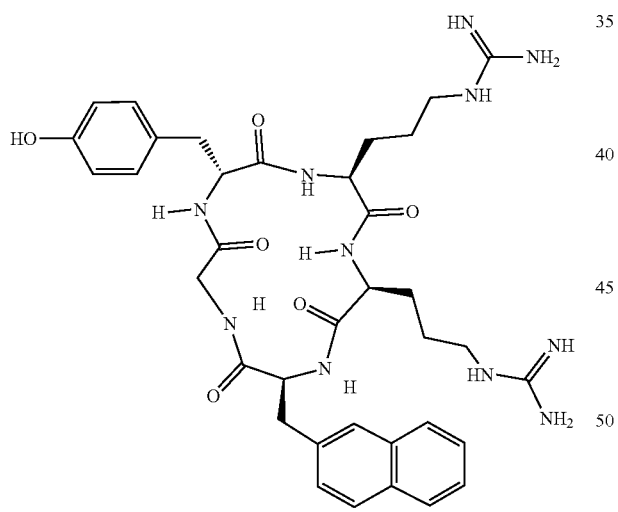

Chemical Formula: $C_{36}H_{47}N_{11}O_6$
Exact Mass: 729.37

HPLC (15-55% B in 15 min): $t_R$=8 min; MS (ESI): m/z=829.4 $[M+H]^+$.

2.3. Synthesis of linking units (L1-L5) for conjugation with the D-Orn-side chain of R or R1 TCP-resin is loaded with Fmoc-ABS-OH or (Fmoc-AMBS-OH) according to GP1 and the linear peptide chains are constructed according to standard Fmoc-procedure (GP2 and GP4, respectively). After cleavage from the resin (GP6) as the Fmoc-protected derivative, the peptide linking units are used without further purification.

Fmoc-dDap(Boc)-Gly-ABS (L1)

Resin bound 4-(Fmoc-amino)benzoic acid (0.224 mmol, 1.0 eq.) were allowed to pre swell for 30 min in DMF. 3.0 eq. Fmoc-Gly-OH and 1.5 eq. of Fmoc-D-Dap(Boc)-OH were coupled according to GP2 and GP4, respectively). The linear peptide was cleaved from the resin (GP6), precipitated in diethyl ether and freeze-dried overnight to give the linking unit L1.

Fmoc-dDap(Boc)-Gly-ABS (R)-4-(2-(2,3-diaminopropanamido)acetamido)benzoic acid (L1)

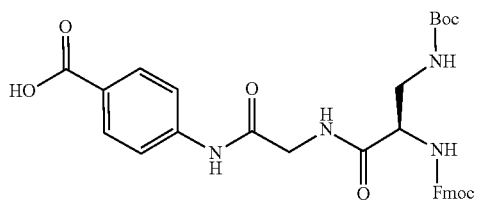

Chemical Formula: $C_{32}H_{34}N_4O_8$
Exact Mass: 602.24

HPLC (10-90% B in 15 min): $t_R$=12.0 min; MS (ESI): m/z=502.5 $[M+H-(Boc)]^+$.

Fmoc-dLys(Boc)-Gly-ABS (L2)

Resin bound 4-(Fmoc-amino)benzoic acid (0.224 mmol, 1.0 eq.) were allowed to pre swell for 30 min in DMF. 3.0 eq. Fmoc-Gly-OH and 1.5 eq. of Fmoc-D-Lys(Boc)-OH were coupled according to GP2 and GP4, respectively). The linear peptide was cleaved from the resin (GP6), precipitated in diethyl ether and freeze-dried overnight to give the linking unit L2.

Fmoc-dLys(Boc)-Gly-ABS (L2)

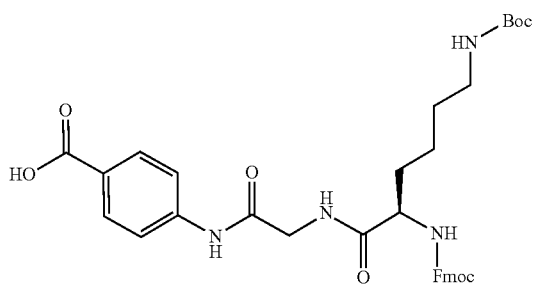

Chemical Formula: $C_{35}H_{40}N_4O_8$
Exact Mass: 644.28

HPLC (10-90% B in 15 min): $t_R$=13.0 min; MS (ESI): m/z=545.4 $[M+H-(Boc)]^+$.

Fmoc-dArq(Pbf)-Gly-ABS (L3)

Resin bound 4-(Fmoc-amino)benzoic acid (0.224 mmol, 1.0 eq.) were allowed to pre swell for 30 min in DMF. 3.0 eq. Fmoc-Gly-OH and 1.5 eq. of Fmoc-D-Arg(Pbf)-OH were coupled according to GP2 and GP4, respectively). The linear peptide was cleaved from the resin (GP6), precipitated in diethyl ether and freeze-dried overnight to give the linking unit.

Fmoc-dArg(Pbf)-Gly-ABS (L3)

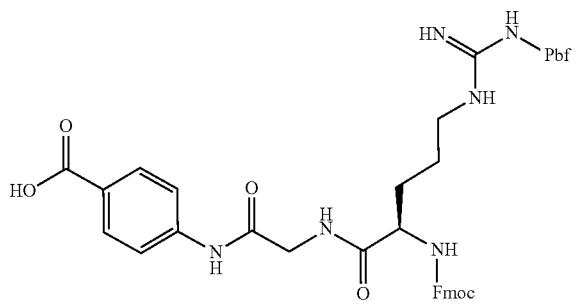

Chemical Formula: C₄₃H₄₈N₆O₉S
Exact Mass: 824.32

HPLC (10-90% B in 15 min): $t_R$=12.6 min; MS (ESI): m/z=573.5 [M+H-(Pbf)]⁺.

Fmoc-dArg(Pbf)-dAla-ABS (L4)

Resin bound 4-(Fmoc-amino)benzoic acid (0.224 mmol, 1.0 eq.) were allowed to pre swell for 30 min in DMF. 3.0 eq. Fmoc-D-Ala-OH and 1.5 eq. of Fmoc-D-Arg(Pbf)-OH were coupled according to GP2 and GP4, respectively). The linear peptide was cleaved from the resin (GP6), precipitated in diethyl ether and freeze-dried overnight to give the linking unit.

Fmoc-dArg(Pbf)-dAla-ABS (L4)

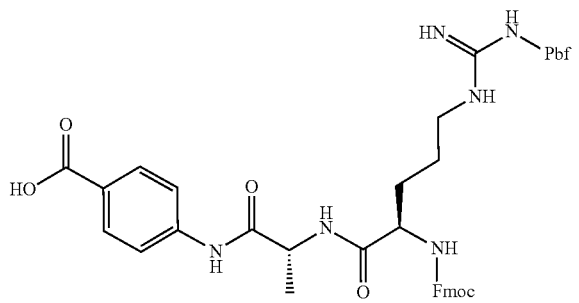

Chemical Formula: C₄₄H₅₀N₆O₉S
Exact Mass: 838.34

HPLC (10-90% B in 15 min): $t_R$=11.6 min; MS (ESI): m/z=587.5 [M+H-(Pbf)]⁺.

Fmoc-dArq(Pbf)-dAla-AMBS (L5)

Resin bound 4-(Fmoc-amino)methylbenzoic acid (0.224 mmol, 1.0 eq.) were allowed to pre swell for 30 min in DMF. 3.0 eq. Fmoc-D-Ala-OH and 1.5 eq. of Fmoc-D-Arg(Pbf)-OH were coupled according to GP2 and GP4, respectively). The linear peptide was cleaved from the resin (GP6), precipitated in diethyl ether and freeze-dried overnight to give the linking unit.

Fmoc-dArg(Pbf)-dAla-AMBS (L5)

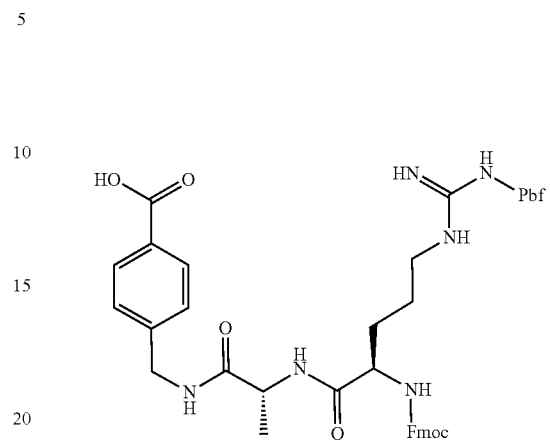

Chemical Formula: C₄₅H₅₂N₆O₉S
Exact Mass: 852.35

HPLC (10-90% B in 15 min): $t_R$=11.6 min; MS (ESI): m/z=587.5 [M+H-(Pbf)]⁺.

2.4. Synthetic Description of the Individual Compounds (P1-P6)

TCP-resin is loaded with Fmoc-Gly-OH according to GP1 and the linear peptide H-d-Ala-R(Pbf)-Nal-G is synthesized according to standard Fmoc-procedure (GP2 and GP4, respectively). The peptide is subsequently alkylated with Dde-aminohexanol according to GP10 and Fmoc-d-Tyr (OtBu)-OH (GP4) is coupled to the Ns-deprotected peptide. After deprotection (GP2), cleavage from the resin (GP6) and backbone cyclization (GP7) are carried out. Removal of the Dde-protecting group (GP8) is followed by precipitation of the crude peptide in sat. aq. NaCk-solution and lyophilization from a ACN/H₂O-solution. PO (132 mg, 126 µM, 31%) is obtained as yellowish powder (purity>90%). The respective scaffold R or R1 was conjugated with linking units (L1-L5) according to GP13. Subsequent condensation of the chelator is performed according to GP11.

cyclo[i-yorn'(DOTA-d-(4-amino)benzoyl-)RNaIG (P1)

Synthesis of the respective Dde-deprotected, cyclic peptide R1 was carried out according to the general procedures outlined above. Fmoc-ABS and Fmoc-DAsp(tBu) was coupled according to GP4 and GP2. Upon Fmoc-deprotection using 20% piperidine in DMF (GP2), the peptide was purified using preparative RP-HPLC and DOTA was conjugated according to GP11. Again, the peptide was purified using preparative RP-HPLC.

33 cyclo[i-yorn'(DOTA-d-(4-amino)benzoyl-)RNaIG (P1)

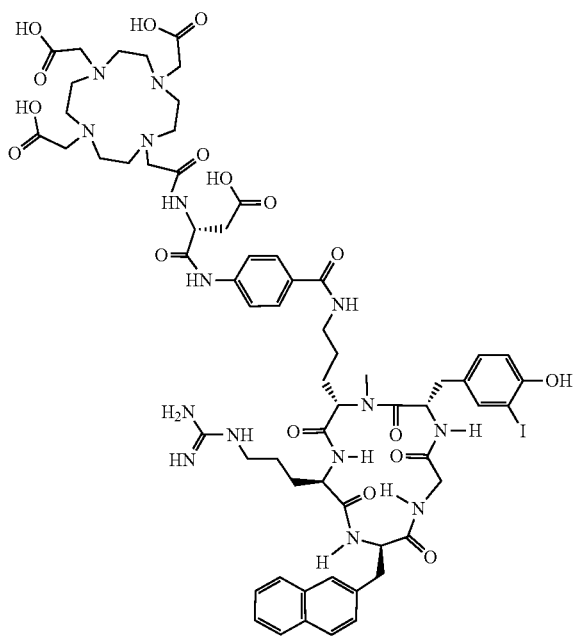

Chemical Formula: $C_{63}H_{82}IN_{15}O_{17}$
Exact Mass: 1447.51

HPLC (25-55% B in 15 min): $t_R$=10.1 min; MS (ESI): m/z=1448.8 $[M+H]^+$, 725.3 $[M+H+H]^{2+}$.

cyclo[i-yorn'(DOTA-dapG-(4-amino)benzoyl-)RNaIG (P2):

R1 was coupled to L1 according to the general procedures GP13. Upon Fmoc-deprotection using 20% piperidine in DMF (GP2), the peptide was purified using preparative RP-HPLC and DOTA was conjugated according to GP11. Again, the peptide was purified using preparative RP-HPLC.

cyclo[i-yorn'(DOTA-dapG-(4-amino)benzoyl-)RNaIG (P2):

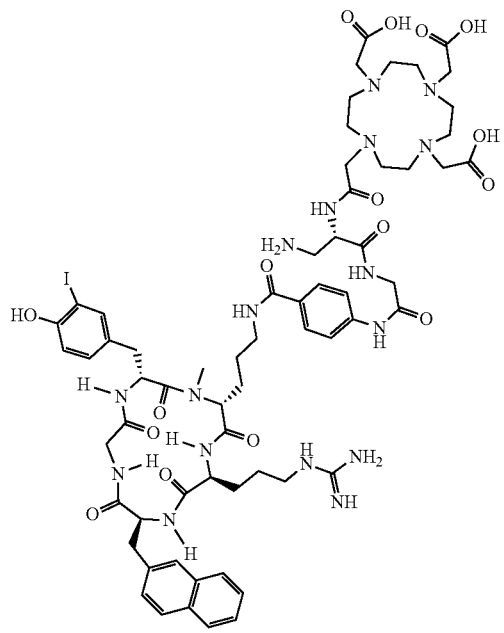

Chemical Formula: $C_{64}H_{86}IN_{17}O_{16}$
Exact Mass: 1475.55

34

HPLC (25-65% B in 15 min): $t_R$=11.9 min; MS (ESI):m/z=1476.8 $[M+H]^+$, 739.3 $[M+H+H]^{2+}$.

cyclo[i-yorn'(DOTA-kG-(4-amino)benzoyl-)RNaIG (P3):

R1 or R was coupled to L2 according to the general procedures GP13. Upon Fmoc-deprotection using 20% piperidine in DMF (GP2), the peptide was purified using preparative RP-HPLC and DOTA was conjugated according to GP11. Again, the peptide was purified using preparative RP-HPLC.

cyclo[i-yorn'(DOTA-kG-(4-amino)benzoyl-)RNaIG (P3):

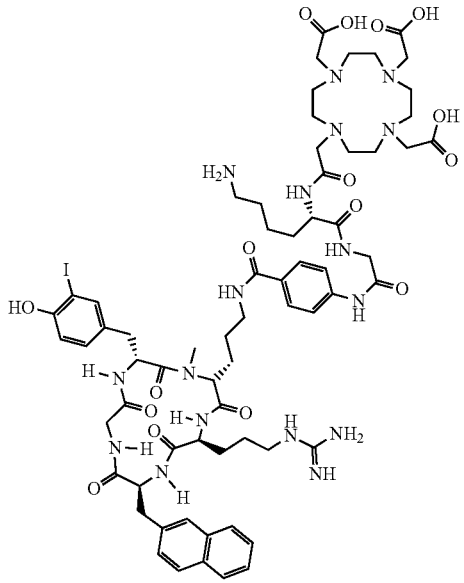

Chemical Formula: $C_{67}H_{92}IN_{17}O_{16}$
Exact Mass: 1517.60 cyclo[i-yorn'(DOTA-kG-(4-amino)benzoyl-)RNaIG (P3b):

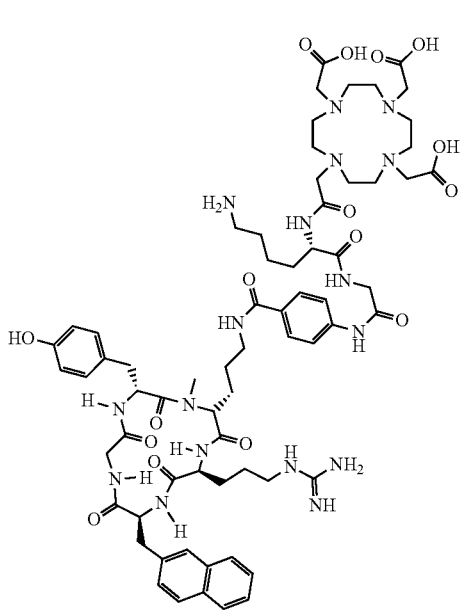

Chemical Formula: $C_{67}H_{93}N_{17}O_{16}$
Exact Mass: 1391.70

HPLC (25-55% R in 15 min): $t_R$=12.8 min: HPLC (15-55% B in 15 min): $t_R$=7.9 min: MS MS (ESI): m/z=1519.1 [M+H]$^+$, 760.4 (ESI): m/z=1393.2 [M+H]$^+$. [M+H+H]$^{2+}$.

cyclo[i-yorn'(DOTA-rG-(4-amino)benzoyl-)RNaIG (P4):

R1/R was coupled to L3 according to the general procedures GP13. Upon Fmoc-deprotection using 20% piperidine in DMF (GP2), the peptide was purified using preparative RP-HPLC and DOTA was conjugated according to GP11. Again, the peptide was purified using preparative RP-HPLC.

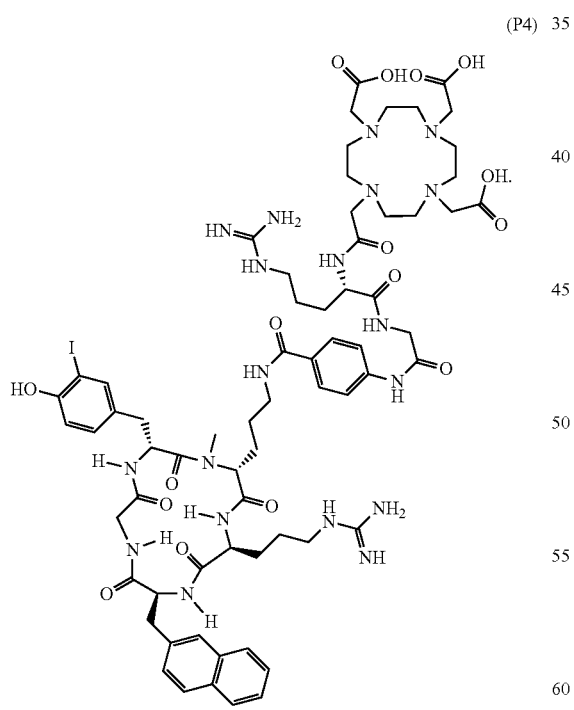

(P4)

cyclo[i-yorn'(DOTA-rG-(4-amino)benzoyl-)RNaIG
Chemical Formula: C$_{67}$H$_{92}$IN$_{19}$O$_{16}$
Exact Mass: 1545.60
HPLC (22-55% B in 15 min): $t_R$ = 13.3 min;
MS (ESI): m/z = 1547.2 [M + H]$^+$, 774.5 [M + H + H]$^{2+}$

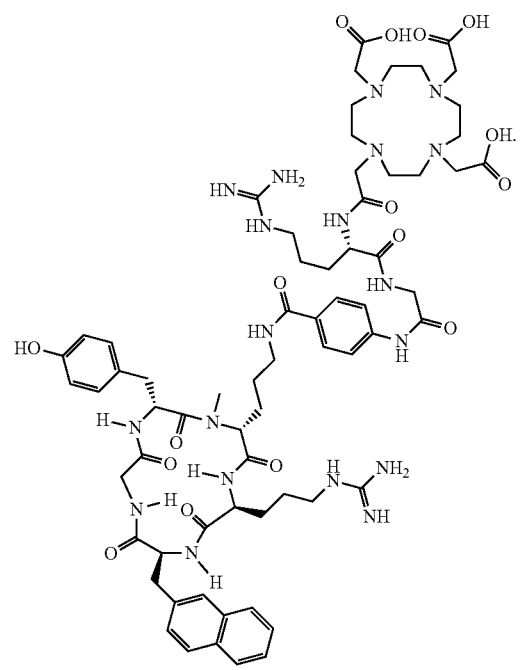

(P4b)

cyclo[-yorn'(DOTA-rG-(4-amino)benzoyl-)RNaIG
Chemical Formula: C$_{67}$H$_{93}$N$_{19}$O$_{16}$
Exact Mass: 1419.70
HPLC (15-55% B in 15 min): $t_R$ = 8.2 min;
MS (ESI): m/z = 1421.5 [M + H]$^+$ cyclo[i-yorn'(DOTA-ra-(4-amino)benzoyl-)RNaIG (P5):

R1/R was coupled to L4 according to the general procedures GP13. Upon Fmoc-deprotection using 20% piperidine in DMF (GP2), the peptide was purified using preparative RP-HPLC and DOTA was conjugated according to GP11. Again, the peptide was purified using preparative RP-HPLC.

(P5)

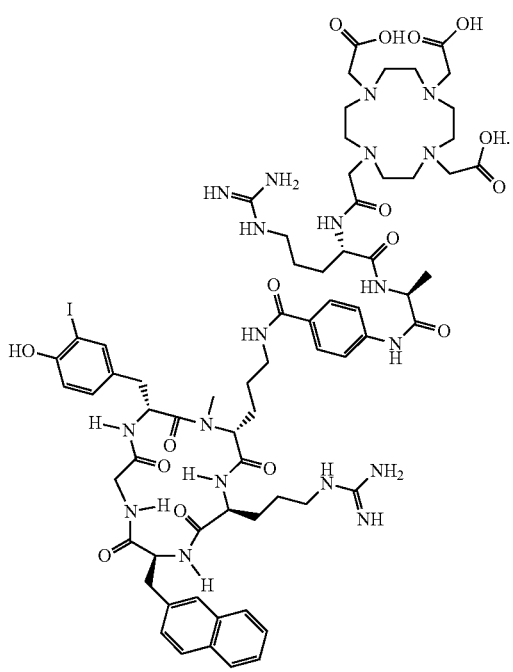

cyclo[i-yorn'(DOTA-ra-(4-amino)benzoyl-)RNaIG
Chemical Formula: $C_{68}H_{94}IN_{19}O_{16}$
Exact Mass: 1559.62
HPLC (22-55% B in 15 min): $t_R$ = 12.1 min;
MS (ESI): m/z = 1560.2 [M + H]$^+$, 781.5 [M + H + H]$^{2+}$ (P5b)

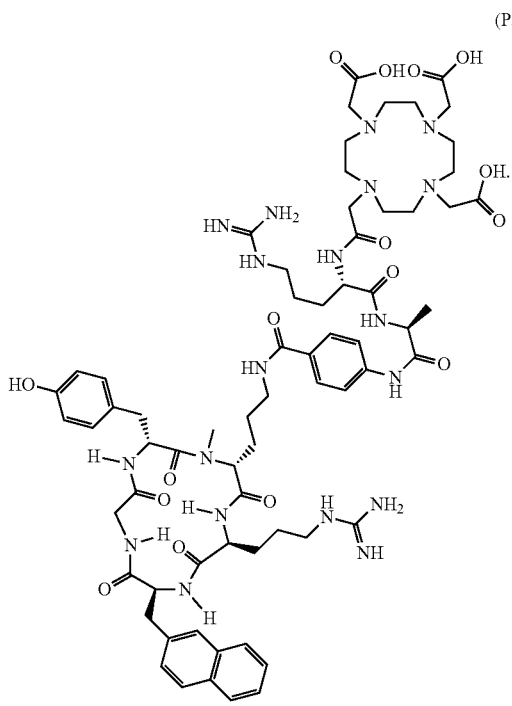

cyclo[-yorn'(DOTA-ra-(4-amino)benzoyl-)RNaIG
Chemical Formula: $C_{68}H_{95}N_{19}O_{16}$
Exact Mass: 1433.72
HPLC (15-55% B in 15 min): $t_R$ = 8.0 min;
MS (ESI): m/z = 1435.1 [M + H]$^+$, 717.3 [M + H + H]$^{2+}$ cyclo[i-yorn'(DOTA-ra-(4-amino)methylbenzoyl-)RNaIG (P6):

R1/R was coupled to L5 according to the general procedures GP13. Upon Fmoc-deprotection using 20% piperidine in DMF (GP2), the peptide was purified using preparative RP-HPLC and DOTA was conjugated according to GP11. Again, the peptide was purified using preparative RP-HPLC.

cyclo[-yorn'(DOTA-ra-(4-amino)methylbenzoyl-)RNaIG (P6b):

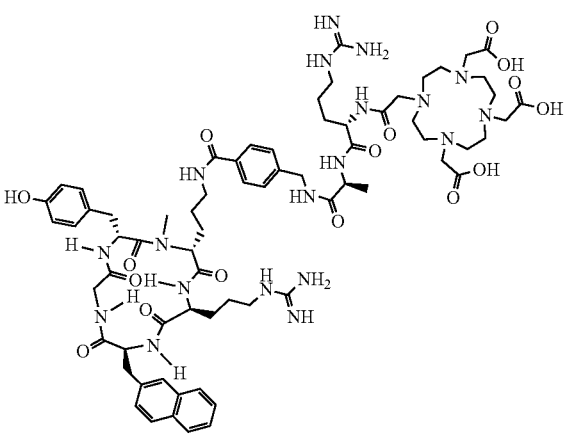

Chemical Formula: $C_{69}H_{97}N_{19}O_{16}$
Exact Mass: 1447.14

HPLC (15-55% B in 15 min): $t_R$=8.0 min; MS (ESI): m/z=1435.1 [M+H]$^+$, 717.3 [M+H+H]$^{2+}$.

$^{nat}$Ga-compounds: $^{nat}$Ga$^{III}$-chelate formation was achieved using the protocol GP12. The resulting 1 mM aqueous solutions of the respective $^{nat}$Ga-complexes were diluted (serial dilution 10$^{-4}$ to 10$^{-11}$ M in Hanks salt solution (HBSS) with 1% BSA) and used in the in vitro IC$_{50}$ studies without further processing.

cyclo[i-yorn'([$^{nat}$Ga]DOTA-dapG-(4-amino)benzoyl-)RNaIG ([$^{nat}$Ga]P2): HPLC (25% to 65% B in 15 min): $t_R$=11.4 min; K'=5.3; Calculated monoisotopic mass ($C_{64}H_{84}GaN_{17}O_{16}$): 1542.46, found by ESI-MS: m/z=1544.8 [M+H]$^+$, 772.4 [M+2H]$^{2+}$.

cyclo[yorn'([$^{nat}$Ga]DOTA-kG-(4-amino)benzoyl-)RNaIG ([$^{nat}$Ga]P3b): HPLC (15% to 55% B in 15 min): $t_R$=7.6 min; K'=3.0; Calculated monoisotopic mass ($C_{67}H_{91}GaN_{17}O_{16}$): 1458.61, found by ESI-MS: m/z=1459.8 [M+H]$^+$, 730.2 [M+2H]$^{2+}$.

cyclo[i-yorn'([$^{nat}$Ga]DOTA-kG-(4-amino)benzoyl-)RNaIG ([$^{nat}$Ga]P3): HPLC (25% to 55% B in 15 min): $t_R$=12.9 min; K'=6.1; Calculated monoisotopic mass ($C_{67}H_{90}GaIN_{17}O_{16}$): 1584.51, found by ESI-MS: m/z=1585.0 [M+H]$^+$, 1608.9 [M+Na]$^+$, 793.7 [M+2H]$^{2+}$.

cyclo[yorn'([$^{nat}$Ga]DOTA-rG-(4-amino)benzoyl-)RNaIG ([$^{nat}$Ga]P4b): HPLC (15% to 55% B in 15 min): $t_R$=7.7 min; K'=3.2; Calculated monoisotopic mass ($C_{67}H_{91}GaN_{19}O_{16}$): 1468.61, found by ESI-MS: m/z=745.3 [M+2H]$^{2+}$.

cyclo[i-yorn'([$^{nat}$Ga]DOTA-rG-(4-amino)benzoyl-)RNaIG ([$^{nat}$Ga]P4): HPLC (25% to 55% B in 15 min): $t_R$=12.6 min; K'=6.8; Calculated monoisotopic mass ($C_{67}H_{90}GaIN_{19}O_{16}$): 1612.51, found by ESI-MS: m/z=1614.9 [M+H]$^+$, 808.0 [M+2H]$^{2+}$.

cyclo[yorn'([$^{nat}$Ga]DOTA-ra-(4-amino)benzoyl-)RNaIG ([$^{nat}$Ga]P5b): HPLC (15% to 55% B in 15 min): $t_R$=6.8 min; K'=3.5; Calculated monoisotopic mass ($C_{68}H_{93}GaN_{19}O_{16}$): 1500.63, found by ESI-MS: m/z=751.5 [M+2H]$^{2+}$, 787.2 [M+2K]$^{2+}$.

cyclo[i-yorn'([$^{nat}$Ga]DOTA-ra-(4-amino)benzoyl-)RNaIG ([$^{nat}$Ga]P5): HPLC (25% to 55% B in 15 min): $t_R$=7.9 min; K'=3.9; Calculated monoisotopic mass ($C_{68}H_{92}GaN_{19}O_{16}$): 1626.53, found by ESI-MS: m/z=1626.8 [M+H]$^+$, 815.0 [M+2H]$^{2+}$.

cyclo[i-yorn'([$^{nat}$Ga]DOTA-ra-(4-amino)methylbenzoyl-)RNaIG ([$^{nat}$Ga]P6b): HPLC (25% to 55% B in 15 min): $t_R$=7.9 min; K'=3.9; Calculated monoisotopic mass ($C_{68}H_{92}GaN_{19}O_{16}$): 1626.53, found by ESI-MS: m/z=1626.8 [M+H]$^+$, 815.0 [M+2H]$^{2+}$.

$^{nat}$Lu-compounds: $^{nat}$Lu$^{III}$-chelate formation was achieved using the protocol GP12. The resulting 1 mM aqueous solutions of the respective $^{nat}$Lu-complexes were diluted (serial dilution 10$^{-4}$ to 10$^{11}$ M in HBSS with 1% BSA) and used in the in vitro IC$_{50}$ studies without further processing.

cyclo[i-yorn'([$^{nat}$Lu]DOTA-d-(4-amino)benzoyl-)RNaIG ([$^{nat}$Lu]P1): HPLC (35% to 65% B in 15 min): $t_R$=8.0 min; K'=3.4; Calculated monoisotopic mass ($C_{63}H_{79}ILuN_{15}O_{17}$): 1619.42, found by ESI-MS: m/z=1620.9 [M+H]$^+$, 1,642.8 [M+Na]$^+$, 811.2 [M+2H]$^{2+}$, 822.0 [M+H+Na]$^{2+}$.

cyclo[i-yorn'([$^{nat}$Lu]DOTA-dapG-(4-amino)benzoyl-)RNaIG ([$^{nat}$Lu]P2): HPLC (25% to 65% B in 15 min): $t_R$=10.8 min; K'=9.8; Calculated monoisotopic mass ($C_{64}H_{83}ILuN_{17}O_{16}$): 1647.47, found by ESI-MS: m/z=1648.9 [M+H]$^+$, 825.2 [M+2H]$^{2+}$, 860.5 [M+2K]$^{2+}$.

cyclo[yorn'([$^{nat}$Lu]DOTA-kG-(4-amino)benzoyl-)RNaIG ([$^{nat}$Lu]P3b): HPLC (15% to 55% B in 15 min): $t_R$=7.5 min; K'=4.0; Calculated monoisotopic mass ($C_{67}H_{90}LuN_{17}O_{16}$): 1563.62, found by ESI-MS: m/z=1565.4 [M+H]$^+$.

cyclo[i-yorn'([$^{nat}$Lu]DOTA-kG-(4-amino)benzoyl-)RNaIG ([$^{nat}$Lu]P3): HPLC (25% to 55% B in 15 min): $t_R$=13.1 min; K'=7.7; Calculated monoisotopic mass ($C_{67}H_{89}ILuN_{17}O_{16}$): 1689.51, found by ESI-MS: m/z=1691.8 [M+H]$^+$, 1712.7 [M+Na]$^+$, 846.4 [M+2H]$^{2+}$, 857.1 [M+H+Na]$^{2+}$.

cyclo[yorn'([$^{nat}$Lu]DOTA-rG-(4-amino)benzoyl-)RNaIG ([$^{nat}$Lu]P4b): HPLC (15% to 55% B in 15 min): $t_R$=7.2 min; K'=4.1; Calculated monoisotopic mass ($C_{67}H_{90}LuN_{19}O_{16}$): 1591.62, found by ESI-MS: m/z=1592.5 [M+H]$^+$, 1631.0 [M+K]$^+$.

cyclo[i-yorn'([$^{nat}$Lu]DOTA-rG-(4-amino)benzoyl-)RNaIG ([$^{nat}$Lu]P4): HPLC (25% to 55% B in 15 min): $t_R$=13.4 min; K'=7.9; Calculated monoisotopic mass ($C_{67}H_{89}IN_{19}O_{16}$): 1717.52, found by ESI-MS: m/z=1719.9 [M+H]$^+$, 860.5 [M+2H]$^{2+}$, 871.1 [M+H+Na]$^+$, 895.7 [M+2K]$^{2+}$.

cyclo[yorn'([$^{nat}$Lu]DOTA-ra-(4-amino)benzoyl-)RNaIG ([$^{nat}$Lu]P5b): HPLC (15% to 55% B in 15 min): $t_R$=7.5 min; K'=4.0; Calculated monoisotopic mass ($C_{68}H_{92}LuN_{19}O_{16}$): 1605.64, found by ESI-MS: m/z=1732.8 [M+H]$^+$, 867.3 [M+2H]$^{2+}$, 902.6 [M+2K]$^{2+}$.

cyclo[i-yorn'([$^{nat}$Lu]DOTA-ra-(4-amino)benzoyl-)RNaIG ([$^{nat}$Lu]P5): HPLC (25% to 55% B in 15 min): $t_R$=6.5 min; K'=2.3; Calculated monoisotopic mass ($C_{68}H_{91}LuN_{19}O_{16}$): 1731.53, found by ESI-MS: m/z=1732.8 [M+H]+, 867.3 [M+2H]$^{2+}$, 902.6 [M+2K]$^{2+}$.

The $^{nat}$Y-complexes were prepared as described in GP12. After cooling, the $^{nat}$Y$^{III}$-chelate formation was confirmed using HPLC and MS. The resulting 1 mM aqueous solutions of the respective $^{nat}$Y-complexes were diluted (serial dilution 10$^{-4}$ to 10$^{11}$ M in HBSS with 1% BSA) and used in the in vitro IC$_{50}$ studies without further processing.

cyclo[i-yorn'([$^{nat}$Y]DOTA-dapG-(4-amino)benzoyl-)RNaIG ([$^{nat}$Y]P2): HPLC (25% to 65% B in 15 min): $t_R$=11.5 min; K'=6.1; Calculated monoisotopic mass ($C_{64}H_{83}IN_{17}O_{16}Y$): 1561.43, found by ESI-MS: m/z=1562.7 [M+H]$^+$, 782.3 [M+2H]$^{2+}$, 793.0 [M+H+Na]$^{2+}$ cyclo[yorn'([$^{nat}$Y]DOTA-kG-(4-amino)benzoyl-)RNaIG ([$^{nat}$Y]P3b): HPLC (15% to 55% B in 15 min): $t_R$=7.8 min; K'=2.7; Calculated monoisotopic mass ($C_{67}H_{90}N_{17}O_{16}Y$): 1477.58, found by ESI-MS: m/z=1478.9 [M+H]$^+$, 740.4 [M+2H]$^{2+}$.

cyclo[i-yorn'([$^{nat}$Y]DOTA-kG-(4-amino)benzoyl-)RNaIG ([$^{nat}$Y]P3): HPLC (25% to 55% B in 15 min): $t_R$=12.9 min; K'=7.6; Calculated monoisotopic mass ($C_{67}H_{89}IN_{17}O_{16}Y$): 1603.48, found by ESI-MS: m/z=1605.7 [M+H]$^+$, 1626.6 [M+Na]$^+$, 803.4 [M+2H]$^{2+}$, 814.1 [M+H+Na]$^{2+}$.

cyclo[yorn'([$^{nat}$Y]DOTA-rG-(4-amino)benzoyl-)RNaIG ([$^{nat}$Y]P4b): HPLC (15% to 55% B in 15 min): $t_R$=8.0 min; K'=2.8; Calculated monoisotopic mass ($C_{67}$IHON$_{19}O_{16}Y$): 1505.59, found by ESI-MS: m/z=1506.2 [M+H]$^+$, 754.3 [M+2H]$^{2+}$.

cyclo[i-yorn'([$^{nat}$Y]DOTA-rG-(4-amino)benzoyl-)RNaIG ([$^{nat}$Y]P4): HPLC (25% to 55% B in 15 min): $t_R$=13.3 min; K'=7.9; Calculated monoisotopic mass ($C_{67}H_{89}IN_{19}O_{16}Y$): 1631.48, found by ESI-MS: m/z=1632.9 [M+H]$^+$, 817.4 [M+2H]$^{2+}$, 828.1 [M+H+Na]$^{2+}$, 852.7 [M+2K]$^{2+}$.

cyclo[yorn'([$^{nat}$Y]DOTA-ra-(4-amino)benzoyl-)RNaIG ([$^{nat}$Y]P5b): HPLC (15% to 55% B in 15 min): $t_R$=7.0 min; K'=3.6; Calculated monoisotopic mass ($C_{68}H_{92}N_{19}O_{16}Y$): 1519.60, found by ESI-MS: m/z=761.0 [M+2H]$^{2+}$.

cyclo[i-yorn'([$^{nat}$Y]DOTA-ra-(4-amino)benzoyl-)RNaIG ([$^{nat}$Y]P5): HPLC (25% to 55% B in 15 min): $t_R$=9.6 min; K'=2.8; Calculated monoisotopic mass ($C_{68}H_{91}IN_{19}O_{16}Y$): 1645.50, found by ESI-MS: m/z=1646.9 [M+H]$^+$, 824.1 [M+2H]$^{2+}$, 859.5 [M+2K]$^{2+}$.

Bismuth complexation was performed using the protocol described in GP12. Formation of the $^{nat}$Bi$^{III}$-chelate was confirmed using HPLC and ESI-MS. The resulting 1 mM aqueous solutions of the respective $^{nat}$Bi-complexes were diluted (serial dilution 10$^{-4}$ to 10$^{-10}$ M in HBSS with 1% BSA) and used in the in vitro IC$_{50}$ studies without further processing.

cyclo[i-yorn'([$^{nat}$Bi]DOTA-dapG-(4-amino)benzoyl-)RNaIG ([$^{nat}$Bi]P2): HPLC (15% to 55% B in 15 min): $t_R$=8.9 min; K'=3.9; Calculated monoisotopic mass ($C_{64}H_{83}BiIN_{17}O_{16}$): 1681.51, found by ESI-MS: m/z=1682.2 [M+H]$^+$, 839.8 [M+2H]$^{2+}$.

cyclo[i-yorn'([$^{nat}$Bi]DOTA-kG-(4-amino)benzoyl-)RNaIG ([$^{nat}$Bi]P3): HPLC (15% to 55% B in 15 min): $t_R$=8.9 min; K'=3.3; Calculated monoisotopic mass ($C_{67}H_{89}BiN_{17}O_{16}$): 1724.56, found by ESI-MS: m/z=1726.2 [M+H]$^+$, 863.2 [M+2H]$^{2+}$.

cyclo[i-yorn'([$^{nat}$Bi]DOTA-rG-(4-amino)benzoyl-)RNaIG ([$^{nat}$Bi]P4): HPLC (15% to 55% B in 15 min): $t_R$=9.0 min; K'=3.7; Calculated monoisotopic mass ($C_{67}H_{89}BiN_{19}O_{16}$): 1751.56, found by ESI-MS: m/z=1752.3 [M+H]$^+$.

cyclo[i-yorn'([$^{nat}$Bi]DOTA-ra-(4-amino)benzoyl-)RNaIG ([$^{nat}$Bi]P5): HPLC (15% to 55% B in 15 min): $t_R$=9.1 min; K'=4.0; Calculated monoisotopic mass ($C_{68}H_{91}BiIN_{19}O_{16}$): 1765.57, found by ESI-MS: m/z=1767.5 [M+H]$^+$, 885.1 [M+2H]$^{2+}$.

2.5. Utilization of the Novel Linking Unit and Synthetic Description Thereof (F1-F4)

2.5.1 Synthesis of $^{18}$F-Labeling Precursors for Conjugation with the D-Orn-Side Chain of R or R1

TCP-resin is loaded with Fmoc-ABS-OH according to GP1 and the linear peptide chains are constructed according to standard Fmoc-procedure (GP2 and GP4, respectively). The Fmoc-deprotected N-terminus was converted to the respective azide according to a previously published procedure (Goddard-Borger and Stick, An efficient, inexpensive, and shelf-stable diazotransfer reagent: imidazole-1-sulfonyl azide hydrochloride. *Organic letters* 2007, 9 (19), 3797-3800). Briefly, imidazole-1-sulfonyl azide hydrochloride (1.5 eq.), $CuSO_4$ and DIPEA were added to the resin bound peptide at 4° C. Cooling was continued for 2 h and the resin bound peptide was shaken overnight at RT. The peptide was cleaved from the resin according to GP6 and freeze-dried overnight. N-propargyl-N,N-dimethyl-ammoniomethylboronylpinacolate (1.5 eq.) was combined with $KHF_2$ (3 M solution in water, 2.6 eq.) and 3.6 eq. HCl (4 M solution in water) and heated to 45° C. for 2 h. After addition of 1.2 mL of $NH_4OH$ (1 M in water) to adjust the pH, the solution was added to the azide-peptide. The mixture was heated to 55° C. for 15 h and purified using preparative HPLC. The purified fragment was coupled to R or R1, respectively employing HOBt, TBTU and DIPEA under standard conditions (GP4).

N-propargyl-N,N-dimethyl-ammoniomethylboronylpinacolate: o

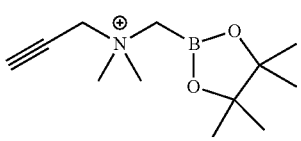

Chemical Formula: $C_{12}H_{23}BNO_2^+$
Exact Mass: 224.18

The synthesis was performed according to a published procedure with small modifications (Liu et al., Kit-like 18 F-labeling of RGD-19 F-Arytrifluroborate in high yield and at extraordinarily high specific activity with preliminary in vivo tumor imaging. *Nuclear medicine and biology* 2013, 40 (6), 841-849). Briefly, a dry round bottom flask was loaded with 53.8 µL (0.5 mmol, 1.0 eq.) of N,N-dimethylpropargylamine and 3 mL of dry DCM under a nitrogen atmosphere. 80.1 µL (0.5 mmol, 1.0 eq.) of iodomethyl-boronylpinacolate was added dropwise at RT. On stirring, the solution became cloudy and the white precipitated was filtered of after 2 h of vigorously stirring at 0° C. The precipitate was washed with ice cold diethyl ether two times and used without further purification. 104 mg (0.45 mmol, 93%) were collected as a white solid. Calculated monoisotopic mass ($C_{12}H_{23}BNO_2^+$): 224.18, found by ESI-MS: m/z=224.2 $[M]^+$.

$^1$H-NMR (400 MHz [Bruker], $CD_3CN$): δ [ppm]=1.31 (s, 12H), 3.17 (s, 6H), 3.21 (t, 2H), 3.23 (s, 1H), 4.22 (d, 2H).
$^{13}$C-NMR (101 MHz [Bruker], $CD_3CN$): δ [ppm]=24.89.

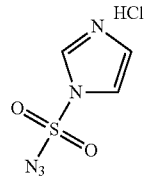

Chemical Formula: $C_3H_4ClN_5O_2S$
Exact Mass: 208.98 imidazole-1-sulfonyl azide hydrochloride: The synthesis was performed according to a published protocol (Hansen et al., Simple and efficient solid-phase preparation of azido-peptides. *Organic letters* 2012, 14 (9), 2330-2333). Briefly, sulfonylchloride (1.62 mL, 20.0 mmol, 1.0 eq.) was added drop-wise to an ice-cooled suspension of $NaN_3$ (1.3 g, 20.0 mmol, 1.0 eq.) in MeCN (20 mL) and the mixture was stirred overnight at RT. While stirring vigorously, imidazole (2.5 g, 38.0 mmol, 2.0 eq.) was added carefully to the ice-cooled solution and stirred for 3 h at RT. The solution was diluted with EtOAc (40 mL) and washed with water (2×40 mL) and saturated aqueous $NaHCO_3$ (2×20 mL), dried over $MgSO_4$ and filtered. A fresh solution of HCl in EtOH (obtained through drop-wise addition of AcCl (10.0 mL) to ice-cooled dry ethanol (25 mL)) was added slowly to the filtrate while stirring at 0° C. The crystallized product was filtered off on ice and the white crystals were washed with ice cold EtOAc to yield colorless needles (2.0 g, 9.5 mmol, 48%). The compound was used without further purification and stored at −20° C.

2.5.2 Synthetic Description of the Individual Compounds (F1-F4)

cyclo[i-yorn'(AMBF$_3$(methyl(1H-1,2,3-triazol-4-yl) 4-amino)benzoyl-)RNaIG] (F1) (Reference Compound)

R1 was coupled with AMBF$_3$-ABS-OH according to the general procedures GP4. The peptide was purified using preparative RP-HPLC.

cyclo[i-yorn'(AMBF$_3$(methyl(1H-1,2,3-triazol-4-yl) 4-amino)benzoyl-)RNaIG] (F1)

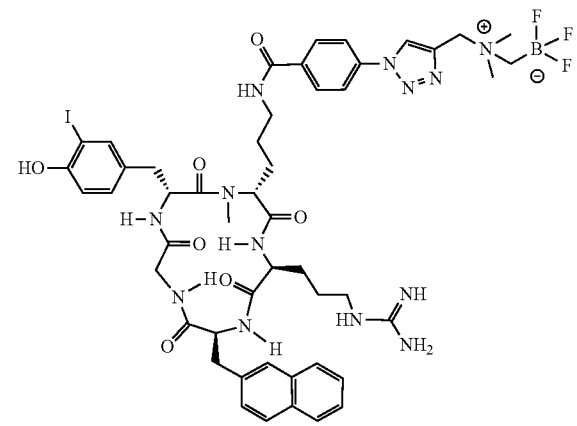

Chemical Formula: $C_{49}H_{60}BF_3IN_{13}O_7$
Exact Mass: 1137.38

HPLC (25-65% B in 15 min): $t_R$=10.3 min; MS (ESI): m/z=1138.6 $[M+H]^+$.

cyclo[i-yorn'(AMBF₃(methyl(1H-1,2,3-triazol-4-yl)-
vG-4-amino)benzoyl-)RNaIG] (F2) (Reference
Compound)

R1 was coupled with AMBF₃-vG-ABS-OH according to the general procedures GP4. The peptide was purified using preparative RP-HPLC.

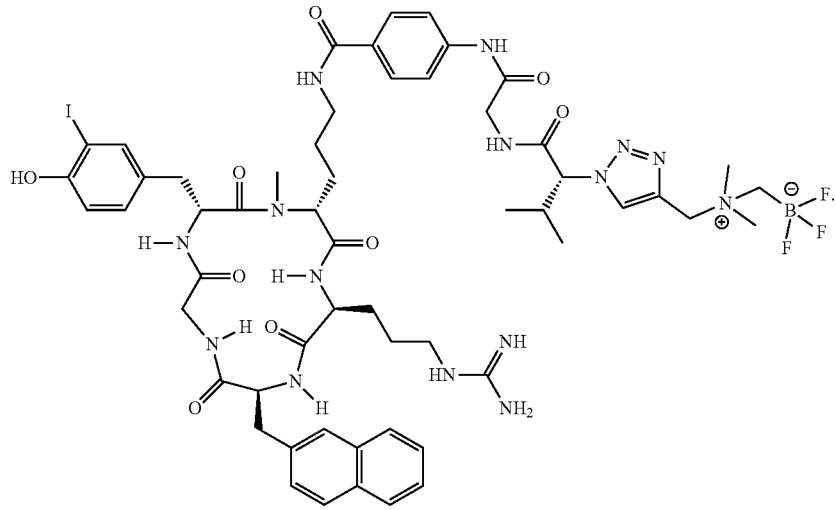

(F2)

cyclo[i-yorn'(AMBF₃(methyl(1H-1,2,3-triazol-4-yl)-vG-4-amino)benzoyl-)RNaIG]
Chemical Formula: $C_{56}H_{72}BF_3IN_{15}O_9$
Exact Mass: 1293.47
HPLC (25-65% B in 15 min): $t_R$ = 11.1 min; MS (ESI): m/z = 1294.8 [M + H]⁺.

cyclo[i-yorn'(AMBF₃(methyl(1H-1,2,3-triazol-4-yl)-
rG-4-amino)benzoyl-)RNaIG] (F3)

R1 was coupled with AMBF₃-rG-ABS-OH according to the general procedures GP4. The peptide was purified using preparative RP-HPLC.

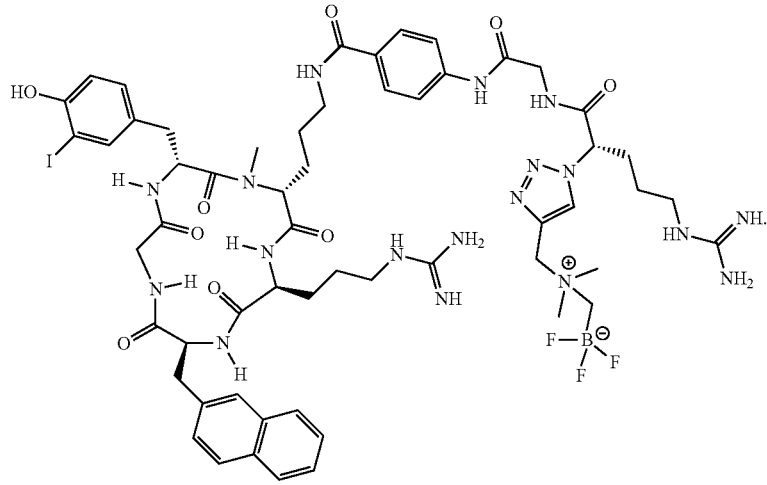

(F3)

cyclo[i-yorn'(AMBF₃(methyl(1H-1,2,3-triazol-4-yl)-rG-4-amino)benzoyl-)RNaIG]
Chemical Formula: $C_{57}H_{75}BF_3IN_{18}O_9$
Exact Mass: 1350.51
HPLC (15-65% B in 15 min): $t_R$ = 11.3 min;
MS (ESI): m/z = 1352.0 [M + H]⁺, 1374.0 [M + Na]⁺, 676.8 [M + 2H]²⁺ cyclo[-yorn'(AMBF$_3$(methyl(1H-1,2,3-triazol-4-yl)-rG-4-amino)benzoyl-)RNaIG] (F3b)

R was coupled with AMBF$_3$-rG-ABS-OH according to the general procedures GP4. The peptide was purified using preparative RP-HPLC.

3. Radiolabeling 3.1. Radioiodination

All peptides were radioiodinated using the IodoGen® method. Briefly, 100-200 μg of peptide were dissolved in 5-10 μL of DMSO. This solution was diluted with 0.5 mL TRIS iodination buffer (25 mM Tris.HCl, 0.4 M NaCl, pH

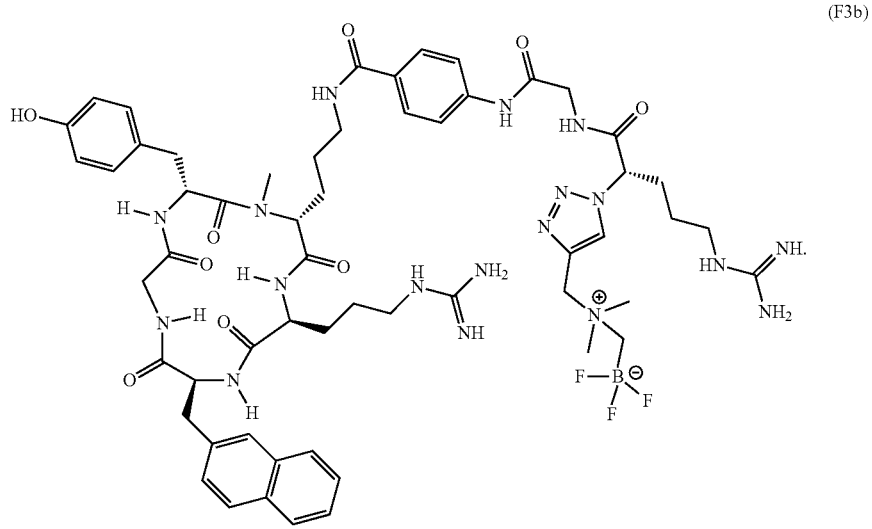

(F3b)

cyclo[-yorn'(AMBF$_3$(methyl(1H-1,2,3-triazol-4-yl)-rG-4-amino)benzoyl-)RNaIG]
Chemical Formula: C$_{57}$H$_{76}$BF$_3$N$_{18}$O$_9$
Exact Mass: 1224.61
HPLC (15-55% B in 15 min): t$_R$ = 8.7 min; MS (ESI): m/z = 1226.2 [M + H]$^+$ cyclo[i-yorn'(AMBF$_3$(methyl(1H-1,2,3-triazol-4-yl)-kG-4-amino)benzoyl-)RNaIG] (F4)

R1 was coupled with AMBF$_3$-rG-ABS-OH according to the general procedures GP4. The peptide was purified using preparative RP-HPLC.

7.5) and transferred to an Eppendorf reaction tube coated with 150 μg of IodoGen®. Upon addition of [$^{125}$I]NaI (18-20 MBq, Hartmann Analytic, Braunschweig, Germany) or [$^{123}$I]NaI (220 MBq, GE Healthcare, Braunschweig, Germany), the reaction vessel was briefly vortexed and the labeling reaction was allowed to proceed for 15 min at RT.

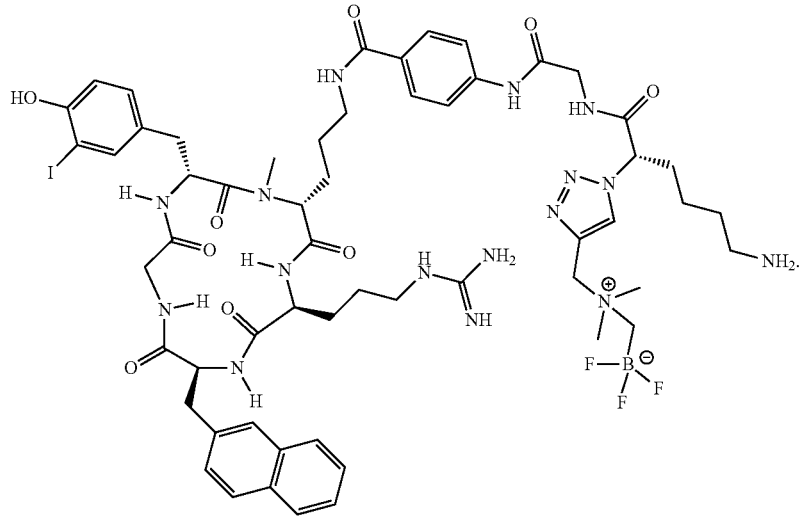

(F4)

cyclo[i-yorn'(AMBF$_3$(methyl(1H-1,2,3-triazol-4-yl)-rG-4-amino)benzoyl-)RNaIG]
Chemical Formula: C$_{57}$H$_{75}$BF$_3$IN$_{16}$O$_9$
Exact Mass: 1322.50
HPLC (15-55% B in 15 mn): t$_R$ = 12.1 min; MS(ESI): m/z = 1323.8 [M + H]$^+$ The peptide solution was then removed from the insoluble oxidizing agent. Separation of the labeled products from unlabeled precursor was achieved using gradient RP-HPLC. For in vitro binding studies, the HPLC product fraction was used as such and diluted to the required concentration using the respective assay medium. For biodistribution experiments, the respective product fraction was diluted with water and passed onto a SepPak Plus C-18 cartridge (Waters, Eschborn, Germany). The cartridge was washed with water, and the immobilized radiopeptide was then eluted using 1 ml of acetonitrile. The solvent was removed by bubbling an argon stream through the radioligand solution at 90° C. for 20 min. The radioiodinated peptides were then reconstituted to an activity concentration of app. 1 MBq/100 µL using PBS and were used as such for the in vivo animal study.

3.2. $^{68}$Ga-Labeling $^{68}$Ga was obtained by elution of a $^{68}$Ge/$^{68}$Ga generator with $SnO_2$ matrix (iTHEMBA LABS, South Africa) with 1 M HCl (5.5 mL) and immobilized on a strong cationic exchanger cartridge (SCX—Chromafix, size M, Macherey-Nagel, Duren, Germany).

For animal studies, $^{68}$Ga-pentixafor was prepared on a Gallelut$^+$ system in analogy to a previously published $^{68}$Ga labeling procedure (Notni, et al., TRAP, a powerful and versatile framework for gallium-68 radiopharmaceuticals. Chemistry 2011, 17 (52), 14718-22.) (SCINTOMICS GmbH, Germany). Briefly, $^{68}$Ga-generator eluate fractions (1.25 mL, 600-800 MBq, buffered to pH 3.3 with 900 µL of a solution of 14.4 g HEPES in 12 mL water) were reacted with 3.5 nmol of the respective DOTA-peptide (P1 to P5) for 5 min. The radiochemical purity was always >99% as confirmed by thin layer chromatography (TLC) and high performance liquid chromatography (HPLC). Addition of 1 mL PBS and concentration in vacuo to 1 mL total volume yielded solvent-free formulations with specific activities ranging from 100-150 MBq/nmol.

3.3. $^{177}$Lu-Labeling

For $^{177}$Lu-labeling, the respective DOTA-peptides (P1 to P5) were dissolved in water to yield a 100 µM solution. Of this solution, the required volume was added to $^{177}$LuCl$_3$ in 0.04 M HCl (itg Isotope Technologies Garching, Garching, Germany; activity concentration: 370 MBq/500 µl) to achieve a peptide-to-$^{177}$Lu-activity ratio of 0.75 nmol peptide per 25 MBq $^{177}$LuCl$_3$. To this mixture, 10 µL of 1 M NH$_4$OAc was added, together with water to yield 100 µL total reaction volume. The solution was heated to 95° C. for 30 min. Upon cooling, the radiochemical purity was determined using thin layer chromatography (TLC) (usually >98%). For in vitro and in vivo studies, the reaction mixture was diluted with PBS to the desired activity concentration and used as such for the experiments.

4. Determination of Lipophilicity

To a solution of app. 0.5 MBq of radiolabeled peptide in 500 µL of PBS (pH 7.4), 500 µL of octanol were added (n=6). Vials were vortexed vigorously for 3 min. To achieve quantitative phase separation, the vials were centrifuged at 14,600×g for 6 min in a Biofuge 15 (Heraeus Sepatech, Osterode, Germany). The activity concentrations in 100 µL-samples of both the aqueous and the organic phase were measured in a γ-counter. Both the partition coefficient Po$_w$, which is defined as the molar concentration ratio of a single species A between octanol and an aqueous phase at equilibrium, and log Po$_w$, which is an important parameter used to characterize lipophilicity of a compound, were calculated.

5. In Vitro Evaluation

For in vitro experiments, the following cell lines were used: Jurkat human T-cell leukemia cells, Ep-Myc1080 mouse B-cell lymphoma cells and Chem-1. Jurkat cells were cultivated in RPMI 1640 medium (Biochrom, Germany) containing 10% fetal calf serum (FCS) (Biochrom, Germany). The human CXCR4 expressing cell-line Chemicon's Wild-Type (Chem-1) was cultured in DMEM medium (Biochrom, Germany) supplemented with 10% FCS, 1% non-essential amino acids (Biochrom, Germany) and 1% HEPES (1M). The murine CXCR4 expressing cell line Ep-Myc1080 (Donnou et al., Murine models of B-cell lymphomas: promising tools for designing cancer therapies. Adv Hematol. 2012; 2012:701704) was grown in RPMI 1640 medium supplemented with 20% FCS, 1% non-essential amino acids (Biochrom, Germany) and 0.1% 2-Mercaptoethanol (Sigma-Aldrich, Germany). All cell lines were cultured at 37° C. in a humidified atmosphere with 5% $CO_2$ and passaged two to three times a week, depending on denseness of the cells.

Receptor Affinity Assays

Competition studies addressing the human CXCR4 were performed using CXCR4 positive Jurkat human T-cell leukemia cells and $^{125}$I-FC131 ($^{125}$I-2), addressing the murine CXCR4, Ep-Myc1080 mouse B-cell lymphoma cells and $^{125}$I-CPCR4.3 (Demmer et al. A Conformationally Frozen Peptoid Boosts CXCR4 Affinity and Anti-HIV Activity. *Angewandte Chemie International Edition.* 2012; 51:8110-8113) as the radioligand were utilized as described previously (Poschenrieder et al., The influence of different metal-chelate conjugates of pentixafor on the CXCR4 affinity. EJNMMI research. 2016; 6:1-8).

Internalization and Externalization Studies and Log P$_{(octanol/PBS)}$

Internalization and cell efflux studies of the respective ligands were performed using a previously published protocol (Poschenrieder et al., First 18F-Labeled Pentixafor-Based Imaging Agent for PET Imaging of CXCR4 Expression In Vivo. 2016). The distribution coefficients of the respective $^{68}$Ga- and $^{177}$Lu-labeled peptides in octanol and PBS buffer were determined applying the shake flask method as described previously (Weineisen et al., Synthesis and preclinical evaluation of DOTAGA-conjugated PSMA ligands for functional imaging and endoradiotherapy of prostate cancer. EJNMMI Research. 2014; 1:1-15).

6. In Vivo Experiments

Animal Model

All animal experiments were conducted in accordance with general animal welfare regulations in Germany (Deutsches Tierschutzgesetz, approval #55.2-1-54-2532 71-13). The human B-lymphoblast cell line Daudi was suspended (v/v) 1:1 in serum-free medium and Matrigel (BD Biosciences, Germany) and approximately 10$^7$ cells in 200 µL were inoculated subcutaneously on the right shoulder of 6 to 8 weeks old CB-17 SCID mice (Charles River, Germany). Tumors were grown for 2 to 4 weeks to reach 8 to 10 mm in diameter.

Biodistribution $^{177}$Lu-labeled CXCR4 ligands (approximately 5-10 MBq, 0.06 to 0.1 nmol) were injected into the tail vein of anesthetized animals. 6 h and 48 h after intravenous injection of approximately 0.15 mL of the radiolabeled peptide, the animals (n=4 for every time point) were sacrificed. The tissues and organs were weighted directly after preparation and the radioactivity was counted in a γ-counter. The % ID/g of each tissue was calculated and corrected with the activity found in the tail.

µPET Imaging

Imaging studies were performed at a Siemens Inveon small animal PET, followed by data analysis using the Inveon Research Workplace software. The animals were anesthetized with isoflurane and injected via the tail vein with 10 to 15 MBq (0.1 nmol) of tracer. Dynamic imaging was performed after on-bed injection for 1.5 h. Static images were recorded at 1 h p.i. with an acquisition time of 15 min. For competition experiments, animals were coinjected with 50 µg of AMD3100. Images were reconstructed using 3D ordered-subsets expectation maximum (OSEM3D) algorithm without scanner and attenuation correction.

EXAMPLE 2

Chemistry

The fully deprotected, cyclic CPCR4 binding scaffold (cyclo[D-Tyr-NMe-D-Orn-Arg-Nal-Gly](1), see FIG. 1) was synthesized in 63% yield on solid support as previously described with minor modifications (Demmer et al., Introduction of functional groups into peptides via N-alkylation. Organic letters. 2008; 10:2015-2018). All peptidic linker were synthesized via solid phase peptide synthesis using a standard Fmoc protocol. Subsequently, the peptides were cleaved from the resin (DCM/TFE/AcOH; v/v/v; 6/3/1) without deprotection of the side chains. After condensation with the cyclic binding motif 1, the chelator DOTA or DOTAGA-anhydride were coupled to the N-terminal free peptides in almost quantitative yields. By employing a novel, mild iodination method, the D-Tyr side chains of the respective peptides were selectively iodinated (FIG. 1) (Schottelius et al., An optimized strategy for the mild and efficient solution phase iodination of tyrosine residues in bioactive peptides. Tetrahedron Letters. 2015; 56:6602-6605). The $^{nat}Ga^{III}$ and $^{nat}Lu^{III}$ complexes of all tested compounds were prepared by incubation of the respective DOTA- or DOTAGA-peptide with an equimolar amount of aqueous $Ga(NO_3)_3$ or an 10-molar excess of $LuCl_3$ at 90° C. for 30 min.

Radiochemistry

Preparation of $^{68}$Ga-labeled peptides (5 nmol) was performed with a fully automated module (Scintomics, Germany) in high yields and specific activities of 100 to 120 GBq/µmol. $^{177}$Lu-labeled peptides were obtained after incubation of the respective DOTA-peptide (0.75 nmol) with 20 MBq of $^{177}LuCl_3$ in 1.0 M $NH_4OAc$ buffer (calculated to be 10% of total reaction volume) and heating to 95° C. for 30 min, which yielded in specific activities of 26 GBq/µmol.

EXAMPLE 3

CXCR4 Binding Affinity

The binding affinities ($IC_{50}$) of the respective $^{nat}Lu$ and $^{nat}Ga$ derivatives towards the human and murine CXCR4 (Table 1a) were determined in a competitive binding assay using Jurkat human T-cell leukemia cells or Eµ-Myc1080 mouse B-cell lymphoma cells (4.0 and 2.0*10$^5$ cells/well, 2 h, RT) and $^{125}$I-2 or $^{125}$I-CPCR4.3 (0.1 nM) as the radioligand. To be able to assess the effect of structural modifications in the SAR study on CXCR4 binding affinity, data for $^{nat}$Ga-pentixafor ($^{nat}$Ga-3) and $^{nat}$Lu-pentixather ($^{nat}$Lu-4) are also included in Table 1a.

TABLE 1a

Structural modifications of synthesized compounds and binding affinity to human and murine CXCR4 ($IC_{50}$) of $^{nat}Lu$ and $^{nat}Ga$-complexes (see FIG. 1).

|  | $R_1$ | $Xaa_1$ | $Xaa_2$ | $R_2$ | $IC_{50}$ [nM] for $^{nat}Lu$-complexes and human CXCR4 | $IC_{50}$ [nM] for $^{nat}Ga$-complexes and human CXCR4 | $mIC_{50}$ [nM] $^{nat}Lu$ complexes and murine CXCR4 |
|---|---|---|---|---|---|---|---|
| 2 | — | — | — | — | 13.1 ± 5.1 | — | 119 ± 69 |
| 3 | H | —[a] | — | DOTA | 41 ± 12 | 24.8 ± 2.5[a] | >1000 |
| 4 | I | —[a] | — | DOTA | 14.6 ± 1.0 | 6.1 ± 1.5 | 567 ± 62 |
| 5 | I | — | — | DOTA | 12.5 ± 3.2 | 282 ± 90 | — |
| 6 | I | — | — | DOTAGA | 28.3 ± 9 | 14.4 ± 0.3 | — |
| 7 | I | Gly | — | DOTA | 5.9 ± 0.3 | 7.9 ± 1.1 | — |
| 8 | I | Gly | — | DOTAGA | 38.8 ± 1.3 | 47.4 ± 8.1 | — |
| P1 | I | D-Asp | — | DOTA | 106 ± 10 | — | — |
| P2 | I | Gly | D-Dap[b] | DOTA | 3.5 ± 0.3 | 3.6 ± 0.7 | — |
| P3b | H | Gly | D-Lys | DOTA | 8.0 ± 3.1 | 8.9 ± 3.8 | — |
| P3 | I | Gly | D-Lys | DOTA | 3.6 ± 1.1 | 2.4 ± 0.1 | 61.4 ± 17 |
| P4b | H | Gly | D-Arg | DOTA | 5.4 ± 1.6 | 9.7 ± 2.8 | — |
| P4 | I | Gly | D-Arg | DOTA | 2.1 ± 0.3 | 1.4 ± 0.2 | 37.1 ± 2.9 |
| P5b | H | D-Ala | D-Arg | DOTA | 1.5 ± 0.1 | 0.4 ± 0.1 | — |
| P5 | I | D-Ala | D-Arg | DOTA | 1.7 ± 0.6 | 2.6 ± 1.0 | 48.5 ± 0.5 |

Binding assays were performed using Jurkat cells (400,000/well) and ([$^{125}$I]FC131) (c = 0.1 nM) as the radioligand for hCXCR4 and Eµ-Myc1080 mouse B-cell lymphoma cells and [$^{125}$I]CPCR4.3 as radioligand. Cells were incubated in HBSS (1% BSA) at RT for 2 h. Data are expressed as mean ± SD (n = 3).
[a]4-aminobenzoic acid spacer is substituted by 4-aminomethylbenzoic acid (see FIG. 1 (5-16),
[b](R)-2,3-diaminopropanoic acid.

As demonstrated by six-fold enhanced binding affinities towards hCXCR4 (7 vs 8), the chelator DOTA is preferred over DOTAGA and an additional glycine in the linker beneficially contributes to the binding affinity (12.5±3.2 nM for $^{nat}Lu$-5 vs. 5.9±0.3 nM for $^{nat}Lu$-7, respectively). Supplemental insertion of cationic amino acids in the linker further improves the binding affinities almost two-fold with 3.5±0.3 nM for $^{nat}Lu$-P2. Mutation of the cationic amino acid at that position in combination with a final optimization step wherein glycine was substituted with D-alanine (P5), led to an additional almost two-fold increase in affinity compared to P2 (1.7±0.6 nM for $^{nat}Lu$-P5). Finally, the optimized "linking unit" also allowed the utilization of the non-iodinated scaffold (1), which surprisingly also resulted in enhanced binding affinity (1.5±0.1 nM and 0.4±0.1 nM for $^{nat}Lu$-P5b and $^{nat}Ga$-P5b, respectively). Additionally, $^{nat}Lu$-P4 and $^{nat}Lu$-P5 showed dramatically improved binding affinities towards the murine receptor with 37.1±2.9 nM for $^{nat}Lu$-P4 and 48.5±0.5 nM for $^{nat}Lu$-P5 in comparison to 567±62 nM for $^{nat}Lu$-4.

Further affinity data for P1, P2, P3, P3b, P4, P4b, P5 and P5b and further compounds are given in Tables 1b to 1d below.

TABLE 1b

Binding affinities (IC$_{50}$ in nM) of novel CXCR4 ligands to human CXCR4 (hCXCR4). Affinities were determined using Jurkat human T-cell leukemia cells (400.000 cells/sample) and [$^{125}$I]FC-131 as the radioligand. Each experiment was performed in triplicate, and results are means ± SD from three separate experiments.

| c(iodoyorn'(R$^1$)RNalG) R$^1$ = Metal complexes | compound | IC$_{50}$ [nM] to hCXCR4 [$^{nat}$Ga] | IC$_{50}$ [nM] to hCXCR4 [$^{nat}$Lu] | IC$_{50}$ [nM] to hCXCR4 [$^{nat}$Y] | IC$_{50}$ [nM] to hCXCR4 [$^{nat}$Bi] |
|---|---|---|---|---|---|
| [structure] | P1 | — | 106 ± 10 | — | — |
| [structure] | P2 | 3.6 ± 0.7 | 3.5 ± 0.3 | 4.1 ± 1.3 | 3.5 ± 0.4 |
| [structure] | P3 | 2.4 ± 0.1 | 3.6 ± 1.1 | 2.4 ± 0.2 | 38 ± 25 |

TABLE 1b-continued

Binding affinities (IC$_{50}$ in nM) of novel CXCR4 ligands to human CXCR4 (hCXCR4). Affinities were determined using Jurkat human T-cell leukemia cells (400.000 cells/sample) and [$^{125}$I]FC-131 as the radioligand. Each experiment was performed in triplicate, and results are means ± SD from three separate experiments.

| Structure | Compound | | | | |
|---|---|---|---|---|---|
| (structure shown) | P4 | 1.4 ± 0.2 | 2.1 ± 0.3 | 2.1 ± 0.3 | 2.9 ± 0.1 |
| (structure shown) | P5 | 2.6 ± 1.0 | 1.7 ± 0.6 | 1.6 ± 0.5 | 1.8 ± 0.8 |

| c(yorn'(R$^1$)RNalG) R$^1$ = Metal complexes | compound | IC$_{50}$ [nM] to hCXCR4 [$^{nat}$Ga] | IC$_{50}$ [nM] to hCXCR4 [$^{nat}$Lu] | IC$_{50}$ [nM] to hCXCR4 [$^{nat}$Y] | IC$_{50}$ [nM] to hCXCR4 [$^{nat}$Bi] |
|---|---|---|---|---|---|
| (structure shown) | P3b | 8.9 ± 3.8 | 8.0 ± 3.1 | 6.3 ± 2.5 | — |

TABLE 1b-continued

Binding affinities (IC$_{50}$ in nM) of novel CXCR4 ligands to human CXCR4 (hCXCR4). Affinities were determined using Jurkat human T-cell leukemia cells (400.000 cells/sample) and [$^{125}$I]FC-131 as the radioligand. Each experiment was performed in triplicate, and results are means ± SD from three separate experiments.

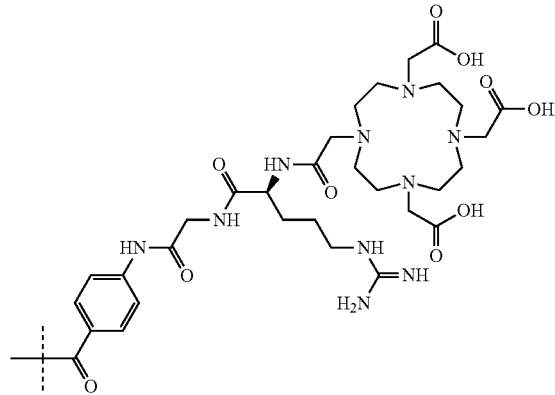

P4b    9.7 ± 2.8    5.4 ± 1.6    8.7 ± 2.9    —

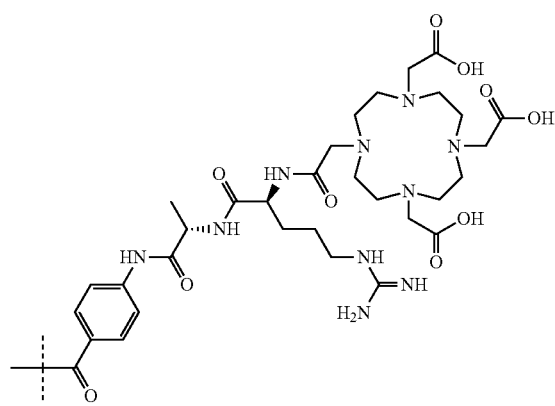

P5b    0.4 ± 0.1    1.5 ± 0.1    0.3 ± 0.1    —

| c(iodoyorn'(R$^1$)RNalG) R$^1$ = 18F-labeling precursors | compound | IC$_{50}$ [nM] to hCXCR4 |
|---|---|---|
| 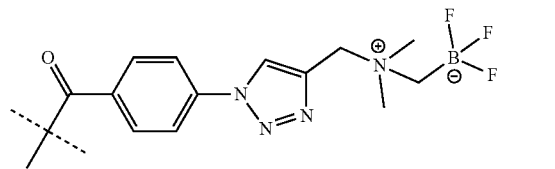 | F1 | 134.3 ± 47 |
| 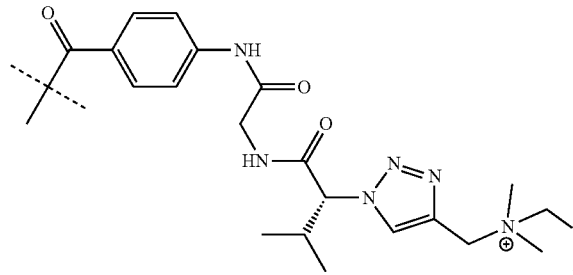 | F2 | 65.2 ± 10 |

TABLE 1b-continued

Binding affinities (IC$_{50}$ in nM) of novel CXCR4 ligands to human CXCR4 (hCXCR4). Affinities were determined using Jurkat human T-cell leukemia cells (400.000 cells/sample) and [$^{125}$I]FC-131 as the radioligand. Each experiment was performed in triplicate, and results are means ± SD from three separate experiments.

| Structure | Compound | IC$_{50}$ [nM] |
|---|---|---|
| (structure shown) | F3 | 2.9 ± 0.9 |
| (structure shown) | F4 | 3.8 ± 0.9 |

| c(yorn'(R$^1$)RNalG) R$^1$ = $^{18}$F-labeling precursors | compound | IC$_{50}$ [nM] to hCXCR4 |
|---|---|---|
| | F3b | 2.4 ± 0.8 |

TABLE 1c

Binding affinities (IC$_{50}$ in nM) of novel CXCR4 ligands to mouse CXCR4 (mCXCR4). Affinities were determined using Eµ-Myc1080 mouse B-cell lymphoma (200.000 cells/sample), and [$^{125}$I]CPCR4.3[8] as the radioligand. Each experiment was performed in triplicate, and results are means ± SD from three separate experiments.

| c(iodoyorn'(R$^1$)RNalG) R$^1$= | compound | IC$_{50}$ [nM] to mCXCR4 |
|---|---|---|
| | 12 = P3 | 37.1 ± 2.9 |
| | 14 = P4 | 48.5 ± 0.5 |
| | 16 = P5 | 61.4 ± 17 |

TABLE 1d

| cyclo[tyr-N(Me)orn(S)-Arg-Nal-Gly]<br>S = orn side chain modification | compound | IC$_{50}$ [nM] to hCXCR4 | logP |
|---|---|---|---|
| $^{19}$F-labeled precursor (FBOA-analog) | | | |
| [structure] | F5 | 4.6 ± 0.7 | |
| $^{99m}$Tc-labeling precursors and ReO-reference cpd. | | | |
| [structure] | T1 | 22.9 ± 3.9 | — |
| [structure] | T1b | 17.0 ± 3.7 | −1.37 |
| [structure] | T2 | 85.7 ± 5.1 | −2.2 |

TABLE 1d-continued cyclo[tyr-N(Me)orn(S)-Arg-Nal-Gly]
S = orn side chain modification

| compound | IC$_{50}$ [nM] to hCXCR4 | logP |
|---|---|---|
| T3 | 18.8 ± 8.5 | −1.5 |
| T4 | 213 ± 22 | −2.2 |

Internalization and Externalization Studies

The internalization and cell efflux kinetics of the most affine peptides $^{177}$Lu-P5b and $^{177}$Lu-P5 were determined using hCXCR4$^+$ Chem_1 cells (1.25×10$^5$ cells/well) at 37° C. (FIG. 2). The final peptide concentration in the assay was adjusted to 1.0 nM to obtain reasonable count rates for assay evaluation. To differentiate specific binding to CXCR4 from non-specific binding, the experiments were always carried out in the absence and in the presence of AMD3100 (c=100 µM mol/L) (40). The $^{177}$Lu-labeled peptides were measured in the same assay together with $^{177}$Lu-pentixather ($^{177}$Lu-4) for direct comparison. For externalization kinetics, the respective $^{177}$Lu-labeled peptides were allowed to internalize into the cells for 120 min before start of the experiment. The upper part of FIG. 2 shows the internalization kinetics of $^{177}$Lu-P5b and $^{177}$Lu-P5 over 60 min in comparison to $^{177}$Lu-4. In concordance with the enhanced binding affinities, the specific internalized activity of $^{177}$Lu-P5b and $^{177}$Lu-P5 was 21.2±1.9% and 36.7±1.0% in comparison to 3.8±1.3% for $^{177}$Lu-4. Consequently, the introduction of a peptidic spacer enhanced the internalization of the novel CXCR4 ligands almost 10-fold. The lower panel of FIG. 2 shows the externalization kinetics of $^{177}$Lu-P5b, $^{177}$Lu-P5 and $^{177}$Lu-4. After 60 min of incubation in tracer free medium (allowing reinternalization of externalized tracer), over 85% of the initially internalized activity of $^{177}$Lu-P5b and $^{177}$Lu-P5 remained in the cells. $^{177}$Lu-4, by contrast, followed a typical efflux kinetic, which resulted in only 37% of initial activity still cell associated after 60 min.

Determination of Lipophilicity

Lipophilicity was measured using the shake flask method. The logarithm of the partition coefficient P, where P is the ratio of activity distribution of the respective $^{68}$Ga/$^{177}$Lu-labeled peptide in n-octanol and PBS are listed in Table 2. The novel peptides all showed enhanced hydrophilicity. Among all tested compounds, $^{68}$Ga-15 was the most hydrophilic compound.

TABLE 2

Lipophilicity of the radiolabeled ligands (logP(o/w); distribution coefficient in n-octanol/PBS)

| CXCR4 ligand | logP$_{(o/w)}$ |
|---|---|
| $^{68}$Ga-3 | −2.90 ± 0.08 |
| $^{68}$Ga-P5b | −3.58 ± 0.06 |
| $^{68}$Ga-P5 | −3.29 ± 0.02 |
| $^{177}$Lu-4 | −1.80 ± 0.20 |
| $^{117}$Lu-P5b | −2.96 ± 0.13 |
| $^{177}$Lu-P5 | −2.75 ± 0.04 |

Data are expressed as mean ± SD (n = 6).

Biodistribution Studies

Comparative biodistribution data for $^{177}$Lu-P5b, $^{177}$Lu-P5 and $^{177}$Lu-4 (each 0.1 to 0.2 nmol) 6 h and 48 h after injection in Daudi lymphoma-bearing SCID mice (n=4) are summarized in FIG. 3 (6 h p.i.) and FIG. 4 (48 h p.i.). As depicted in FIG. 3, all $^{177}$Lu-labeled peptides showed low accumulation in non-target tissue and rapid renal clearance. However, $^{177}$Lu-P5 showed elevated liver uptake as well as enhanced uptake in murine CXCR4 associated tissue like spleen, lungs and bone. Furthermore, enhanced kidney accumulation was observed for $^{177}$Lu-P5b (7.1±2.0% ID/g). Most importantly, the increased CXCR4-mediated internalization and binding affinity of $^{177}$Lu-P5b and $^{177}$Lu-P5, compared with $^{177}$Lu-4, was well reflected by an enhanced uptake in the CXCR4-positive tumor with 12.5±2.6% ID/g for $^{177}$Lu-P5b and 13.6±3.3% ID/g for $^{177}$Lu-P5 in comparison to 6.8±0.7% ID/g for $^{177}$Lu-4, respectively. 48 h after injection, tumor uptake, tumor/muscle ratios and tumor/blood ratios of $^{177}$Lu-P5b reached values of 8.8% ID/g, 412 and 948 and 3.2% ID/g, 85 and 201 for $^{177}$Lu-4, respectively (FIG. 4).

Small-Animal PET Imaging

As demonstrated with the PET images in FIG. 5 of Daudi lymphoma-bearing SCID mice 60 min after injection, $^{68}$Ga-P5b and $^{68}$Ga-P5 primarily accumulate in the tumor and show fast, renal excretion. In agreement with the biodistribution data, the novel ligands exhibit slightly enhanced liver uptake and for $^{68}$Ga-P5b an enhanced retention in the kidneys. The tracer uptake into tumor is specific and CXCR4 mediated, as illustrated by the competition experiment using 50 μg of AMD3100 (FIG. 5). The time-activity curves (FIG. 6) derived from dynamic PET data reveal fast and constantly increasing uptake kinetics of both tracer in the tumor over the 1.5 h observation period. In contrast to $^{68}$Ga-P5b, $^{68}$Ga-P5 showed a faster washout from blood (region of interest over the heart), but an almost identical clearance from the liver.

FURTHER REFERENCES

1. Zlotnik A, Yoshie O. Chemokines: a new classification system and their role in immunity. Immunity 2000; 12:121-127.
2. Domanska U M, Kruizinga R C, Nagengast W B, Timmer-Bosscha H, Huls G, de Vries E G, et al. A review on CXCR4/CXCL12 axis in oncology: no place to hide. European journal of cancer 2013; 49:219-230.
3. Feng Y, Broder C C, Kennedy P E, Berger E A. HIV-1 entry cofactor: functional cDNA cloning of a seven-transmembrane, G protein-coupled receptor. Science 1996; 272:872-877.
4. Nagasawa T, Hirota S, Tachibana K, Takakura N, Nishikawa S-i, Kitamura Y, et al. Defects of B-cell lymphopoiesis and bone-marrow myelopoiesis in mice lacking the CXC chemokine PBSF/SDF-1. Nature 1996; 382:635-638.
5. Loetscher P, Moser B, Baggiolini M. Chemokines and their receptors in lymphocyte traffic and HIV infection. Advances in immunology 2000; 74:127-180.
6. Aiuti A, Webb I, Bleul C, Springer T, Gutierrez-Ramos J. The chemokine SDF-1 is a chemoattractant for human CD34+ hematopoietic progenitor cells and provides a new mechanism to explain the mobilization of CD34+ progenitors to peripheral blood. The Journal of experimental medicine 1997; 185:111-120.
7. Ma Q, Jones D, Borghesani P R, Segal R A, Nagasawa T, Kishimoto T, et al. Impaired B-lymphopoiesis, myelopoiesis, and derailed cerebellar neuron migration in CXCR4- and SDF-1-deficient mice. Proc Natl Acad Sci USA 1998; 95:9448-9453.
8. Nagafuchi Y, Shoda H, Sumitomo S, Nakachi S, Kato R, Tsuchida Y, et al. Immunophenotyping of rheumatoid arthritis reveals a linkage between HLA-DRB1 genotype, CXCR4 expression on memory CD4(+) T cells, and disease activity. Sci Rep 2016; 6:29338.
9. Galkina E, Ley K. Immune and inflammatory mechanisms of atherosclerosis (*). Annu Rev Immunol 2009; 27:165-197.
10. Schober A, Bernhagen J, Weber C. Chemokine-like functions of MIF in atherosclerosis. J Mol Med (Berl) 2008; 86:761-770.
11. Burger J A, Burger M, Kipps T J. Chronic lymphocytic leukemia B cells express functional CXCR4 chemokine receptors that mediate spontaneous migration beneath bone marrow stromal cells. Blood 1999; 94:3658-3667.
12. Muller A, Homey B, Soto H, Ge N, Catron D, Buchanan M E, et al. Involvement of chemokine receptors in breast cancer metastasis. nature 2001; 410:50-56.
13. Burger J A, Kipps T J. CXCR4: a key receptor in the crosstalk between tumor cells and their microenvironment. Blood 2006; 107:1761-1767.
14. Chatterjee S, Azad B B, Nimmagadda S. The intricate role of CXCR4 in cancer. Advances in cancer research 2014; 124:31.
15. Brave M, Farrell A, Ching Lin S, Ocheltree T, Pope Miksinski S, Lee S L, et al. FDA review summary: Mozobil in combination with granulocyte colony-stimulating factor to mobilize hematopoietic stem cells to the peripheral blood for collection and subsequent autologous transplantation. Oncology 2010; 78:282-288.
16. Liu T, Li X, You S, Bhuyan S S, Dong L. Effectiveness of AMD3100 in treatment of leukemia and solid tumors: from original discovery to use in current clinical practice. Exp Hematol Oncol 2015; 5:19.
17. Taromi S, Kayser G, Catusse J, von Elverfeldt D, Reichardt W, Braun F, et al. CXCR4 antagonists suppress small cell lung cancer progression. Oncotarget 2016; 7:85185-85195.
18. Bodart V, Anastassov V, Darkes M C, Idzan S R, Labrecque J, Lau G, et al. Pharmacology of AMD3465: a small molecule antagonist of the chemokine receptor CXCR4. Biochem Pharmacol 2009; 78:993-1000.
19. Ling X, Spaeth E, Chen Y, Shi Y, Zhang W, Schober W, et al. The CXCR4 antagonist AMD3465 regulates oncogenic signaling and invasiveness in vitro and prevents breast cancer growth and metastasis in vivo. PLoS One 2013; 8:e58426.
20. Liang Z, Zhan W, Zhu A, Yoon Y, Lin S, Sasaki M, et al. Development of a unique small molecule modulator of CXCR4. PLoS One 2012; 7:e34038.
21. Wong D, Kandagatla P, Korz W, Chinni S R. Targeting CXCR4 with CTCE-9908 inhibits prostate tumor metastasis. BMC Urol 2014; 14:12.
22. Beider K, Darash-Yahana M, Blaier 0, Koren-Michowitz M, Abraham M, Wald H, et al. Combination of imatinib with CXCR4 antagonist BKT140 overcomes the protective effect of stroma and targets CML in vitro and in vivo. Mol Cancer Ther 2014; 13:1155-1169.
23. Fahham D, Weiss I D, Abraham M, Beider K, Hanna W, Shlomai Z, et al. In vitro and in vivo therapeutic efficacy of CXCR4 antagonist BKT140 against human non-small cell lung cancer. J Thorac Cardiovasc Surg 2012; 144: 1167-1175 e1161.
24. Peled A, Abraham M, Avivi I, Rowe J M, Beider K, Wald H, et al. The high-affinity CXCR4 antagonist BKT140 is safe and induces a robust mobilization of human CD34+ cells in patients with multiple myeloma. Clin Cancer Res 2014; 20:469-479.
25. Karpova D, Dauber K, Spohn G, Chudziak D, Wiercinska E, Schulz M, et al. The novel CXCR4 antagonist POL5551 mobilizes hematopoietic stem and progenitor cells with greater efficiency than Plerixafor. Leukemia 2013; 27:2322-2331.
26. Sison E A, Magoon D, Li L, Annesley C E, Romagnoli B, Douglas G J, et al. POL5551, a novel and potent CXCR4 antagonist, enhances sensitivity to chemotherapy in pediatric ALL. Oncotarget 2015; 6:30902-30918.
27. Xiang J, Hurchla M A, Fontana F, Su X, Amend S R, Esser A K, et al. CXCR4 Protein Epitope Mimetic Antagonist POL5551 Disrupts Metastasis and Enhances Chemotherapy Effect in Triple-Negative Breast Cancer. Mol Cancer Ther 2015; 14:2473-2485.
28. Azad B B, Chatterjee S, Lesniak W G, Lisok A, Pullambhatla M, Bhujwalla Z M, et al. A fully human CXCR4 antibody demonstrates diagnostic utility and therapeutic efficacy in solid tumor xenografts. Oncotarget 2016; 7:12344-12358.
29. Peng S-B, Zhang X, Paul D, Kays L M, Ye M, Vaillancourt P, et al. Inhibition of CXCR4 by LY2624587, a Fully Humanized Anti-CXCR4 Antibody Induces Apoptosis of Hematologic Malignancies. PloS one 2016; 11:e0150585.

30. Ramsey D M, McAlpine S R. Halting metastasis through CXCR4 inhibition. Bioorg Med Chem Lett 2013; 23:20-25.
31. Cho B S, Zeng Z, Mu H, Wang Z, Konoplev S, McQueen T, et al. Antileukemia activity of the novel peptidic CXCR4 antagonist LY2510924 as monotherapy and in combination with chemotherapy. Blood 2015; 126:222-232.
32. Peng S B, Zhang X, Paul D, Kays L M, Gough W, Stewart J, et al. Identification of LY2510924, a novel cyclic peptide CXCR4 antagonist that exhibits antitumor activities in solid tumor and breast cancer metastatic models. Mol Cancer Ther 2015; 14:480-490.
33. Di Maro S, Di Leva F S, Trotta A M, Brancaccio D, Portella L, Aurilio M, et al. Structure-Activity Relationships and Biological Characterization of a Novel, Potent, and Serum Stable C-X-C Chemokine Receptor Type 4 (CXCR4) Antagonist. J Med Chem 2017; 60:9641-9652.
34. Di Maro S, Trotta A M, Brancaccio D, Di Leva F S, La Pietra V, Ierano C, et al. Exploring the N-Terminal Region of C-X-C Motif Chemokine 12 (CXCL12): Identification of Plasma-Stable Cyclic Peptides As Novel, Potent C-X-C Chemokine Receptor Type 4 (CXCR4) Antagonists. J Med Chem 2016; 59:8369-8380.
35. Ierano C, Portella L, Lusa S, Salzano G, D'Alterio C, Napolitano M, et al. CXCR4-antagonist Peptide R-liposomes for combined therapy against lung metastasis. Nanoscale 2016; 8:7562-7571.
36. Fontanella R, Pelagalli A, Nardelli A, D'Alterio C, Ierano C, Cerchia L, et al. A novel antagonist of CXCR4 prevents bone marrow-derived mesenchymal stem cell-mediated osteosarcoma and hepatocellular carcinoma cell migration and invasion. Cancer Lett 2016; 370:100-107.
37. Santagata S, Napolitano M, D'Alterio C, Desicato S, Maro S D, Marinelli L, et al. Targeting CXCR4 reverts the suppressive activity of T-regulatory cells in renal cancer. Oncotarget 2017; 8:77110-77120.
38. George G P, Stevens E, Aberg O, Nguyen Q-D, Pisaneschi F, Spivey A C, et al. Preclinical evaluation of a CXCR4-specific $^{68}$Ga-labelled TN14003 derivative for cancer PET imaging. Bioorganic & medicinal chemistry 2014; 22:796-803.
39. Yan X, Niu G, Wang Z, Yang X, Kiesewetter D O, Jacobson O, et al. Al [$^{18}$F]NOTA-T140 Peptide for Non-invasive Visualization of CXCR4 Expression. Molecular Imaging and Biology 2015:1-8.
40. Jacobson O, Weiss I D, Kiesewetter D O, Farber J M, Chen X. PET of tumor CXCR4 expression with 4-$^{18}$F-T140. Journal of Nuclear Medicine 2010; 51:1796-1804.
41. Wang Z, Zhang M, Wang L, Wang S, Kang F, Li G, et al. Prospective Study of (68)Ga-NOTA-NFB: Radiation Dosimetry in Healthy Volunteers and First Application in Glioma Patients. Theranostics 2015; 5:882-889.
42. Buckle T, van Berg N S, Kuil J, Bunschoten A, Oldenburg J, Borowsky A D, et al. Non-invasive longitudinal imaging of tumor progression using an (111)indium labeled CXCR4 peptide antagonist. Am J Nucl Med Mol Imaging 2012; 2:99-109.
43. Kuil J, Buckle T, Oldenburg J, Yuan H, Borowsky A D, Josephson L, et al. Hybrid peptide dendrimers for imaging of chemokine receptor 4 (CXCR4) expression. Mol Pharm 2011; 8:2444-2453.
44. Kuil J, Buckle T, Yuan H, van den Berg N S, Oishi S, Fujii N, et al. Synthesis and evaluation of a bimodal CXCR4 antagonistic peptide. Bioconjug Chem 2011; 22:859-864.
45. Nishizawa K, Nishiyama H, Oishi S, Tanahara N, Kotani H, Mikami Y, et al. Fluorescent imaging of high-grade bladder cancer using a specific antagonist for chemokine receptor CXCR4. Int J Cancer 2010; 127:1180-1187.
46. Portella L, Vitale R, De Luca S, D'Alterio C, Ierano C, Napolitano M, et al. Preclinical development of a novel class of CXCR4 antagonist impairing solid tumors growth and metastases. PloS one 2013; 8:e74548.
47. Fujii N, Oishi S, Hiramatsu K, Araki T, Ueda S, Tamamura H, et al. Molecular-size reduction of a potent CXCR4-chemokine antagonist using orthogonal combination of conformation- and sequence-based libraries. Angew Chem Int Ed Engl 2003; 42:3251-3253.
48. Tamamura H, Araki T, Ueda S, Wang Z, Oishi S, Esaka A, et al. Identification of novel low molecular weight CXCR4 antagonists by structural tuning of cyclic tetra-peptide scaffolds. Journal of medicinal chemistry 2005; 48:3280-3289.
49. Tamamura H, Esaka A, Ogawa T, Araki T, Ueda S, Wang Z, et al. Structure-activity relationship studies on CXCR4 antagonists having cyclic pentapeptide scaffolds. Org. Biomol. Chem. 2005; 3:4392-4394.
50. Tanaka T, Nomura W, Narumi T, Esaka A, Oishi S, Ohashi N, et al. Structure-activity relationship study on artificial CXCR4 ligands possessing the cyclic pentapeptide scaffold: the exploration of amino acid residues of pentapeptides by substitutions of several aromatic amino acids. Organic & biomolecular chemistry 2009; 7:3805-3809.
51. Inokuchi E, Oishi S, Kubo T, Ohno H, Shimura K, Matsuoka M, et al. Potent CXCR4 antagonists containing amidine type Peptide bond isosteres. ACS Med Chem Lett 2011; 2:477-480.
52. Kobayashi K, Oishi S, Hayashi R, Tomita K, Kubo T, Tanahara N, et al. Structure-activity relationship study of a CXC chemokine receptor type 4 antagonist, FC131, using a series of alkene dipeptide isosteres. J Med Chem 2012; 55:2746-2757.
53. Narumi T, Hayashi R, Tomita K, Kobayashi K, Tanahara N, Ohno H, et al. Synthesis and biological evaluation of selective CXCR4 antagonists containing alkene dipeptide isosteres. Organic & biomolecular chemistry 2010; 8:616-621.
54. Demmer O, Dijkgraaf I, Schottelius M, Wester H-J, Kessler H. Introduction of functional groups into peptides via N-alkylation. Organic letters 2008; 10:2015-2018.
55. Demmer O, Dijkgraaf I, Schumacher U, Marinelli L, Cosconati S, Gourni E, et al. Design, synthesis, and functionalization of dimeric peptides targeting chemokine receptor CXCR4. Journal of medicinal chemistry 2011; 54:7648-7662.
56. Demmer O, Gourni E, Schumacher U, Kessler H, Wester H J. PET imaging of CXCR4 receptors in cancer by a new optimized ligand. ChemMedChem 2011; 6:1789-1791.
57. Gourni E, Demmer O, Schottelius M, D'Alessandria C, Schulz S, Dijkgraaf I, et al. PET of CXCR4 expression by a 68Ga-labeled highly specific targeted contrast agent. Journal of Nuclear Medicine 2011; 52:1803-1810.
58. Wester H J, Keller U, Schottelius M, Beer A, Philipp-Abbrederis K, Hoffmann F, et al. Disclosing the CXCR4 expression in lymphoproliferative diseases by targeted molecular imaging. Theranostics 2015; 5:618.
59. Philipp-Abbrederis K, Herrmann K, Knop S, Schottelius M, Eiber M, Luckerath K, et al. In vivo molecular imaging of chemokine receptor CXCR4 expression in patients with advanced multiple myeloma. EMBO Mol Med 2015; 7:477-487.

60. Lapa C, Schreder M, Schirbel A, Samnick S, Kortum K M, Herrmann K, et al. [$^{68}$Ga]Pentixafor-PET/CT for imaging of chemokine receptor CXCR4 expression in multiple myeloma—Comparison to [$^{18}$F]FDG and laboratory values. Theranostics 2017; 7:205-212.
61. Avanesov M, Karul M, Derlin T. [$^{68}$Ga]pentixafor PET: clinical molecular imaging of chemokine receptor CXCR4 expression in multiple myeloma]. Radiologe 2015; 55:829-831.
62. Herhaus P, Habringer S, Philipp-Abbrederis K, Vag T, Gerngross C, Schottelius M, et al. Targeted positron emission tomography imaging of CXCR4 expression in patients with acute myeloid leukemia. Haematologica 2016; 101:932-940.
63. Lapa C, Luckerath K, Rudelius M, Schmid J S, Schoene A, Schirbel A, et al. [$^{68}$Ga]Pentixafor-PET/CT for imaging of chemokine receptor 4 expression in small cell lung cancer—initial experience. Oncotarget 2016; 7:9288-9295.
64. Lapa C, Luckerath K, Kleinlein I, Monoranu C M, Linsenmann T, Kessler A F, et al. $^{68}$Ga-Pentixafor-PET/CT for Imaging of Chemokine Receptor 4 Expression in Glioblastoma. Theranostics 2016; 6:428-434.
65. Vag T, Gerngross C, Herhaus P, Eiber M, Philipp-Abbrederis K, Graner F P, et al. First Experience with Chemokine Receptor CXCR4-Targeted PET Imaging of Patients with Solid Cancers. J Nucl Med 2016; 57:741-746.
66. Lapa C, Reiter T, Werner R A, Ertl G, Wester H J, Buck A K, et al. [$^{68}$Ga]Pentixafor-PET/CT for Imaging of Chemokine Receptor 4 Expression After Myocardial Infarction. JACC Cardiovasc Imaging 2015; 8:1466-1468.
67. Rischpler C, Nekolla S G, Kossmann H, Dirschinger R J, Schottelius M, Hyafil F, et al. Upregulated myocardial CXCR4-expression after myocardial infarction assessed by simultaneous GA-68 pentixafor PET/MRI. J Nucl Cardiol 2016; 23:131-133.
68. Thackeray J T, Derlin T, Haghikia A, Napp L C, Wang Y, Ross T L, et al. Molecular Imaging of the Chemokine Receptor CXCR4 After Acute Myocardial Infarction. JACC Cardiovasc Imaging 2015; 8:1417-1426.
69. Schmid J S, Schirbel A, Buck A K, Kropf S, Wester H J, Lapa C. [$^{68}$Ga]Pentixafor-Positron Emission Tomography/Computed Tomography Detects Chemokine Receptor CXCR4 Expression After Ischemic Stroke. Circ Cardiovasc Imaging 2016; 9:e005217.
70. Hyafil F, Pelisek J, Laitinen I, Schottelius M, Mohring M, Doring Y, et al. Imaging the Cytokine Receptor CXCR4 in Atherosclerotic Plaques with the Radiotracer $^{68}$Ga-Pentixafor for PET. J Nucl Med 2017; 58:499-506.
71. Li X, Heber D, Leike T, Beitzke D, Lu X, Zhang X, et al. [$^{68}$Ga]Pentixafor-PET/MRI for the detection of Chemokine receptor 4 expression in atherosclerotic plaques. Eur J Nucl Med Mol Imaging 2017.
72. Weiberg D, Thackeray J T, Daum G, Sohns J M, Kropf S, Wester H J, et al. Clinical Molecular Imaging of Chemokine Receptor CXCR4 Expression in Atherosclerotic Plaque using $^{68}$Ga-Pentixafor PET: Correlation with Cardiovascular Risk Factors and Calcified Plaque Burden. J Nucl Med 2017.
73. Bouter C, Meller B, Sahlmann C O, Staab W, Wester H J, Kropf S, et al. Imaging chemokine receptor CXCR4 in chronic infection of the bone with $^{68}$Ga-Pentixafor-PET/CT—first insights. J Nucl Med 2017.
74. Derlin T, Gueler F, Brasen J H, Schmitz J, Hartung D, Herrmann T R, et al. Integrating MRI and Chemokine Receptor CXCR4-Targeted PET for Detection of Leukocyte Infiltration in Complicated Urinary Tract Infections After Kidney Transplantation. J Nucl Med 2017; 58:1831-1837.
75. Schottelius M, Osl T, Poschenrieder A, Herrmann K, Lapa C, Hoffmann F, et al. [$^{177}$Lu]pentixather: preclinical and first patient results with a highly promising CXCR4-directed endoradiotherapeutic agent. Journal of Nuclear Medicine 2015; 56:339-339.
76. Habringer S, Lapa C, Herhaus P, Schottelius M, Istvanffy R, Steiger K, et al. Dual Targeting of Acute Leukemia and Supporting Niche by CXCR4-Directed Theranostics. Theranostics 2018; 8:369-383.
77. Herrmann K, Schottelius M, Lapa C, Osl T, Poschenrieder A, Haenscheid H, et al. First-in-man experience of CXCR4-directed endoradiotherapy with $^{177}$Lu- and $^{90}$Y-labelled pentixather in advanced stage multiple myeloma with extensive intra- and extramedullary disease. Journal of Nuclear Medicine 2015:jnumed. 115.167361.
78. Lapa C, Herrmann K, Schirbel A, Haenscheid H, Luckerath K, Schottelius M, et al. CXCR4-directed endoradiotherapy induces high response rates in extramedullary relapsed Multiple Myeloma. Theranostics 2017; 7:1589-1597.
79. Poschenrieder A, Schottelius M, Schwaiger M, Kessler H, Wester H-J. The influence of different metal-chelate conjugates of pentixafor on the CXCR4 affinity. EJNMMI research 2016; 6:1-8.
80. Poschenrieder A, Schottelius M, Osl T, Schwaiger M, Wester H J. [$^{64}$Cu]NOTA-pentixather enables high resolution PET imaging of CXCR4 expression in a preclinical lymphoma model. EJNMMI Radiopharm Chem 2017; 2:2.
81. Poschenrieder A, Schottelius M, Schwaiger M, Wester H J. Preclinical evaluation of [$^{68}$Ga]NOTA-pentixafor for PET imaging of CXCR4 expression in vivo—a comparison to [$^{68}$Ga]pentixafor. EJNMMI Res 2016; 6:70.
82. Poschenrieder A, Osl T, Schottelius M, Hoffmann F, Wirtz M, Schwaiger M, et al. First $^{18}$F-labeled Pentixafor-based Imaging Agent for PET Imaging of CXCR4-expression in Vivo Tomography 2016; 2:85-93.

The invention claimed is:
1. A compound of the following formula (I)

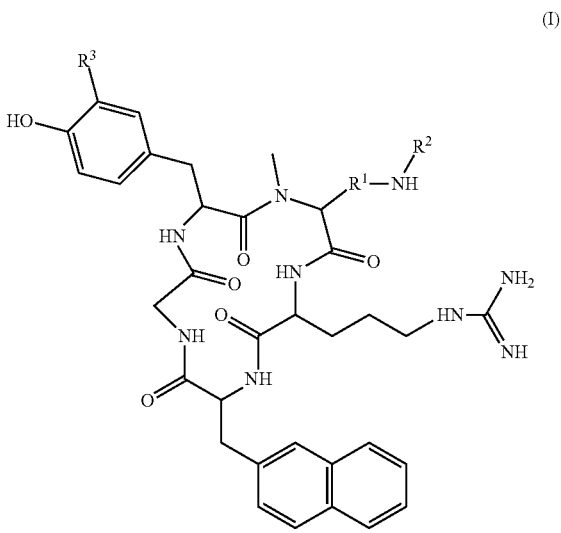

or a pharmaceutically acceptable salt thereof, wherein:

$R^1$ is an alkanediyl chain;

$R^2$ is a group of formula (II):

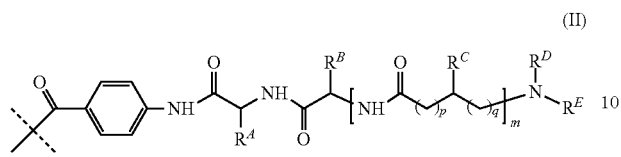

(II)

or a group of formula (IV):

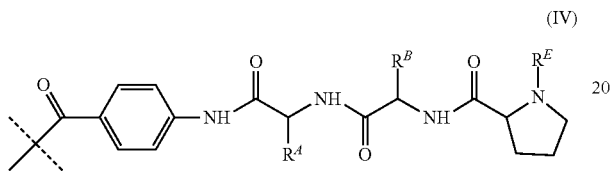

(IV)

which is linked to the remainder of the compound with the bond marked by the dashed line, and wherein $R^A$ is H or alkyl;

$R^B$ is substituted alkyl, which substituted alkyl is substituted with at least one group selected from —$NH_2$ and the guanidino group —NH—C(=NH)—$NH_2$;

$R^C$ is H or optionally substituted alkyl, with one or more optional substituents being selected from —$NH_2$, —NH—C(=NH)—$NH_2$, —COOH, —$CONH_2$, —OH, —SH, —S—$CH_3$, and 5- to 10-membered carbocycle or 5- to 10-membered heterocycle containing oxygen, nitrogen and/or sulfur as heteroatom(s), wherein $R^C$ may be further substituted with or may comprise a cytotoxic moiety;

p is 0, 1 or 2;

q is 0, 1 or 2;

p+q is 0, 1 or 2;

m is 0 or 1;

$R^D$ is H or forms a 5 or 6-membered heterocycle together with the adjacent nitrogen which heterocycle also includes a part of $R^E$;

$R^E$ is a group which comprises at least one of the following:

(i) a chelating moiety, (ii) a chelate formed by a chelating moiety (i) with a chelated radioactive or non-radioactive cation or anion, (iii) a moiety carrying a covalently bound radioisotope, or a precursor suitable to be labeled with such radioisotopes, (iv) a cytotoxic moiety, and (v) a fluorescent moiety; and $R^3$ is H or I.

2. The compound or salt of claim 1, wherein the compound has the formula (Ia):

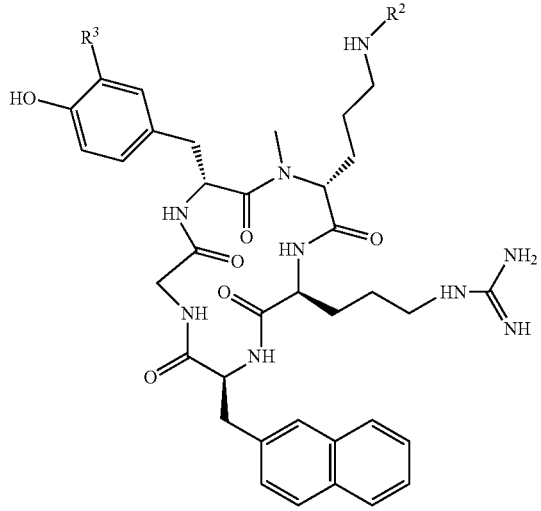

(Ia)

and wherein $R^2$ and $R^3$ are defined as in claim 1.

3. The compound or salt of claim 1, wherein the compound has the formula (Ib):

(Ib)

and wherein $R^2$ and $R^3$ are defined as in claim 1.

4. The compound or salt of claim 1, wherein $R^B$ is substituted linear C1-C6 alkyl, which is substituted at its terminal carbon with one group selected from —$NH_2$ and —NH—C(=NH)—$NH_2$.

5. The compound or salt of claim 1, wherein $R^2$ has the formula (IIa)

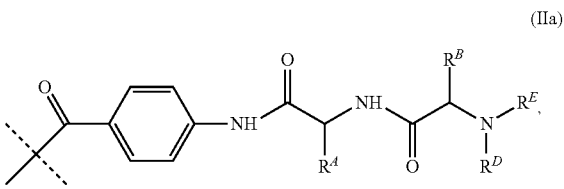

(IIa)

wherein $R^A$, $R^B$, $R^D$ and $R^E$ are defined as in claim 1.

6. The compound or salt of claim 1, wherein $R^2$ has a formula selected from formulae (IIb) and (IId):

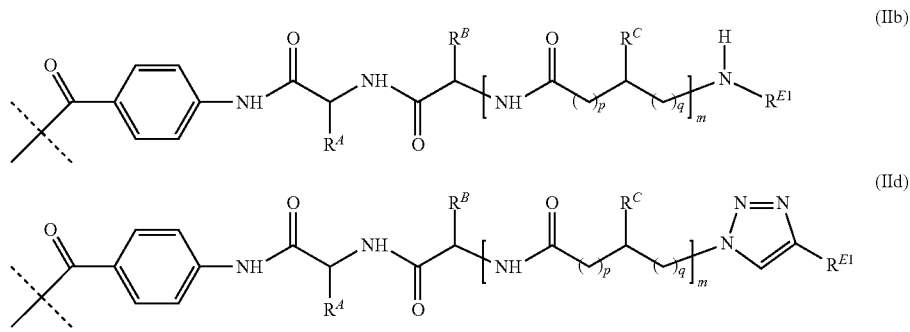

(IIb)

(IId)

wherein
$R^A$, $R^B$, $R^C$, p, q and m are defined as in claim 1, and $R^{E1}$ is a group which comprises at least one of the following:
(i) a chelating moiety,
(ii) a chelate formed by a chelating moiety (i) with a chelated radioactive or non-radioactive cation or anion,
(iii) a moiety carrying a covalently bound radioisotope, or a precursor suitable to be labeled with such a radioisotope,
(iv) a cytotoxic moiety, and
(v) a fluorescent moiety.

7. The compound or salt of claim 1, wherein $R^E$ is selected from (i) a group which comprises a chelating moiety, and (ii) a chelate formed by a chelating moiety (i) with a chelated radioactive or non-radioactive cation or anion, and wherein the chelating moiety comprises at least one of
  a macrocyclic ring structure with 8 to 20 ring atoms of which 2 or more are selected from oxygen atoms, sulfur atoms and nitrogen atoms; and
  an acyclic, open chain chelating structure with 8 to 20 main chain atoms of which 2 or more are heteroatoms selected from oxygen atoms, sulfur atoms and nitrogen atoms.

8. The compound or salt of claim 1, wherein $R^2$ has a formula selected from formulae (IIf) to (IIh):

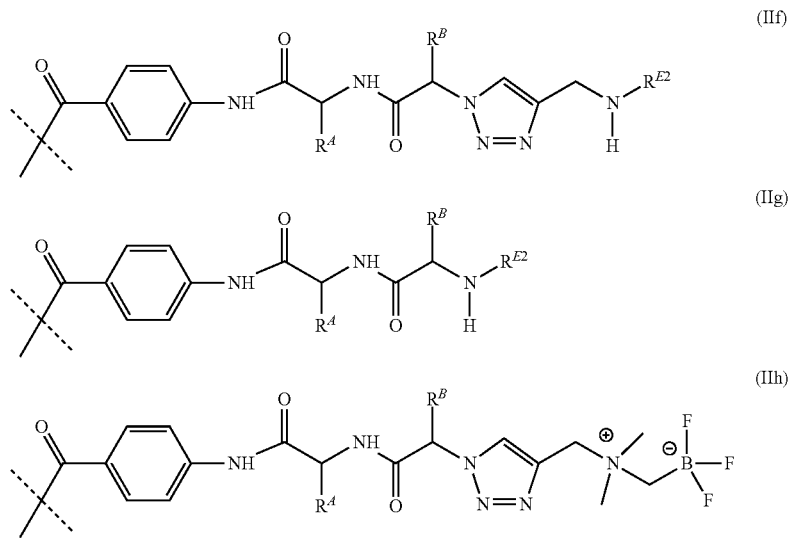

(IIf)

(IIg)

(IIh)

wherein

R$^A$, R$^B$, are defined as in claim 1, and

R$^{E2}$ is selected from (i) a residue of a chelating agent comprising a carboxyl group and (ii) a chelate formed by a residue of a chelating agent comprising a carboxyl group with a chelated radioactive or non-radioactive cation, said residue being obtainable by forming an amide bond from the carboxyl group of the chelating agent and the nitrogen atom to which R$^{E2}$ is attached.

9. A pharmaceutical composition comprising or consisting of a compound or salt of claim 1 and an excipient.

10. A method of diagnosing, preventing, or treating a disease or disorder in a patient in need thereof, comprising administering to the patient a compound or salt of claim 1.

11. The method of claim 10, wherein the method further comprises the use of nuclear medicine, nuclear molecular imaging, optical imaging, or targeted endoradiotherapy.

12. The method of claim 10, wherein the method is further defined as treating or preventing a disease or disorder associated with increased expression of chemokine receptors subtype 4 (CXCR4).

13. The method of claim 10, wherein the method is further defined as diagnosing cancer or cardiovascular disease.

14. The method of claim 12, wherein the disease is cancer or a lymphoproliferative disease.

15. The method of claim 10, wherein the disease or disorder is cardiovascular disease, AIDS, or an inflammatory disorder.

16. A compound of the following formula (I)

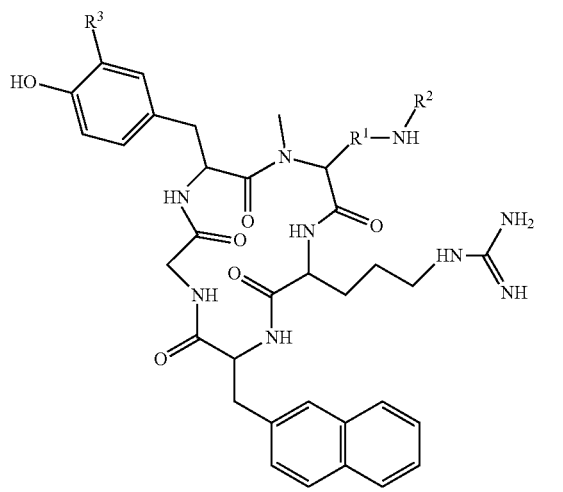

(I)

or a pharmaceutically acceptable salt thereof, wherein:

R$^1$ is an alkanediyl chain;

R$^2$ is a group of formula (III):

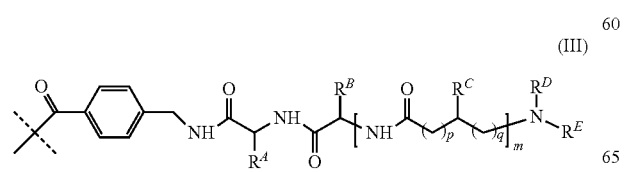

(III)

which is linked to the remainder of the compound with the bond marked by the dashed line, and wherein R$^A$ is H or alkyl;

R$^B$ is substituted alkyl, which substituted alkyl is substituted with at least one group selected from —NH$_2$ and the guanidino group —NH—C(=NH)—NH$_2$;

R$^C$ is H or optionally substituted alkyl, with one or more optional substituents being selected from —NH$_2$, -NH—C(=NH)—NH$_2$, —COOH, —CONH$_2$, —OH, —SH, —S—CH$_3$, and 5- to 10-membered carbocycle or 5- to 10-membered heterocycle containing oxygen, nitrogen and/or sulfur as heteroatom(s), wherein R$^C$ may be further substituted with or may comprise a cytotoxic moiety;

p is 0, 1 or 2;

q is 0, 1 or 2;

p+q is 0, 1 or 2;

m is 0 or 1;

R$^D$ is H or forms a 5 or 6-membered heterocycle together with the adjacent nitrogen which heterocycle also includes a part of R$^E$;

R$^E$ is a group which comprises at least one of the following:

(i) a chelating moiety, (ii) a chelate formed by a chelating moiety (i) with a chelated radioactive or non-radioactive cation or anion, (iii) a moiety carrying a covalently bound radioisotope, or a precursor suitable to be labeled with such radioisotopes, (iv) a cytotoxic moiety, and (v) a fluorescent moiety; and R$^3$ is H or I.

17. The compound or salt of claim 16, wherein the compound has the formula (Ia):

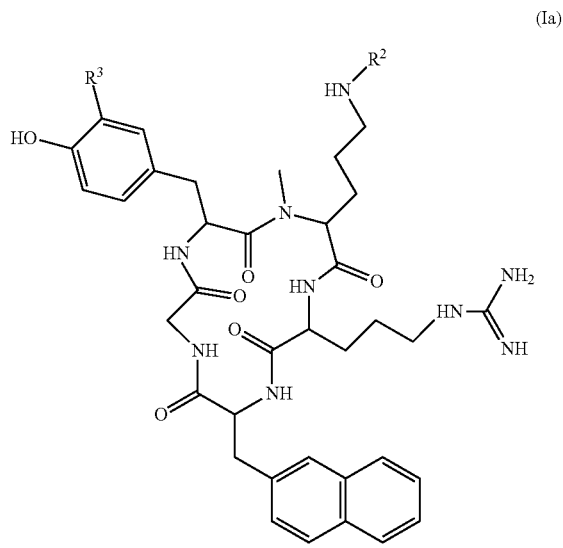

(Ia)

and wherein R$^2$ and R$^3$ are defined as in claim 16.

18. The compound or salt of claim 16, wherein the compound has the formula (Ib):

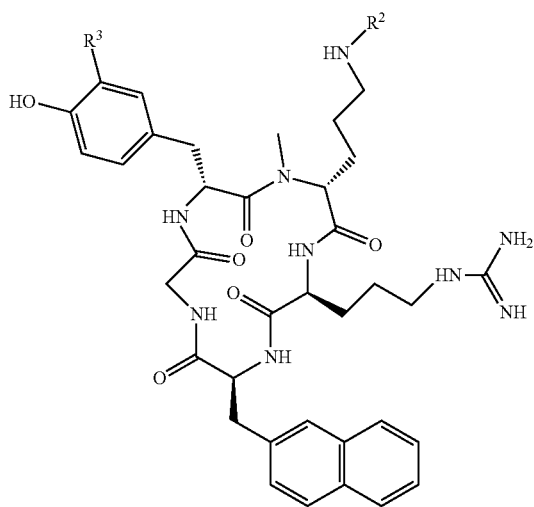

and wherein R² and R³ are defined as in claim 16.

19. The compound or salt of claim 16, wherein $R^B$ is substituted linear C1-6 alkyl, which is substituted at its terminal carbon with one group selected from —NH₂ and —NH—C(=NH)—NH₂.

20. The compound or salt of claim 16, wherein R² has the formula (IIIa)

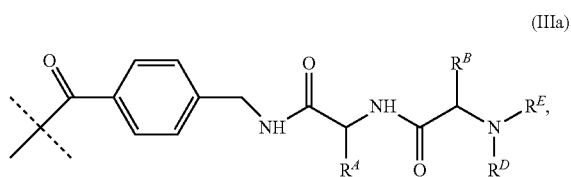

(IIIa)

wherein $R^A$, $R^B$, $R^D$ and $R^E$ are defined as in claim 16.

21. The compound or salt of claim 16, wherein $R^E$ is selected from (i) a group which comprises a chelating moiety, and (ii) a chelate formed by a chelating moiety (i) with a chelated radioactive or non-radioactive cation or anion, and wherein the chelating moiety comprises at least one of a macrocyclic ring structure with 8 to 20 ring atoms of which 2 or more are selected from oxygen atoms, sulfur atoms and nitrogen atoms; and an acyclic, open chain chelating structure with 8 to 20 main chain atoms of which 2 or more are heteroatoms selected from oxygen atoms, sulfur atoms and nitrogen atoms.

22. A pharmaceutical composition comprising or consisting of a compound or salt of claim 16 and an excipient.

23. A method of diagnosing, preventing, or treating a disease or disorder in a patient in need thereof, comprising administering to the patient a compound or salt of claim 16.

24. The method of claim 23, wherein the method further comprises the use of nuclear medicine, nuclear molecular imaging, optical imaging, or targeted endoradiotherapy.

25. The method of claim 23, wherein the method is further defined as treating or preventing a disease or disorder associated with increased expression of chemokine receptors subtype 4 (CXCR4).

26. The method of claim 23, wherein the method is further defined as diagnosing cancer or cardiovascular disease.

27. The method of claim 25, wherein the disease is cancer or a lymphoproliferative disease.

28. The method of claim 23, wherein the disease or disorder is cardiovascular disease, AIDS, or an inflammatory disorder.

* * * * *